US008088774B2

(12) United States Patent
Watterson et al.

(10) Patent No.: US 8,088,774 B2
(45) Date of Patent: Jan. 3, 2012

(54) ANTI-INFLAMMATORY AND PROTEIN KINASE INHIBITOR COMPOSITIONS AND RELATED METHODS FOR DOWNREGULATION OF DETRIMENTAL CELLULAR RESPONSES AND INHIBITION OF CELL DEATH

(75) Inventors: Daniel Martin Watterson, Chicago, IL (US); Anu R. Sawkar, La Jolla, CA (US); Thomas J. Lukas, Evanston, IL (US); Salida Mirzoeva, Chicago, IL (US); Linda J. Van Eldik, Chicago, IL (US); Marcel Hibert, Eschau (FR); Anastasia Velentza, Chicago, IL (US); Magdalena Zasadzki, Arlington Heights, IL (US); Jacques Haiech, Strasbourg (FR); Jean-Jacques Bourguignon, Illkirch Graffenstaden (FR)

(73) Assignees: Northwestern University, Evanston, IL (US); Universite de Strasbourg, Strasbourg Cedex (FR); Centre National de la Recherche Scientifique, A Scientific Research Centre, Paris Cedix (FR)

(*) Notice: Subject to any disclaimer, the term of this patent is extended or adjusted under 35 U.S.C. 154(b) by 0 days.

(21) Appl. No.: 12/831,787

(22) Filed: Jul. 7, 2010

(65) Prior Publication Data
US 2010/0317665 A1  Dec. 16, 2010

Related U.S. Application Data

(63) Continuation of application No. 11/259,522, filed on Oct. 26, 2005, now Pat. No. 7,888,357, which is a continuation of application No. 10/235,427, filed on Sep. 3, 2002, now abandoned.

(60) Provisional application No. 60/316,909, filed on Aug. 31, 2001.

(51) Int. Cl.
*A61K 31/501* (2006.01)
*C07D 403/12* (2006.01)

(52) U.S. Cl. .................... 514/252.02; 544/238

(58) Field of Classification Search .......... None
See application file for complete search history.

(56) References Cited

U.S. PATENT DOCUMENTS

| 2,857,384 | A |  | 10/1958 | Druey et al. |
|---|---|---|---|---|
| 4,169,158 | A |  | 9/1979 | Laborit |
| 4,508,720 | A |  | 4/1985 | Kan et al. |
| 4,710,499 | A |  | 12/1987 | Wermuth et al. |
| 4,721,711 | A |  | 1/1988 | Chambon et al. |
| 4,977,152 | A |  | 12/1990 | Biziere et al. |
| 5,045,541 | A |  | 9/1991 | Nakao et al. |
| 5,484,940 | A |  | 1/1996 | Grant et al. |
| 7,732,445 | B2 | * | 6/2010 | Watterson et al. ............ 514/247 |
| 2003/0176437 | A1 |  | 9/2003 | Watterson et al. |
| 2006/0073472 | A1 |  | 4/2006 | Watterson et al. |
| 2008/0021035 | A1 |  | 1/2008 | Watterson et al. |
| 2008/0318899 | A1 |  | 12/2008 | Watterson et al. |
| 2009/0029985 | A1 |  | 1/2009 | Watterson et al. |
| 2010/0130442 | A1 | * | 5/2010 | Wadgaonkar et al. ......... 514/53 |
| 2010/0240668 | A1 | * | 9/2010 | Watterson et al. ....... 514/252.02 |

FOREIGN PATENT DOCUMENTS

| EP | 0072726 | 2/1983 |
|---|---|---|
| EP | 0211457 | 2/1987 |
| EP | 0382634 | 8/1990 |
| EP | 0628550 | 12/1994 |
| EP | 1061077 | 12/2000 |
| FR | 2141697 | 1/1973 |
| FR | 2847253 | 5/2004 |
| WO | WO 98/46574 | 10/1998 |
| WO | WO 01/42241 | 6/2001 |
| WO | WO 02/22605 | 3/2002 |
| WO | WO 03/018503 | 3/2003 |
| WO | WO 03/047577 | 6/2003 |
| WO | WO 2004/046117 | 6/2004 |
| WO | WO 2005/009976 | 2/2005 |
| WO | WO 2005/061509 | 7/2005 |
| WO | WO 2005/063761 | 7/2005 |
| WO | WO 2006/026135 | 3/2006 |
| WO | WO 2006/050389 | 5/2006 |
| WO | WO 2006/050359 | 6/2006 |
| WO | WO 2007/127375 | 4/2007 |
| WO | WO 2007/127475 | 4/2007 |
| WO | WO 2007/130383 | 4/2007 |
| WO | WO 2007/127448 | 11/2007 |
| WO | WO 2007/127474 | 11/2007 |
| WO | WO 2008/109437 | 9/2008 |

OTHER PUBLICATIONS

Matyus, Peter et al., "Some Aspects of the Chemistry of Pyrimido[1,2-b]pyridazinones", Journal of Heterocyclic Chemistry, 25(5), 1535-1542, 1988.*
Communication for related European Patent Application No. 05823123 dated Jun. 2, 2009.
Communication for related European Patent Application No. 05823123 dated Dec. 17, 2009.
Database Beilstein, XP002525678 and J. Heterocyclic Chemistry, 1981, vol. 18, pp. 189, Feb. 17, 2009.
Database Caplus, Chemical Abstract Service, XP002515675 and JP63295577, Feb. 18, 2009.
Database Caplus, Chemical Abstract Service, XP002525677 and comptes rendues des séances de L'Academie des Sciences, Serie C: Sciences Chimiques, 1973, vol. 277, No. 8, pp. 319-322.
Sotelo et al., "Efficient Aromatization of 4,5-Dihydro-3(2H)-Pyridazinones Substituted at 5 Position by Using Anhydrous Copper (II) Choloride," Synthetic Communications, 30 (1): pp. 1-7, 2000.
Extended European Search Report for related European Application No. 10181297 dated Nov. 12, 2010.
Matyus, P. et al., "Some aspects of the chemistry of pyrimidol[1,2-b]pyridazinones," J. Heterocyclics Chem., 1988, vol. 25, pp. 1535, 1537, 1539, & 1541.

(Continued)

Primary Examiner — Fiona T Powers
(74) Attorney, Agent, or Firm — Millen, White, Zelano & Branigan, P.C.

(57) ABSTRACT

A novel class of pyridazine compositions and related methods of use.

20 Claims, 10 Drawing Sheets

OTHER PUBLICATIONS

Reply to Communication for related European Patent Application No. 05823123 dated Dec. 8, 2009.

Restriction Requirement for related U.S. Appl. No. 12/119,208 mailed Mar. 4, 2010.

Response to Restriction Requirement for related U.S. Appl. No. 12/119,208, filed Aug. 4, 2010.

Search Report dated Feb. 18, 2009 for related European Patent Application No. 05823123.

Adams et al. (2004) "Concise Synthesis of 1H-pyrazin-2-ones and 2-Aminopyrazines". Synlett. 11:2031-2033.

Akama et al. (1998) "Amyloid β-peptide stimulates nitric oxide production in astrocytes through an NFxB-dependent mechanism". *PNAS.* 95:5795-5800.

Akiyama et al. (2000) "Inflammation and Alzheimer's Disease". *Neurobiol Aging.* 21:383-421.

Allen and Van Allen, (1961) J. American Chem Society 73: 5856.

Apter, et al. (1999) "*Buspirone: Future Directions*". *J Clin Psychopharmacol.* 19:86-93.

Badger, et al. (1996) "Pharmacological Profile of SB 203580, a Selective Inhibitor of Cytokine Suppressive Binding Protein/p38 Kinase, in Animal Models of Arthritis, Bone Resorption, Endotoxin Shock and Immune Function". *J. Pharmacol Exp Ther.* 279:1453-1461.

Bhagwat, et al. (1999) "Gene-regulating protein kinases as important anti-inflammatory targets" Drug Disc. Today, 4 472-479.

Bhat, et al. (1998) "Extracellular Signal-regulated Kinase and p38 Subgroups of Mitogen-Activated Protein Kinases Regulate Inducible Nitric Oxide Synthase and Tumor Necrosis Factor-alpha Gene Expression in Endotoxin-Stimulated Primary Glial Cultures". J Neurosci. 18 1633-1641.

Blasi, et al. (1990) "Immortalization of murine microglial cells by a v-raf/v-myc carrying retrovirus". J. Neuroimmunol, 27 229-237.

Brott, et al. (2000) "Treatment of acute ischemic stroke", N Engl J Med. Sep. 7, 2000;343(10):710-22.

Cardona et al. (2006) "Control of microglial neurotoxicity by the fractalkine receptor". Nature Neurosci. 9:917-924.

Chayer, S et al. (1998) "(3-Pyridazinamin-3-yl) Alpha-Aminoacids: A Facilitated Method of Preparation of Phenylalanine and Proline Representatives". Tetrahedron Letters. 39:841-844.

Chitaley, K et al. (2001) "Antagonism of Rho-kinase Stimulates Rat Penile Erection Via a Nitric Oxide-Independent Pathway" Nature Medicine, Jan. 2001, 119-122, vol. 7, No. 1.

Cignarella G, et al. (1989) "Synthesis and biological evaluation of substituted benzo[A]cinnolinones and 3H-benzo[6,7]cycloheptal[1,2-c]pyridazinones: higher homologues of the antihypertensive and antithrombotic 5H-indeno[1,2- c]pyridazinones". *J. Med. Chem.* 32: 2277-2282.

Contreras et al. (1999) "Aminopyridazines as Acetylcholinesterase Inhibitors". *J. of Med. Chem.* 42(4)730-741.

Contreras et al. (2001) "Design, Synthesis, and Structure—Activity Relationships of a Series of 3-[2-(1-Benzylpiperidin-4-yl)ethylamino]pyridazine Derivatives as Acetylcholinesterase Inhibitors". *Journal of Medicinal Chemistry.* 44(17):2707-2718.

Costantino et al. (1996) "Synthesis, activity, and molecular modeling of a new series of tricyclic pyridazinones as selective aldose reductase inhibitors". *J Med Chem.* 39:4396-4405.

Coudert et al. (1988) "A new synthetic route to 4,6-diarylpyridazinones and some of their derivatives". *Journal of Heterocyclic Chemistry.* 25(3):799-802.

Craft JM , Watterson and van Eldik (2006) "Human amyloid beta-induced neuroinflammation is an early event in neurodegeneration", Glia 53:484-490.

Craft JM, et al. (2004). "Aminopyridazines attenuate hippocampus dependent behavioral deficits induced by human (J-amyloid in a murine model of neuroinflammation". *J Mol Neurosci.* 24:115-122.

Craft JM, Watterson DM, Frautschy SA and Van Eldik LJ. (2004) "Aminopyridazines inhibit β-amyloid induced glial activation and neuronal damage in vivo". *Neurobiol. Aging.* 25:1283-1292.

Craft, J.M et al. (2005) "Neuroinflammation: a potential therapeutic target". *Expert Opin. Ther. Targets.* 9:887-900.

Csende, F et al. (1995) "Copper(II) Chloride as an Efficient Reagent for the Dehydrogenation of Pyridazinone Derivatives". Synthesis. 1240-1242.

Da Silva, et al. (1997) "Blockade of p38 Mitogen-activated Protein Kinase Pathway Inhibits Inducibel Nitric-oxide Synthase Expression in Mouse Astrocytes". *J Biol Chem.* 272:28373-28380.

Donato, R. (1999) "Functional roles of S100 proteins, calcium-binding proteins of the EF-hand type". *Biochim Biophys Acta.* 1450 191-231.

Dos Santos, (2000) "Invited review: mechanisms of ventilator-induced lung injury: a perspective." Appl Physiol, Oct. 2000;89(4):1645-55.

Du, Y. et al. (2000) "Association of an interleukin 1[alpha] polymorphism with Alzheimer's disease". *Neurology* 55:480-484.

Enyedy, I.J. et al "Pharmacophore-based discovery of substituted pyridines as novel dopamine transporter inhibitors" Bioorganic & Medicinal Chemistry Letters 13(3) 513-517 (2003).

Farlow, M.R. "Utilizing combination therapy in the treatment of Alzheimer's disease" Expert review of Neurotherapeutics 4(5) 799-808 (2004).

Finlayson et al., 2004"Acquired QT interval prolongation and HERG: implications for drug discovery and development", Eur J Pharmacol. Oct. 1, 2004;500(1-3):129-42.

Frautschy SA, Yang F, Calderon L and Cole GM. (1996) "Rodent models of Alzheimer's disease: rat A β infusion approaches to amyloid deposits". *Neurobiol Aging.* 17:311-21.

Garattini, et al. (1982) "Notes on Buspirone's Mechanisms of Action". *J Clin Psych.* 43:19-24.

Garcia. (1995) "Regulation of Endothelial Cell Gap Formation and Barrier Dysfunction: Role of Myosin Light Chain Phosphorylation". *J Cell Physiol.* 163:510-522.

Ghajar, et al. (2000) "Traumatic brain injury", Lancet, Sep. 9, 2000;356(9233):923-9.

Gibbs, J. (2000) "Mechanism-based target identification and drug discovery in cancer research". *Science.* 287:1969-1973.

Griffin, et al. (1989) "Brain interleukin 1 and S-100 immunoreactivity are elevated in Down syndrome and Alzheimer disease". PNAS 86:7611-7615.

Griffin, et al. (1998) "Glial-Neuronal Interactions in Alzheimer's Disease: The Potential Role of a 'Cytokin Cycle' in Disease Progression". *Brain Pathol.* 8:65-72.

Guo, L. et al. (2001) "Similar Activation of Glial Cultures from Different Rat Brain Regions by Neuroinflammatory Stimuli and Downregulation of the Activation by a New Class of Small Molecule Ligands" Neurobiol Aging:Nov.-Dec. 2001; 975-981, 22(6).

Hansen, KB et al. (2005) "First Generation Process for the Preparation of the DDP-IV Inhibitor Sitagliptin". Organic process research & development. 9:634-639.

Heinisch , G and Frank, H, "4 Pharmacologically active pyridazine derivatives. Part 2," (1992) Prog Med Chem 29, 141-183.

Heinisch, G. et al. (1990) "Pharmacologically active pyridazine derivatives". Part I, *Prog. Med. Chem.* 27:1-49.

Hirohashi et al. (1991) "Pharmacological Studies with the Alpha2-Adrenoceptor Antagonist Midaglizole". Arzneim.-Forsch./Drug Res 41:9-18.

Hu W et al. (2005) "Validation of the Neuroinflammation Cycle as a Drug Discovery Target Using Integrative Chemical Biology and Lead Compound Development with an Alzheimer's Disease-Related Mouse Model". *Current Alzheimer's Research.* 2:197-205.

Hu W, Ralay Ranaivo H, Roy S, et al. (2007) "Development of a novel therapeutic suppressor of brain pro-inflammatory cytokine up-regulation that attenuates synaptic dysfunction and behavioral deficits". Bioorgan Med Chem Lett.17:414-418 (Watterson).

Hu, et al. (1996) "S100-β Stimulates Inducible Nitric Oxide Synthase Activity and mRNA Levels in Rat Cortical Astrocytes".*J. Biol Chem* 271:2543-2547.

Hu, et al. (1998) "Amyloid-β peptide activates cultured astrocytes: morphological alterations, cytokine induction and nitric oxide release". *Brain Res.* 785:195-206.

Hu, et al. (1998) "Apolipoprotein E Attenuates β-Amyloid-Induced Astrocyte Activation", *J. Neurochem.* 7:1626-1634.

Hu, W et al, "Pyridazines as a New Chemotype for Alzheimer's Disease Drug Discovery that Targets Disease Progression", 29th National Medicinal Chemistry Symposium, University of Wisconsin—Madison, Jun. 27-Jul. 1, 2004, Abstract and Poster.
Jones, RG. (1949) "Pyrazines and Related Compounds. I. A New Synthesis of Hydroxypyrazines". J. Amer. Chem. Soc. 71:78-81.
Karpus WJ et al, 2008"Inhibition of experimental autoimmune encephalomyelitis by a novel small molecular weight proinflammatory cytokine suppressing drug" J Neuroimmunology 203(1)73-8.
LaDu, et al. (2000) "Apolipoprotein E Receptors Mediate the Effects of β-Amyloid on Astrocyte Cultures". *J. Biol Chem*. 275:33974-33980.
LaDu, et al. (2001) "Apolipoprotein E and apolipoprotein E receptors modulate A β-induced glial neuroinflammatory responses". *Neurochem Intl*. 39:427-434.
Lam, et al. (2001) "Mechanism of glial activation by S100B: involvement of the transcription factor NFxB". *Neurobiol Aging*. 22:765-772.
Lambert, et al. (1998) "Diffusible, nonfribrillar ligands derived from Alpha-bete1-42 are potent central nervous system neurotoxins". *PNAS* 95:6448-6453.
Laskowitz, et al. (2001) "Downregulation of Microglial Activation by Apolipoprotein E and ApoE-Mimetic Peptides", *Exp Neurol*. 167:74-85.
Maroney, et al. (1999) "CEP-1347 (KT7515), an Inhibitor of JNK Activation, Rescues Sympathetic Neurons and Neuronally Differentiated PC12 Cells from Death Evoked by Three Distinct Insults". *J. Neurochem*. 73:1901-1912.
Maroney, et al. (2001,)Cep-1347 (KT7515), a semisynthetic inhibitor of the mixed lineage kinase family J Biol Chem. Jul. 6, 2001:276(27):25302-8. Epub Apr. 26, 2001.
Melikian, et al. (1992) "Condensation of Muscimol or Thiomuscimol with Aminopyridazines Yields GABA-A Antagonists". *J Med Chem*. 35 4092-4097.
Merck: "The Merck Manual" 1999 Merck & Co. U.S.A. p. 1398, col. 2 "prognosis and treatment of Alzheimer's disease".
Mirzoeva, et al. (1999) "Screening in a cell-based assay for inhibitors of microglial nitric oxide production reveals calmodulin0regulated protein kinases as potential drug discovery targets". *Brain Res*. 844:126-134.
Mirzoeva et al. "Discovery of a 3-Amino-6-phenyl-pyridazine Derivative as a New Synthetic Antineuroinflammatory Compound" Journal of Medicinal Chemistry, 2002, vol. 45, No. 3, pp. 563-566.
Munoz, L et al, (2007) A novel p38 alpha MAPK inhibitor suppresses brain proinflammatory cytokine up.
Namura, et al. (2001, ") Intravenous administration of MEK inhibitor U0126 affords brain protection against forebrain ischemic and focal cerebral ischemia", Proc Natl Acad Sci U S A, Sep. 25, 2001; 98(20):11569-74. Epub Aug. 14, 2001.
Nelson, et al (2006) "Compound holds promise for neurodegenerative diseases" Lancet Neurology 5 (3) 210.
Parker, J. 2000,"Inhibitors of myosin light chain kinase and phosphodiesterase reduce ventilator-induced lung injury." J Appl Physiol. Dec. 2000:89(6):2241-8.
Petrova, et al. (1999) "Cyclopentenone prostaglandins suppress activation of microglia: Down-regulation of induciblee nitric-oxide synthase by 15-deoxy-Δ 12, 14 -prostaglandin J2", *PNAS* 96:4668-4673.
Pirvola, U. et al. (2000) "Rescue of Hearing, Auditory Hair Cells, and Neurons by CEP-1347/KT7515, an Inhibitor of c-Jun N-Terminal Kinase Activation". *J. Neurosci*, 20:43-50.
Prusiner, S.B. (2001) "Shattuck Lecture—Neurodegenerative Diseases and Prions". *New Engl. J. Med.* 344:1516-1526.
Ranaivo, HR et al "Glia as a therapeutic target: selective suppression of human amyloid-beta-induced upregulation of brain proinflammatory cytokine production attenuates neurodegeneration", Journal of Neuroscience 26(2) 662-670, 2006.
Ranaivo, HR et al , "Development of Orally Bioavailable Pyridazines that Suppress Neuroinflammation", 9th International Symposium on the Chemistry and Pharmacology of Pyridazines, Antwerp. Belgium, Jul. 2004, Abstract and Poster.
Recanatini et al., 2005 "QT prolongation through hERG K(+) channel blockade: current knowledge and strategies for the early prediction during drug development"; Med Res Rev. Mar. 2005:25(2):133-66.

Roden, 2004, "Drug-induced prolongation of the QT interval." N Engl J Med. Mar. 4, 2005;350(10)1013-22.
Saturnino, C et al, (1995) Heterocyles 41, 1491.
Schumacher A. et al. Death Associated Protein Kinase as a Potential Therapeutic Target; Ashley Publications, Aug. 2002, 497-506, vol. 6, No. 4.
Selkoe, D.J. (2001) "Alzheimer's Disease: Genes, Proteins, and Therapy". *Physiol. Rev.* 81:741-766.
Sheng J, et al. (1996) "In vivo and in vitro evidence supporting a role for the inflammatory cytokine interleukin-1 as a driving force in Alzheimer pathogenesis". Neurobiol. Aging. 17:761-766.
Somera-Molena KC et al, (2007) "Glial activation links early-life seizures and long-term neurologic dysfunction: evidence using a small molecule inhibitor of pro-inflammatory cytokine upregulation." Epilepsia 48: 1785-1800.
Sotelo E and Ravina E. (2000) "Efficient aromatization of 4,5-dihydro-3-(2H)-pyridazinones substituted at 5 position by using anhydrous copper (II) chloride". *Synthetic Communications*. 30:1-7.
Sridhar, et al. (2000) "Protein Kinases as Therapeutics Targets". *Pharm Res*. 17:1345-1353.
Stahl PH and CG Wermuth, 2002, Verlag Helvetica Chimica Acta & Wiley-Vch, Weinheim, XP002459552.
Stevens. (2001) "NHLBI workshop report: endothelial cell phenotypes in heart, lung, and blood diseases", Am J Physiol Cell Physiol, Nov. 2001;281(5):C1422-33.
Strohmeyer R. Rogers J. (2001) "Molecular and cellular mediators of Alzheimer's disease inflammation". J Alz Dis. 3:131-157.
Tereshko, et al. (2001), "Crystal structures of the catalytic domain of human protein kinase associated with apoptosis and tumor suppression." Nat Struct Biol. Oct. 2001;8(10):899-907.
Tinsley. (2000)"Myosin light chain kinase transference induces myosin light chain activation and endothelial hyperpermeability.", Am J Physiol Cell Physiol. Oct. 2000;279(4):C1285-9.
Toma, L. et al. "6-Chloropyralazin-3-yl Derivatives Active as Nicotinic Agents: Synthesis Binding, and Modeling Studies" Journal of Medicinal Chemistry, J. Med. Chem. 2002, 4011-4017, 45 (18).
Troy, C.M. et al. (2001) "β-amyloid-induced neuronal apoptosis required c-Jun N-terminal kinase activation," *J. Neurochem* 77:157-164.
Van Eldik et al (2007) "Glia proinflammatory cytokine upregulation as a therapeutic target for neurodegenerative diseases: function-based and target-based discovery approaches", Int Rev Neurobiol 82:277-96.
Van Eldik et al. and Griffin WST (1994) "S100 beta expression in Alzheimer's disease: relation to neuropathology in brain regions". *Biochim Biophys Acta*. 1223:398-403.
Van Eldik LJ, Wainwright MS. (2003) "The Janus face of glial-derived S100B; beneficial and detrimental functions in the brain". Restorative Neurol Neurosci. 21:97-108.
Van Eldik, et al. (1988) "Synthesis and Expression of a Gene Coding for the Calrium-modulated Protein S100B and Designed for Cassette-based, Site-directed Mutagenesis". *J. Biol. Chem*. 263:7830-7837.
Van Eldik, L, "Attenuation of Human Abeta-induced Neuroinflammation, Neuronal Death, and Hippocampus-Dependent Behavioral Deficits by a New Class of Bioavailable Small Molecules", Presentation, CNS Diseases Congress: Advances in Therapeutics, Tools and Trials, Philadephia, Jun. 28-29, 2004.
Van Niel MB et al, J Med Chem (2005) 48(19):6004-11 (Merck).
Veber et al. (2002) "Molecular 30 properties that influence the oral bioavailability of drug candidates". J Med. Chem. 45:2615-2623.
Velentza et al. (2001) "A protein kinase associated with apoptosis and tumor suppression: Structure, Activity and Discovery of Peptide Substrates" *Journal of Biological Chemistry*. 276(42):38956-38965.
Velentza AV et al, "Discovery of Substrates and Small Molecule Inhibitors for a Death Associated Protein Kinase"; Cellular & Molecular Biology Letters, International Scientific Journal; 2nd International Conference on Inhibitors of Protein Kinases, Sep. 2001, 484, vol. 6, No. 2B.
Velentza et al, "Structure, Activity, Regulation, and Inhibitor Discovery for a Protein Kinase Associated With Apoptosis and Neuronal Death"; Pharmacology & Therapeutics, 2002.

Vieth et al, (2004) "Characteristic physical properties and structural fragments of marketed oral drugs". *J. Med Chem.* 47:224-232.

Wainwright, M et al "Protein kinase involved in lung injury susceptibility: evidence from enzyme isoform genetic knockout and in vivo inhibitor treatment." Proc Natl Acad Sci U S A. May 13, 2003;100(10):6233.

Watterson, D M., Velentza, AV., Zasadzk,i M., Craft, JM., Haiech, J. & Van Eldik, LJ, (2003) "Discovery of a new class of synthetic protein kinase inhibitors that suppress selective aspects of glial activation and protect against [J-amyloid induced injury. A foundation for future medicinal chemistry efforts focused on targeting Alzheimer's disease progression". J. Mol. Neurosci. 20:411-424.

Watterson, DM, "Development of orally bioavailable small molecule modulators of disease progression in new Alzheimer's Disease related mouse models", Institute for the Study of Aging, Investigator's Meeting, New York, Oct. 7, 2004.

Watterson, DM, "Discovery of new small molecule modulators of disease progression in an Alzheimer's Disease related mouse model", 12th Mainzer Forum in Medicinal Chemistry, Mainz, Germany, Oct. 2004, Presentation.

Watterson, DM et al. "Discovery of New Chemical Classes of Synthetic Ligands that Suppress Neuroinflammatory Responses" Journal of Molecular Neuroscience; 2002, 89-93, vol. 19.

Watterson, DM et al. Ligand Modulation of Glial Activation: Cell Permeable, Small Molecule Inhibitors of Serine-Threonine Protein Kinases Can Block Induction of Interleukin 1β and Nitric Oxide Synthase II; Neurochemistry International, 2001, 459-488, vol. 39.

Wermuth CG. (1998) "Search for new lead compounds: The example of the chemical and pharmacological dissection of aminopyridazines". *J. Heterocyclic Chem.* 35:1091-1100.

Wermuth CG et al. "3-Aminopyridazine Derivatives with Atypical Antidepressant, Serotonergic, and Dopaminergic Activities" Journal of Medicinal Chemistry, vol. 32, No. 3, 1989, pp. 528-537.

Wermuth CG et al. "Synthesis and Structure-Activity Relationships of a Series of Aminopyridazine Derivatives of γ-Aminobutyric Acid Acting as Selective GABA-A Antagonists" Journal of Medicinal Chemistry, 1987, 239-249, vol. 30, No. 2.

Wing L, Behanna H, Van Eldik L. Watterson D, Relay Ranaivo H. De novo and molecular target-independent discovery of orally bioavailable lead compounds for neurological disorders. *Curr Alzheimer Res* 2006; 3:205-214.

Yamamoto, et al. (1999) "Developmental changes in distribution of death-associated protein kinase mRNAs". *J Neurosci Res.* 58:674-683.

Yoshinari et al (2001)"Effects of a dual inhibitor of tumor necrosis factor-alpha and interleukin-1 on lipopolysaccharide-induced lung injury in rats: involvement of the p38 mitogen-activated protein kinase pathway" Crit Care Med. Mar. 2001;29(3):628-34.

Zhou et al. (1998) "HERG-like K+ Channels in Microglia". *J. Gen Physiol.* 111(6):781-94.

Constantino et al., "Synthesis and aldose reductase inhibitory activity of a new series of benzo[h]cinnolinone derivatives," Il Farmaco, 2000, vol. 55, pp. 544-552.

Kumar, C. et al., "Drugs targeted against protein kinases," Expert Opin. Emerging Drugs, 2001, vol. 6, No. 2, pp. 303-315.

Velentza, A. et al., "An aminopyridazine-based Inhibitor of a Pro-apoptotic Protein kinase Attenuates Hypoxia-Ischemia Induced Acute Brain Injury," Bioorganic & Medicinal Chemistry Letters, 2003, vol. 13, pp. 3465-3470.

\* cited by examiner

ANTI-INFLAMMATORY AND PROTEIN KINASE INHIBITOR COMPOSITIONS AND RELATED METHODS FOR DOWNREGULATION OF DETRIMENTAL CELLULAR RESPONSES AND INHIBITION OF CELL DEATH

This application is a continuation of U.S. patent application Ser. No. 11/259,522, filed Oct. 26, 2005, which issued as U.S. Pat. No. 7,888,357, and which is a continuation of U.S. patent application Ser. No. 10/235,427, filed Sep. 3, 2002, which is abandoned, and which claims priority benefit from prior Provisional Application Ser. No. 60/316,909, filed on Aug. 31, 2001, the entirety of which is incorporated herein by reference.

This invention was made with government support under Grant No. AG013939 and Grant No. GM030864 awarded by the National Institutes of Health. The government has certain rights in this invention.

BACKGROUND OF THE INVENTION

Many diseases and conditions of acute or chronic injury have an inflammatory and/or cell death component to them. These disorders can result from a disruption in the homeostatic balance between beneficial and detrimental responses of the organism. For example, there may be a decrease in the production of trophic molecules that mediate cell survival and other beneficial cellular processes, or there may be an overproduction of pro-inflammatory or other detrimental molecules that mediate toxic cellular responses. It is also becoming increasingly appreciated that dysregulation of signal transduction pathways involving protein kinases may be involved in the generation or progression of these diseases. Thus, development of new classes of cell permeable ligands or protein kinase inhibitors that can modulate disease-relevant pathways is an important area for therapeutics. The current invention relates generally to the development of a new class of pyridazine and/or related heterocyclic derivatives that have utility for selective modulation of cellular pathways linked to disease progression and/or protein kinase inhibition relevant to inflammation and/or cell death. In addition to a variety of heterocyclic compositions having utilities including those mentioned above, the present invention also includes various methods relating to the modulation of signal transduction pathways and/or new therapeutic routes relating thereto.

Neuroinflammation is a characteristic feature of disease pathology and progression in a diverse array of neurodegenerative disorders that are increasing in their societal impact (for a recent review, see, e.g., Prusiner, S. B. (2001) New Engl. J. Med. 344, 1516-1526). These neuroinflammation-related disorders include Alzheimer's disease (AD), amyotrophic lateral sclerosis, autoimmune disorders, prion diseases, stroke and traumatic brain injury. Neuroinflammation is brought about by glial (astrocytes and microglia) activation, which normally serves a beneficial role as part of an organism's homeostatic response to injury or developmental change. However, dysregulation of this process through chronic or excessive activation of glia can contribute to the disease process through the increased production of proinflammatory cytokines and chemokines, oxidative stress-related enzymes, acute phase proteins, and various components of the complement cascades. (See, e.g., Akiyama, H., Barger, S., Barnum, S., Bradt, B., Bauer, J., Cole, G. M., Cooper, N. R., Eikelenboom, P., Emmerling, M., Fiebich, B. L., Finch, C. F., Frautschy, S., Griffin, W. S., Hampel, H., Hull, M., Landreth, G., Lue, L., Mrak, R., Mackenzie, I. R., McGeer, P. L., O'Banion, M. K., Pachter, J., Pasinetti, G., Plata-Salaman, C., Rogers, J., Rydel, R., Shen, Y., Streit, W., Strohmeyer, R., Tooyoma, I., Van Muiswinkel, F. L., Veerhuis, R., Walker, D., Webster, S., Wegrzyniak, B., Wenk, G., and Wyss-Coray, T. (2000) Neurobiol. Aging 21, 383-421). The direct linkage of glial activation to the pathology, that is a hallmark of disease, underscores the importance of understanding the signal transduction pathways that mediate these critical glial cellular responses and the discovery of cell permeable ligands that can modulate these disease relevant pathways.

In the case of AD, the deposition of β-amyloid (Aβ) and neurofibrillary tangles is associated with glial activation, neuronal loss and cognitive decline. Id. In terms of molecular mechanisms, there is increased expression of nitric oxide synthase (NOS) in glial cells surrounding the characteristic amyloid plaques; there is neuropathological evidence of peroxynitrite-mediated neuronal damage; and there is evidence that nitric oxide (NO) overproduction is involved in mechanisms of Aβ-induced brain dysfunction. NOSII (iNOS) is induced as part of the glial activation response and is an oxidative stress-related enzyme which generates NO. When NO is present in high levels along with superoxide, the highly reactive NO-derived molecule peroxynitrite is generated, which can lead to neuronal cell death. The proinflammatory cytokine IL-1β is also overexpressed in activated glia in AD brain and polymorphisms in IL-1β genes are associated with an increased risk of early onset sporadic AD (See, e.g., Du, Y., Dodel, R. C., Eastwood, B. J., Bales, K. R., Gao, F., Lohmuller, F., Muller, U., Kurz, A., Zimmer, R., Evans, R. M., Hake, A., Gasser, T., Oertel, W. H., Griffin, W. S. T., Paul, S. M., and Farlow, M. R. (2000) Neurology 55, 480-483), IL-1β can also influence amyloid plaque development and is involved in additional glial inflammatory and neuronal dysfunction responses (See, e.g., Griffin, W. S. T., Sheng, J. G., Royston, M. C., Gentleman, S. M., McKenzie, J. E., Graham, D. I., Roberts, G. W., and Mrak, R. E. (1998) Brain Pathol. 8, 65-72; and Sheng, J. G., Ito, K., Skinner, R. D., Mrak, R. E., Rovnaghi, C. R., Van Eldik, L. J., and Griffin, W. S. T. (1996) Neurobiol. Aging 17, 761-766). These selected examples are part of a large body of evidence accumulated over the past decade that directly links glial activation and specific glial products to neurodegenerative disorders, and raise the possibility that selective modulation of glial activation pathways linked to disease progression might be an area for discovery of new therapies.

A related concern appears to be protein kinase deregulation. Protein kinases are a large family of proteins that play an import role in signalling pathways regulating a number of cellular functions, such as cell growth, differentiation and death. The human genome project has revealed that 20% of the—32,000 human genes encode proteins involved in signal transduction. Among these are more than 500 protein kinases and 130 protein phosphatases exerting tight control on protein phosphorylation. Each protein kinase transfers the γ-phosphate of ATP to a specific residue(s) of a protein substrate. Protein kinases can be further categorized as tyrosine, serine/threonine or dual specific based on acceptor residue. Examples of serine/threonine kinases include MAP kinase, MAPK kinase (MEK), Akt/PKB, Jun kinase (JNK), CDKs, protein kinase A (PKA), protein kinase C (PKC), and calmodulin (CaM)-dependent kinases (CaMKs). A large number of viral oncogenes were found to encode activated protein kinases, implicating deregulated kinases in human cancers. Abnormal protein phosphorylation also underlies many other diseases including diabetes, rheumatoid arthritis and hypertension. Since the hyperactivity of kinases is implicated in disease states, kinase inhibitors could be important therapeutic agents. These inhibitors could be designed to compete either against ATP or the protein substrate.

The potential for modulation of glial inflammatory processes as a therapeutic approach to neurodegenerative disease is indicated by both epidemiological and clinical trial data that show that the use of anti-inflammatory compounds delays onset or slows progression of neurodegenerative changes. Currently, there is a need to develop new classes of chemical compounds capable of inhibiting proinflammatory and oxidative stress related pathways in activated glia as a prelude to searches for new therapeutic approaches. Relevant to this unmet need, through the use of cell-based, high throughput screens (HTS) experimental anti-inflammatory drugs in the family of indolocarbazole alkaloids were found to have a variety of protein kinase inhibitory activities and inhibit NOS and IL-1β production in activated glia. Although the indolocarbazole alkaloid drugs failed as therapeutics due to toxicology, closely related indolocarbazole compounds with more selective kinase inhibitory activity are less toxic and show promise as experimental therapeutics (See, e.g., Maroney, A. C., Finn, J. P., Bozyczko-Coyne, D., O'Kane, T. M., Neff, N. T., Tolkovsky, A. M., Park, D. S., Yun, C., Yan, I., Troy, C. M., and Greene, L. A. (1999) *J. Neurochem.* 73, 1901-1912; and Pirvola, U., Xing-Qun, L., Virkkala, J., Saarma, M., Murakata, C., Camoratto, A. M., Walton, K. M., and Ylikoski, J. (2000) *J. Neurosci.* 20, 43-50). While the effects of these compounds include inhibition of gene regulating protein kinase pathways, a promising target for new anti-inflammatory drug discovery, the indolocarbazole core is not readily amenable to structural diversification of the sort desired for improved formulation properties and minimization of toxicological properties with retention of pharmaceutical effect.

SUMMARY OF THE INVENTION

As discussed briefly, above, a new chemical scaffold with a much simpler structure amenable to in-parallel synthesis approaches and chemical diversification using facile chemistry has been an on-going concern in the art. One aspect of this invention involved a chemical genomics approach followed by a parallel or combinatorial synthesis of a family of compounds tested for their activity in inhibiting target protein kinases and modulating cellular activation or death. A flow sheet of the overall process is shown in Scheme 1, below. A large-scale activity screen was used for chemical scaffolds or starting compounds that have some of the desired activities or functions (step 1). These initial hits are refined in terms of selectivity and affinity by recursive use of high-throughput (combinatorial or parallel) synthetic chemistry and informatics linked to high-throughput activity screens (steps 2-5). Once a set of first-generation compounds are obtained, systematic medicinal chemistry refinement is used on this discrete set of compounds in order to enhance selectivity, affinity, and in vivo behavior.

In the case of kinase inhibition and determinal cellular responses such as excessive glial activation, the refinement of the library screen hits using the modular approach (Scheme 1) with in-parallel syntheses of a number of 3-aminopyridazine derivatives (FIG. 3A) allowed the discovery of a set of starting compounds with the desired selectivity in terms of suppression of kinase activity, glial activation, cell damage, and/or response thereto. For example, the kinase inhibitory activity of one starting compound (steps 1-3 of Scheme 1) is more selective than the prior art compound K252a, an experimental inflammatory drug in the indolocarbazole alkaloid family, while maintaining glial suppression.

For example, the kinase inhibitory activity of an original hit from the chemical library screen (step 1 of Scheme 1) is more selective than the prior art compound K252a, an experimental inflammatory drug in the indolocarbazole alkaloid family, while maintaining glial suppression.

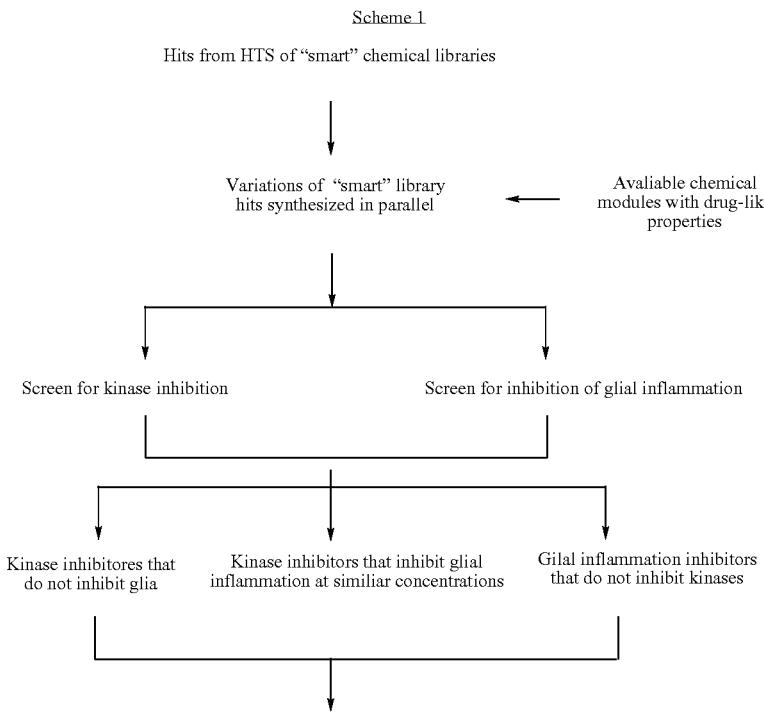

Scheme 1

-continued
First generation compounds for further refinement and study of mechanism
(e.g., virtual screens for new modules & structure assisted design)

Lead compounds for testing in animal models of disease

Pyridazines are pharmacologically attractive scaffolds that have the potential for generating chemically diverse compounds as part of combinatorial or in-parallel syntheses. For example, various pyridazine derivatives display a range of pharmacological activities, including efficacy for drug discovery targets in the brain [Heinisch, G., and Frank, H. (1990) Pharmacologically active pyridazine derivatives. Part 1. *Prog. Med. Chem.* 27, 1-49; Heinisch, G., and Frank, H. (1992) *Prog. Med. Chem.* 29, 141-183; Melikian, G. Schlewer, J. P. Chambon, and C. G. Wermuth. (1992) *J. Med. Chem.* 35, 4092-4097; Saturnino, C., Abarghaz, M., Schmitt, M., Wermuth, C.-G., and Bourguignon, J.-J. (1995) *Heterocycles* 41, 1491-1501].

The chemical and pharmacological properties of pyridazine derivatives made the HTS compound a rational scaffold for diversification by facile chemistries and development of new classes of bioactive compounds capable of selective kinase inhibition and/or modulation of glial responses. This invention, therefore, relates generally to the development of a new class of pyridazine and/or related heterocyclic derivatives, exemplified by a first generation compound, identified as MW01-070C, below, using in-parallel syntheses and a cell-based functional screen with a disease surrogate end point.

For example, and to illustrate the utility of other compositions of this invention, MW01-070C has a much improved ability to inhibit NO accumulation, a biological end point that has been linked to neurological disease and human pathology, compared to currently available drugs that target intracellular signal transduction pathways involved in transcription factor phosphorylation. MW01-070C inhibits NO production in a dose dependent manner through its ability to inhibit iNOS production. MW01-070C also inhibits in a dose dependent manner the production of the proinflammatory cytokine IL-1β. Further, MW01-070C inhibits the increased production of iNOS and IL-1β brought about in response to a variety of disease relevant stimuli, such as Aβ 1-42 peptide, lipopolysaccharide (LPS), and S100B, without diminishing the production of endogenous anti-inflammatory glial proteins, such as apolipoprotein E (apoE), or functionally related response pathways, such as cyclooxygenase (COX)-2 induction. The mechanism of MW01-070C action is clearly distinct from that of currently available inhibitors and experimental therapeutics which target p38MAPK and NFκB, although inhibition of CREB phosphorylation suggests that the theme of targeting gene regulating protein kinases is retained with MW01-070C. The robust, selective activity of MW01-070C, as demonstrated below in comparison with compounds of the prior art, demonstrates the comparative importance of pathways distinct from those directly regulated by MAPK and NFκB, the major focus of current research in the field, and the rapid discovery of new classes of compounds of this invention capable of selective modulation of biological responses provides a proof of principle for the approach.

Accordingly, it is an object of the present invention to provide, in part, to a variety of heterocyclic compositions having utilities including those represented by the pyridazine composition mentioned above. Various other heterocyclic compositions contemplated within the broader aspects of this invention are provided elsewhere herein.

With reference to the following examples and related discussions, it can also be an object of the present invention to provide various methods relating to the modulation of glial activation or phosphorylation pathways and/or new therapeutic routes relating thereto. As illustrated more fully elsewhere herein, such methods include but are not limited to use of the compositions of this invention, preferably in a dose dependent fashion, to selectively inhibit protein kinase activity, glial activation response, oxidative stress-related responses such as nitric oxide synthase production and nitric oxide accumulation, and/or proinflammatory cytokine responses such as interleukin or tumor necrosis factor production. Such methods include, as illustrated below, preparation and/or formulation of an inventive composition with subsequent administration and/or delivery to activated glial cells, tissue, culture or a related physiological system or medium, such administration/delivery in a dose or at a compositional concentration sufficient to effect the desired regulation and/or inhibition, without substantially inhibiting other desired endogenous anti-inflammatory response.

In part, the present invention also relates to the inhibition of neuronal cell death. Selective neuronal cell death is a characteristic feature of the pathology of a number of neurodegenerative diseases, including Alzheimer's disease (AD), traumatic brain injury, and stroke. However, the mechanisms by which neuronal death occurs in these diseases is not well understood. The alteration of protein phosphorylation pathways (protein kinase activity) could potentially be a contributor to disease related neuronal death. Accumulation of abnormally phosphorylated proteins in AD is one disease related example of altered protein phosphorylation pathways, which include the protein kinases and their endogenous protein substrates (Selkoe, D. J., 2001, Physiol. Rev. 81:741-766). Apoptotic cell death has been implicated as one potential mechanism for neuron loss in neurodegenerative diseases. For example, staining for DNA fragmentation by the TUNEL method has revealed considerable TUNEL-positivity in AD brain, but the number of TUNEL-positive neurons is thought to be too high to be compatible with the slow progression of neuronal degeneration seen in AD. However, this histochemical marker has also been found to identify neurons in AD that are more metabolically vulnerable but not necessarily apoptotic. Even though the type of neuronal cell death remains unresolved, a number of different viability assays and cell markers have revealed that neurons are undergoing damaging cellular changes which eventually culminate in synapse loss and neuronal death.

One of the major contributors to the neuronal death in AD is thought to be beta-amyloid (Aβ). Numerous studies have demonstrated that Aβ is toxic to cultured neurons, and an association between amyloid plaque formation and neuronal injury has been reported. Although the mechanisms by which Aβ kills neurons remain incompletely understood, a number of different cell death pathways have been implicated. For example, multiple caspases have been reported to be involved in Aβ-induced neuronal apoptosis, in particular caspase-3 and caspase-8. It has also been hypothesized that terminally differentiated neurons undergo apoptosis when prompted to re-enter an aberrant cell cycle. This mechanism has been suggested in Aβ-induced neuronal death based on observations that Aβ increases levels of the cell cycle checkpoint protein, p53, in neurons, that p53 is increased in AD brain, and that Aβ treatment of neurons can lead to changes in other cell cycle related proteins. It has also been reported (Troy C M, Rabacchi S A, Xu Z, Maroney A C, Connors T J, Shelanski M L and Greene L A (2001) β-amyloid-induced neuronal apoptosis requires c-Jun N-terminal kinase activation. J Neurochem 77: 157-164) that Aβ-induced neuronal cell death requires activation of the MAP kinase, JNK. Some other examples of mechanisms that have been postulated for Aβ-evoked neuronal death include calcium-mediated excitotoxicity, oxidative processes, or toxic interactions with metals.

Although the protein kinases involved in these mechanisms of cell death remain to be identified, calmodulin regulated protein kinases, such as death associated protein kinase (DAPK), are potentially involved based on studies with cell culture and animal models of disease and on the signalling pathways thought to mediate these neurotoxic stimuli effects. For example, in situ hybridization studies in rodent models have shown that DAPK levels are increased after cerebral ischemia (Yamamoto M, Takahashi H, Nakamura T, Hioki T, Nagayama S, Ooashi N, Sun X, Ishii T, Kudo Y, Nakajima-Iijima S, Kimchi A and Uchino S (1999) Developmental changes in distribution of death-associated protein kinase mRNAs. J Neurosci Res 58:674-683), consistent with DAPK's proposed role as an early step in programmed cell death of neurons. However, the identification of the various endogenous protein substrates for DAPK remain to be elucidated. Therefore, with reference to several of the following examples and related discussions, the availability of cell permeable, selective DAPK inhibitors—including compositions of this invention—will facilitate these mechanistic investigations as well as provide new potential therapeutics for treatment of neurodegeneration.

In addition to these direct injurious effects of Aβ on neurons, there is an accumulating body of evidence that supports a cytokine-mediated neuronal cell death in AD and other neurodegenerative disorders. The evidence for the involvement of pro-inflammatory cytokines and NO in neuronal cell death is extensive and has been reviewed recently (Akiyama, H., Barger, S., Barnum, S., Bradt, B., Bauer, J., Cole, G. M., Cooper, N. R., Eikelenboom, P., Emmerling, M., Fiebich, B. L., Finch, C. E., Frautschy, S., Griffin, W. S., Hampel, H., Hull, M., Landreth, G., Lue, L., Mrak, R., Mackenzie, I. R., McGeer, P. L., O'Banion, M. K., Pachter, J., Pasinetti, G., Plata-Salaman, C., Rogers, J., Rydel, R., Shen, Y., Streit, W., Strohmeyer, R., Tooyoma, I., Van Muiswinkel, F. L., Veerhuis, R., Walker, D., Webster, S., Wegrzyniak, B., Wenk, G., and Wyss-Coray, T. (2000) *Neurobiol. Aging* 21, 383-421; Prusiner, S. B. (2001) *New Engl. J. Med.* 344, 1516-1526). However, little is known about the signal transduction pathways and events in the neuron that are critical for translating cytokine signals into neuronal death. Cytokine-induced generation of NO, with subsequent production of peroxynitrite, can lead to neuronal death through nitration of biomolecules. Another mechanism could involve TNFα signaling through the Fas/TNFR family of death receptors, with involvement of caspase-8 and adapter proteins such as FADD. Related to Fas/TNFR signaling, an intriguing possible mechanism for cytokine-induced neuronal death could involve DAPK. As inferred above, DAPK is a multidomain, calmodulin (CaM) regulated serine/threonine protein kinase that has been implicated in apoptosis in peripheral cells and in ischemia-induced neuronal cell death. DAPK has also been found to be important in TNFα- and Fas-induced apoptosis, raising the possibility that it might play a role in the neuronal cell death seen in a variety of neurodegenerative disorders, including AD, stroke, and traumatic brain injury.

There is, therefore, an unmet need for development of inhibitors of DAPK, compounds which would be anticipated to be effective in preventing or reducing the neuronal death seen in neurodegenerative diseases and after brain injury. Pyridazine-based compositions of this invention and related compositions of the type described herein are selective DAPK inhibitors. In particular, reference is made to the composition identified as MW01-026Z, such composition as representative of others of the type described herein showing DAPK inhibition or as can otherwise be utilized in various other methods relating to the inhibition of neuronal cell death—regardless of any downregulation of glial activity. Even so, the present invention provided a structural scaffold on which to base compositions both inhibiting glial activation and DAPK activity.

In part, the present invention also relates to the inhibition of cell death or tissue loss and cell activation in addition to brain glia and neurons. For example, cell activation and tissue damage is a characteristic of other diseases such acute lung injury (ALI). ALI due to sepsis, trauma or mechanical ventilation is associated with high mortality and morbidity, yet there are few effective therapies for the treatment of ALI. ALI is common during sepsis, which itself has an annual mortality equal to acute myocardial infarction. Endothelial cell (EC) dysfunction and activation has been implicated in the in vivo responses linked to ALI, and EC protein kinases, such as myosin light chain kinase (MLCK), have been shown to be critical to EC barrier function and activation. Similarly, the response of the heart to stress and acute injury results in a acute and chronic injuries in which protein phosphorylation regulated pathways and cell activation has been linked to cell death and tissue damage. MLCK and related enzymes such Rho kinase have been implicated in these processes are a logical targets for new therapeutics.

I. Pyridazine and Related Heterocyclic Compositions.

As mentioned above, this invention is, in part, directed to a range of compositions useful in conjunction with the methodologies, disease states and indications described herein. Accordingly, this invention includes but is not limited to an N-heterocyclic composition having the structural formula

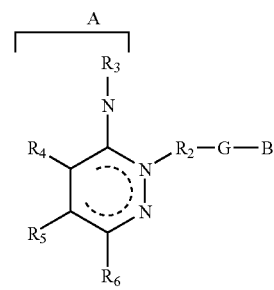

wherein A is a pyridazinyl component and R₃ is a component selected from the group consisting of hydrogen, alkyl and substituted alkyl, phenyl and substituted phenyl, arylalkyl and substituted arylalkyl moieties;

R₄ is a component selected from the group consisting of hydrogen, halogen, alkyl, substituted alkyl, amino, arylalkyl and substituted arylalkyl moieties, phenyl and substituted phenyl moieties, or alkyl and substituted alkyl moieties—as can provide a carbocyclic or heterocyclic moiety with R₅;

R₅ is a component selected from the group consisting of hydrogen, halogen, alkyl, substituted alkyl, phenyl, substituted phenyl, heterocyclic and substituted heterocyclic moieties, arylalkyl and substituted arylalkyl moieties, or alkyl and substituted alkyl moieties—as can provide a carbocyclic or a heterocyclic moiety with R₆;

R₆ is a component selected from the group consisting of hydrogen, halogen, alkyl, substituted alkyl, phenyl, substituted phenyl, heterocyclic and substituted heterocyclic moieties, arylalkyl and substituted arylalkyl moieties, or a substituted phenyl moiety providing a carbocyclic or a heterocyclic moiety with R₅;

R₂ is a divalent component coupling A and G, said component is selected from the group consisting of alkyl, cycloalkyl, acyl, alkylacyl, amido, alkylamido moieties, and further including said moieties having at least one unsaturated carbon-carbon bond sequence;

G is a divalent component coupling R₂ and B, said component selected from the group consisting of alkyl, cycloalkyl, acyl, alkylacyl, alkylamido, urido, sulfonamido, thio, and primary, secondary and tertiary amine moieties; and B is a component selected from the group consisting of hydroxy, amine, substituted amine, arylamine, heteroarylamine, arylalkylamine, hydrazinyl, substituted hydrazinyl, pyrimidinyl and substituted pyrimidinyl, pyridinyl and substituted pyridinyl, pyrazinyl and substituted pyrazinyl, thienyl and substituted thienyl, thiazolyl and substituted thiazolyl, pyrazolyl and substituted pyrazolyl, stilbenzyl and substituted stilbenzyl, imidazolyl and substituted imidazolyl, phthalazine and substituted phthalazine, piperazinyl and substituted piperazinyl moieties.

With respect to valence considerations, the pyridazine-ring-nitrogen at the 1-position can include component R₁ (not shown), a component such as but not limited to hydrogen. Various other moieties can be included, limited only by choice of starting material, synthetic technique en route to the component A and/or modification thereafter.

In various preferred embodiments, R₆ can be but is not limited to halogen (preferably chloride), phenyl and substituted phenyl moieties; R₂ is a (CH₂)ₙ alkyl moiety and n is about 4-12; and G is an acyl moiety where R₆ is phenyl a substituent can be chlorine and said moiety is 4-chlorophenyl. Regardless, B can be selected from the group consisting of piperazinyl and substituted piperazinyl moieties. In certain embodiments, one such piperazine substituent is a pyrimidinyl moiety.

In other preferred embodiments, with regard to component A, R₆ is phenyl and R₅ is an alkyl moiety, (CH₂)ₙ, providing a carbocyclic moiety with the phenyl moiety of R₆; R₂ is a (CH₂)ₙ alkyl moiety and n is about 4-12; G is selected from the group consisting of amido and acyl moieties; and B is selected from the group consisting of pyrimidinyl, substituted pyrimidinyl, piperazinyl and substituted piperazinyl moieties. In several such preferred embodiments, G is an amido moiety and B is a substituted pyrimidinyl moiety. Alternatively, G can be an acyl moiety and B is a substituted piperazinyl moiety.

Various other embodiments of such heterocyclic compositions can be provided with a second pyridazinyl component, B, having the structural formula

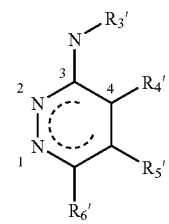

wherein R₃' is a component selected from the group consisting of hydrogen, alkyl and substituted alkyl, phenyl and substituted phenyl, and arylalkyl and substituted arylalkyl moieties;

R₄' is a component selected from the group consisting of hydrogen, halogen, alkyl, substituted alkyl, amino, arylalkyl and substituted arylalkyl moieties, phenyl and substituted phenyl moieties; or alkyl and substituted alkyl moieties as can provide a carbocyclic or a heterocyclic moiety with R₅;

R₅' is a component selected from the group consisting of hydrogen, halogen, alkyl, substituted alkyl, phenyl, substituted phenyl, heterocyclic and substituted heterocyclic moieties, arylalkyl and substituted arylalkyl moieties; or alkyl and substituted alkyl moieties as can provide a carbocyclic or a heterocyclic moiety with R'₆;

R₆' is a component selected from the group consisting of hydrogen, halogen, alkyl, substituted alkyl, phenyl, substituted phenyl, heterocyclic and substituted heterocyclic moieties, arylalkyl and substituted arylalkyl moieties, or a substituted phenyl moiety providing a carbocyclic or a heterocyclic moiety with R'₅;

wherein said second pyridazinyl component is coupled with said G component at one of the said 1-, 2-, 3-nitrogen- and 4-positions thereof.

With regard to several preferred embodiments, component R₆' is phenyl and R₅' is (CH₂)₂ a component providing a carbocyclic moiety with R₆'; and component B is coupled with component G at the 3-amino position thereof. Component G, in turn, can be either an acyl or an amido moiety coupled with R₂. As shown below, such B components are preferably provided with those compositions and structures where R₆ of component A is phenyl and R₅ is carbocyclic therewith.

As discussed and inferred elsewhere herein, it should be understood that, compositionally, the present invention does not include prior art compounds such as 02-10-L-D05. Aside from the evident structural differences, the inhibiting effects observed through use of this invention are surprising, unexpected and contrary to the prior art, as shown below.

A representative, non-exhaustive structural illustration of various A, B and R₂ and/or G moieties is provided, below in Tables 1 and 2.

TABLE 1
Representative Component A and/or Component B Moiety Structures
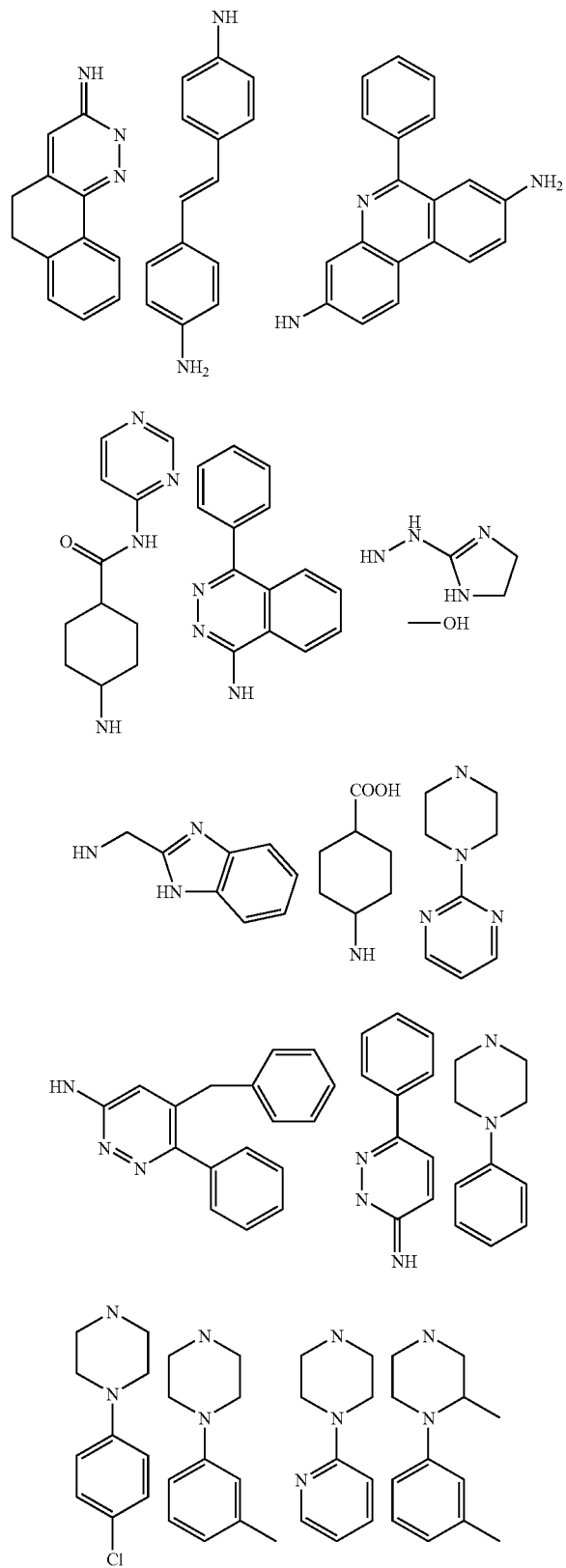
TABLE 1-continued
Representative Component A and/or Component B Moiety Structures
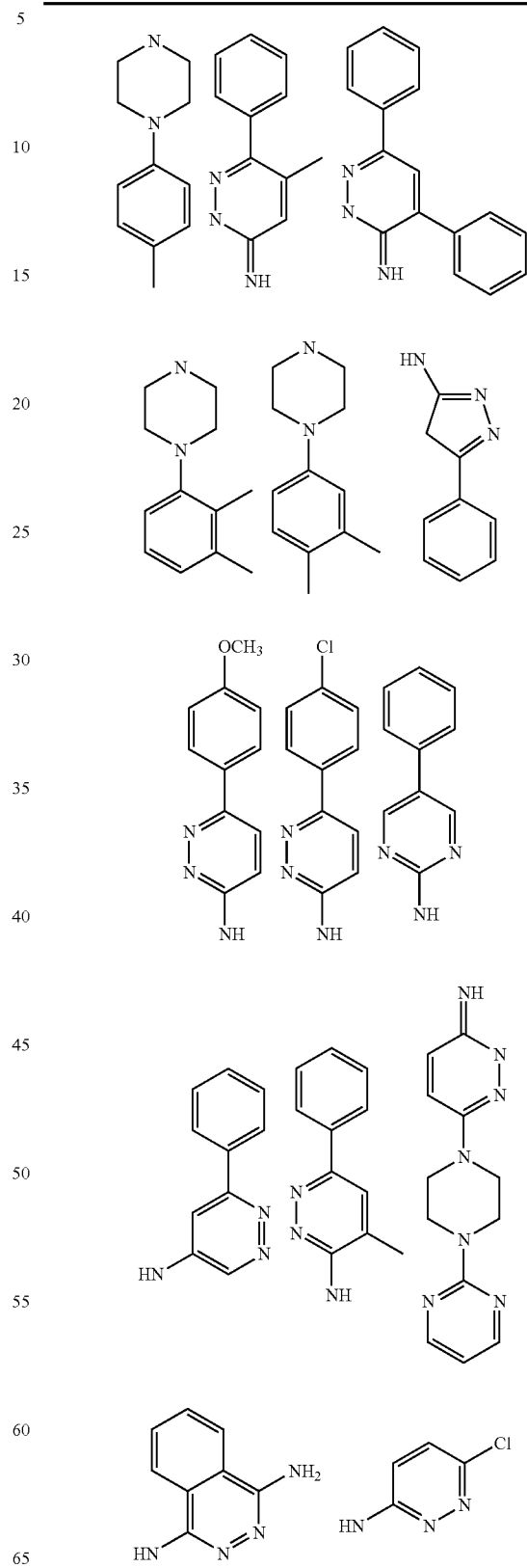

TABLE 1-continued

Representative Component A and/or Component B Moiety Structures

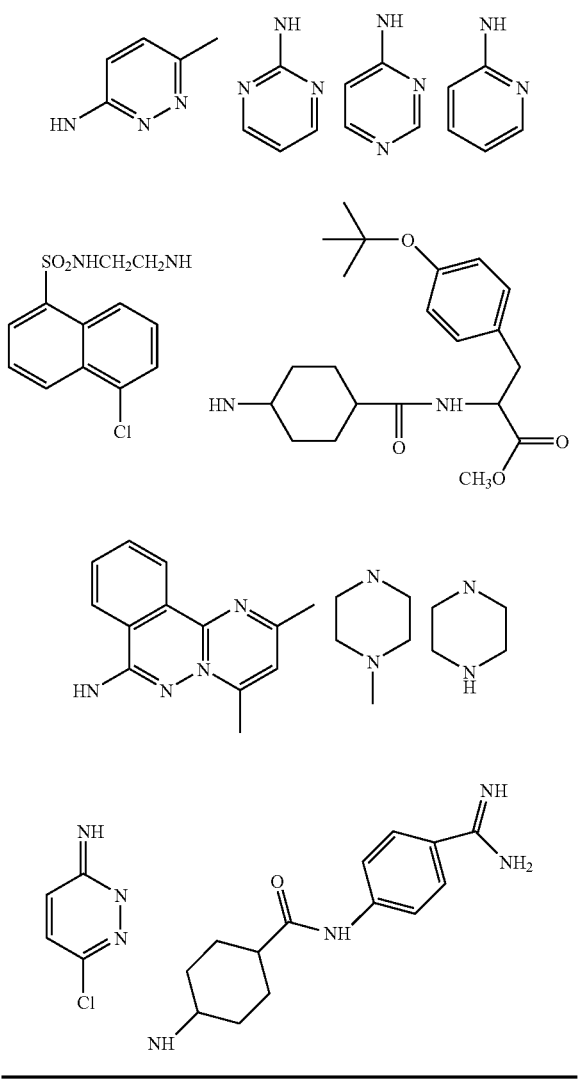

TABLE 2

Representative Component R₂ and/or G Moiety Structures

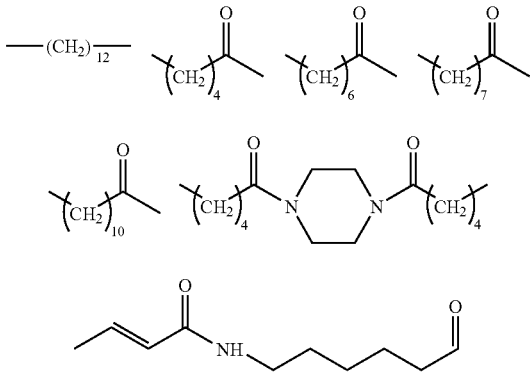

TABLE 2-continued

Representative Component R₂ and/or G Moiety Structures

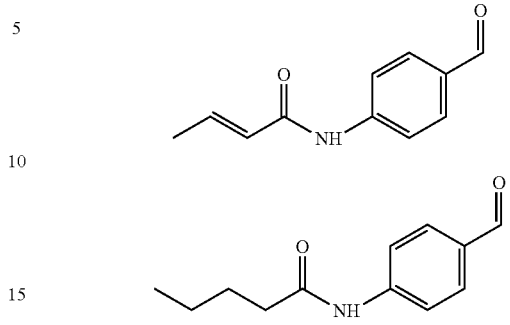

More specifically, with reference to the proceeding and as illustrated in various structures disclosed elsewhere herein, pyridazine component A can be but is not limited to the following: pyridazine, 6-phenyl-pyridazine, 5-methyl-6-phenyl-pyridazine, 4-methyl-6-phenyl-pyridazine, 4,6-diphenyl-pyridazine, 6-(4-chlorophenyl)pyridazine, 4-methyl-pyridazine, 4-chloro-pyridazine, 6[4-(pyrimidinedin-2-yl)piperazine]pyridazine, and 3-(dodecylamino)amino-pyridazine.

Likewise, with reference to the proceeding and as illustrated in various disclosed structures, regardless of any particular component A, component B can be but is not limited to the following: pyridazine, 5-benzyl-6-phenyl-pyridazine, 1-amino-4-phenyl-phthalazine, 1-amino-4-amino-phthalazine, 5-methyl-6-phenyl-pyridazine, 6-phenyl-pyridazine, 4-amino-6-phenyl-pyridazine, 6-(4-methoxyphenyl)-pyridazine, 6-(4-chlorophenyl)-pyridazine, 6-chloro-pyridazine, 6-methyl-pyridazine, 5-phenyl-3H-pyrazol-3-ylamine, 4-(pyrimidinedin-2-yl)piperazine, 4-(pyridin-2-yl)piperazine, 4-phenyl-piperazine, 4-(4-chloro-phenyl)-piperazine, 4-(m-tolyl)piperazine, 4-(p-tolyl)piperazine, 4-(2,3-dimethyl-phenyl)piperazine, 4-(3,4-dimethyl-phenyl)piperazine, 4-methyl-piperazine, piperazine, 2-(5-phenyl)-pyrimidine), 2-pyrimidine, (4,5-dihydro-1H-imidazol-2-yl)-hydrazine, C-(1H-benzimidazol-2-yl)-methylamine, 4-(carboxy)-cyclohexyl amine, 4-aminocyclohexanecarboxylic acid(4-carbamimidoyl-phenyl)-amide, 4'-amino-trans-stilbene, 4-amino-cyclohexanecarboxylic acic pyrimidin-4-yl amide, 6-phenyl-phenanthridine-3,8-diamine, (4-amino-phenyl)-(-4-pyrimidin-2-yl-piperazin-1-yl)-methanone, (4-amino-cyclopent-2-enyl)-(4-pyrimidin-2-yl-piperazin-1-yl)-methanone, 6-amino-1-(4-pyrimidin-2-yl-piperazin-1-yl)-hexan-1-one, and (4-amino-phenyl)-(-4-pyrimidin-2-yl-piperazin-1-yl)-methanone.

Depending on factors such as reagents, choice of starting material and/or synthetic sequence, divalent components $R_2$ and/or G can include $C(O)$, $(CH_2)_{10}$, $(CH_2)_4$ piperazine $C(O)$ $(CH_2)_4$, $(CH_2)_7$, $(CH_2)_{10}CO_2H$, $(CH_2)_4$, $CH_2CH=CH$, $(CH_2)_{12}$ and combinations thereof. For example, regarding the aforementioned dicarbonyl piperazine moiety (cpd MW01-044Z), component $R_2$ can be $(CH_2)_4C(O)$ and the piperazinylalkylketo moiety can be representing component G. Alternatively, with regard to the same dicarbonyl moiety, $R_2$ can be alkyl with component G representing the remainder dicarbonyl structure.

Such components and various others in combination one with another, in accordance with this invention, are provided by way of the following representative, but non-limiting structural formulae, and identified for subsequent reference in the accompanying structure activity relationship tables.

TABLE 3

| SYN. ID | COMPOUNDS |
|---|---|
| MW01-056CHZ | |
| MW01-040D | |
| MW01-060AZ | |
| MW01-060BZ | |
| MW01-060CZ | |

TABLE 3-continued

| SYN. ID | COMPOUNDS |
|---|---|
| MW01-108Z | |
| MW01-097Z | |
| MW01-098Z | |
| MW01-129A | |
| MW01-042GZ | |

TABLE 3-continued

| SYN. ID | COMPOUNDS |
| --- | --- |
| MW01-117Z | |
| MW01-180AZ | |
| MW01-158Z | |
| MW01-038B | |
| MW01-085BZ | |
| MW01-042IZ | |

TABLE 3-continued

| SYN. ID | COMPOUNDS |
|---|---|
| MW01-055V | |
| MW01-044Z | |
| MW01-118Z | |
| MW01-119Z | |

TABLE 3-continued

| SYN. ID | COMPOUNDS |
| --- | --- |
| MW01-053HZ | |
| MW01-008B | |
| MW01-026Z | |
| MW01-059A8Z | |

TABLE 3-continued
| SYN. ID | COMPOUNDS |
|---|---|
| MW01-023BHZ | 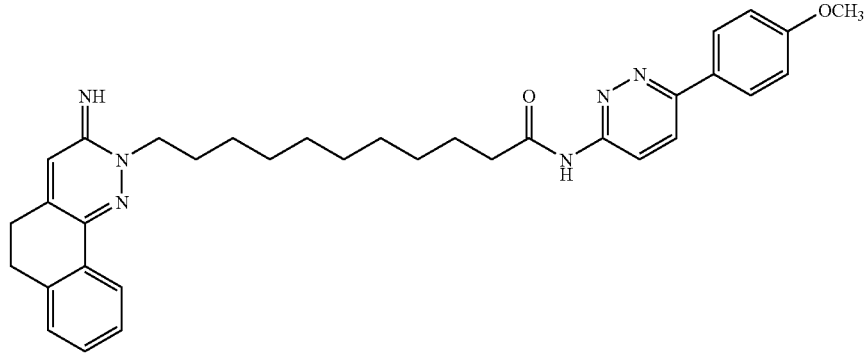 |
| MW01-023CHZ | 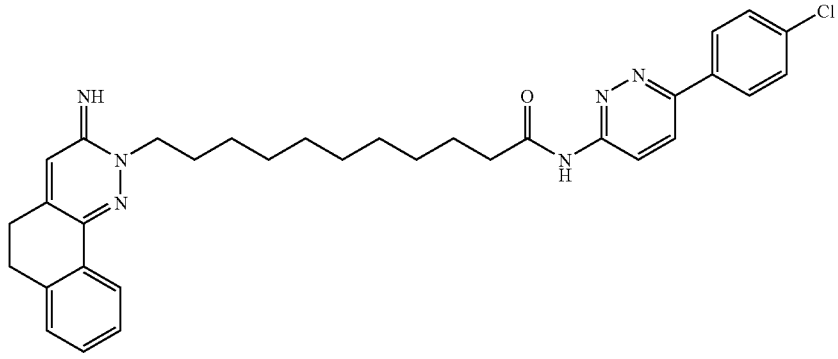 |
| MW01-055HZ | 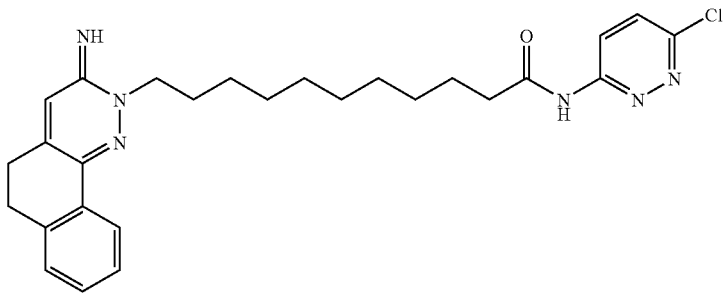 |
| MW01-020B | 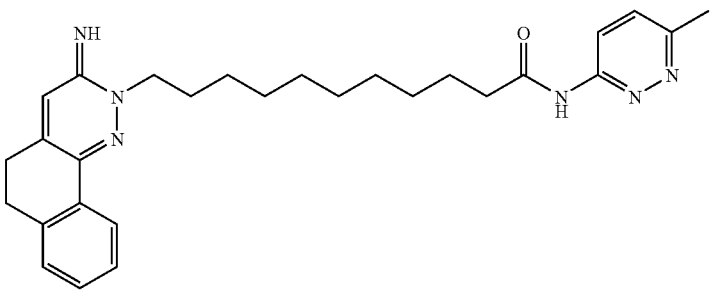 |

TABLE 3-continued
| SYN. ID | COMPOUNDS |
|---|---|
| MW01-022AHZ | 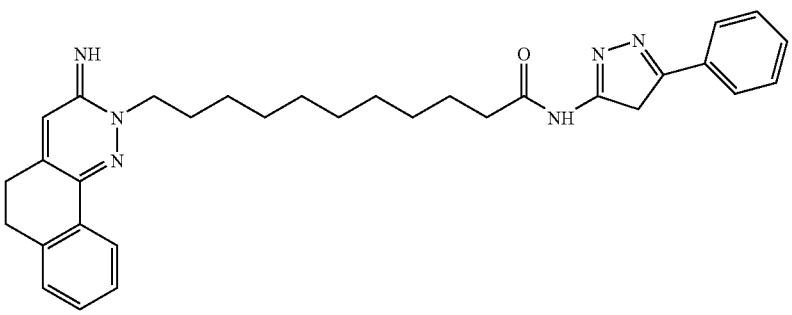 |
| MW01-097B | 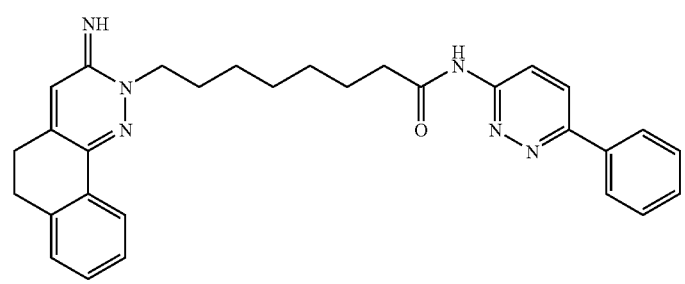 |
| MW01-070C | 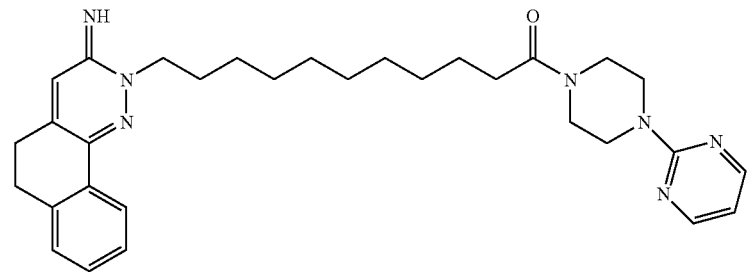 |
| MW01-039D | 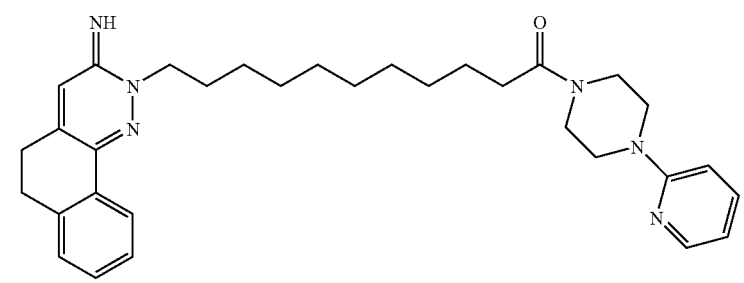 |
| MW01-009D | 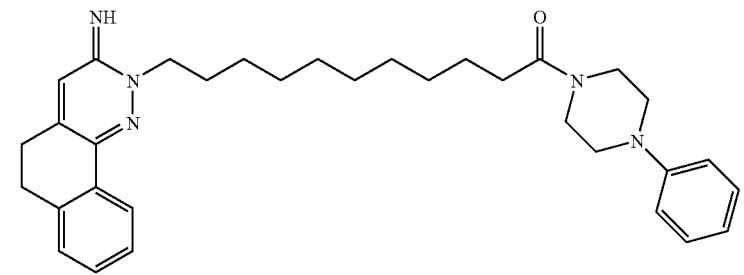 |

TABLE 3-continued

| SYN. ID | COMPOUNDS |
|---|---|
| MW01-023D | *structure: imino-dihydrobenzocinnoline with N-alkyl chain (10 carbons) terminating in acyl-piperazine bearing 4-chlorophenyl* |
| MW01-038D | *structure: imino-dihydrobenzocinnoline with N-alkyl chain terminating in acyl-piperazine bearing 3-methylphenyl* |
| MW01-050AD | *structure: imino-dihydrobenzocinnoline with N-alkyl chain terminating in acyl-piperazine bearing 4-methylphenyl* |
| MW01-050BD | *structure: imino-dihydrobenzocinnoline with N-alkyl chain terminating in acyl-piperazine bearing 2,3-dimethylphenyl* |
| MW01-050CD | *structure: imino-dihydrobenzocinnoline with N-alkyl chain terminating in acyl-piperazine bearing 3,4-dimethylphenyl* |

TABLE 3-continued

| SYN. ID | COMPOUNDS |
|---|---|
| MW01-161AZ | |
| MW01-102Z | |
| MW01-010Z | |
| MW01-051Z | |
| MW01-160Z | |

TABLE 3-continued
| SYN. ID | COMPOUNDS |
|---|---|
| MW01-164BZ | 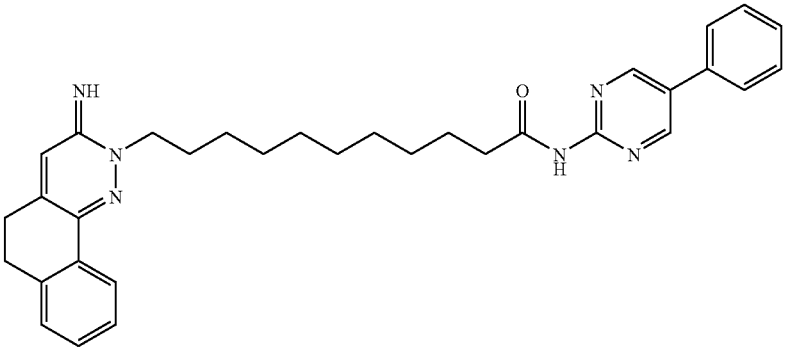 |
| MW01-164DZ | 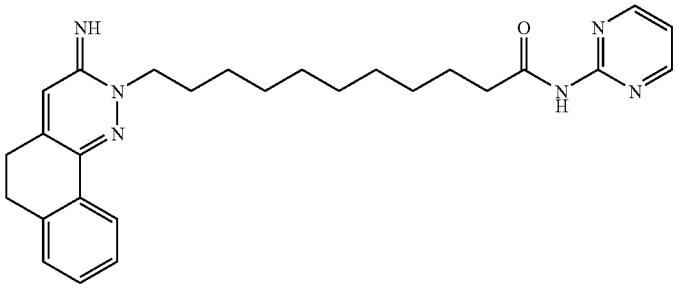 |
| MW01-056-1AV | 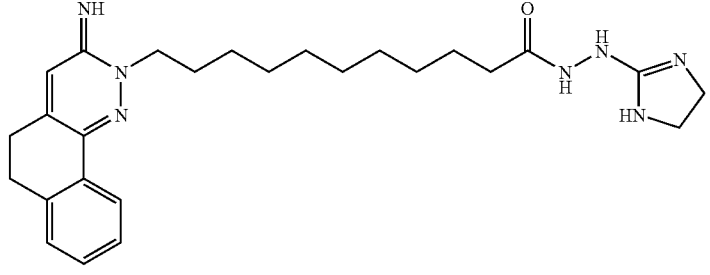 |
| MW01-056-2V | 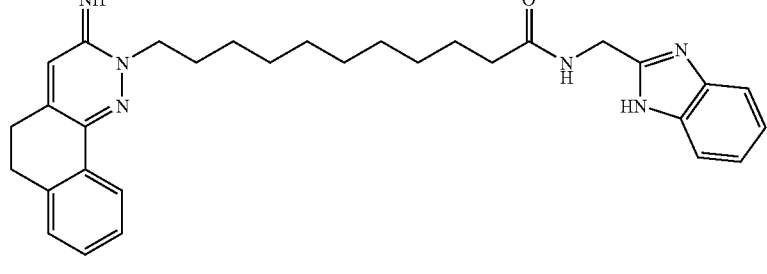 |
| MW01-051V | 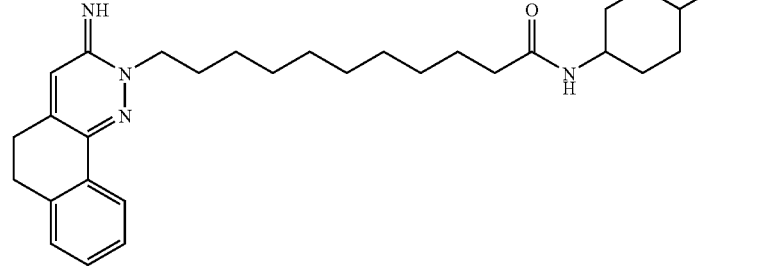 |

TABLE 3-continued

| SYN. ID | COMPOUNDS |
|---|---|
| MW01-070AS | |
| MW01-049HZ | |
| MW01-057D | |
| MW01-008V | |

TABLE 3-continued

| SYN. ID | COMPOUNDS |
| --- | --- |
| MW01-089D | |
| MW01-003B5 | |
| MW01-003DS | |
| MW01-003AS | |

TABLE 3-continued

| SYN. ID | COMPOUNDS |
| --- | --- |
| MW01-003CS | |
| MW01-035CZ | |
| MW01-096CZ | |
| MW01-035AZ | |

TABLE 3-continued

| SYN. ID | COMPOUNDS |
|---|---|
| MW01-035BZ | |
| MW01-125AZ | |
| MW01-086B | |
| MW01-127Z | |
| MW01-161BZ | |

TABLE 3-continued
| SYN. ID | COMPOUNDS |
|---|---|
| MW01-012AZ | 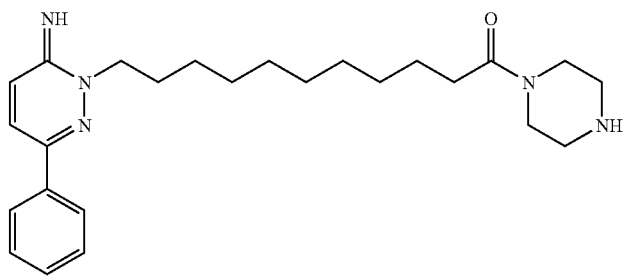 |
| MW01-103B | 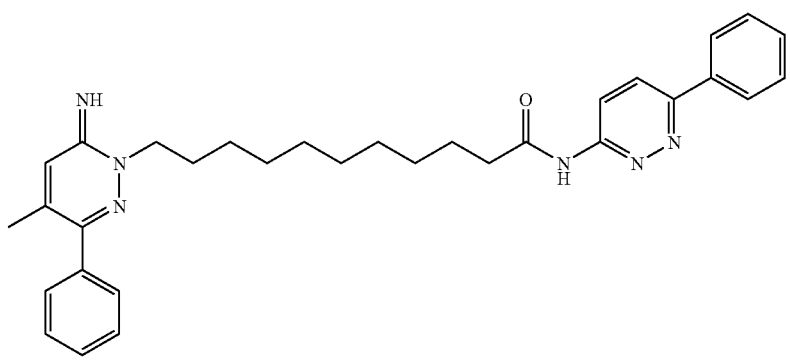 |
| MW01-110B | 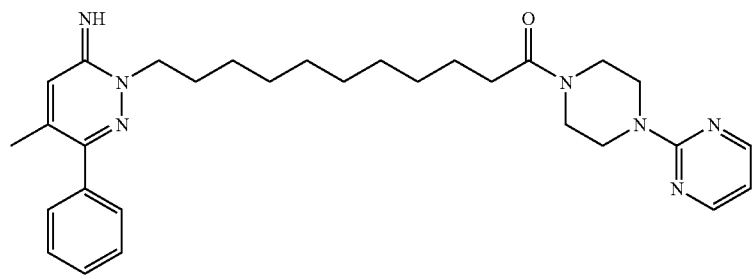 |
| MW01-129B | 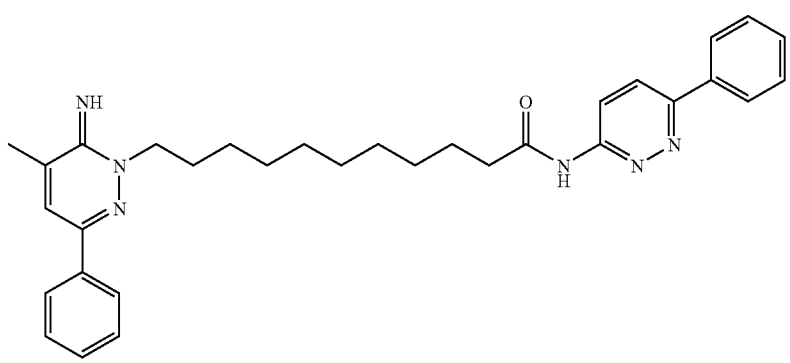 |
| MW01-128B | 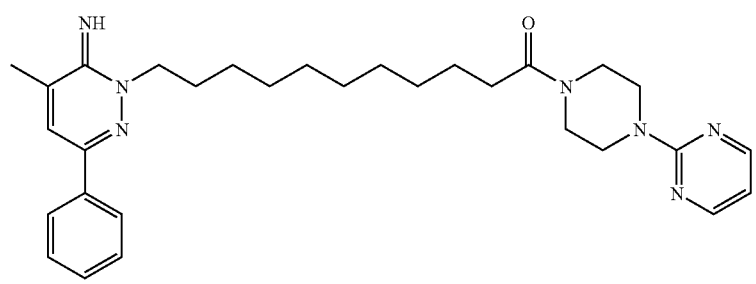 |

TABLE 3-continued
| SYN. ID | COMPOUNDS |
|---|---|
| MW01-021Z | 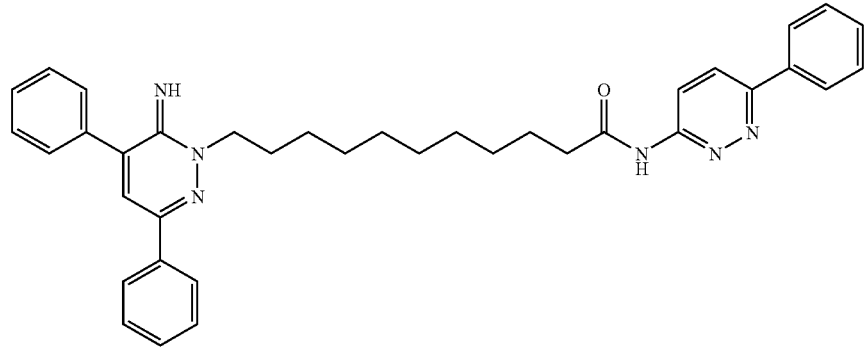 |
| MW01-013Z | 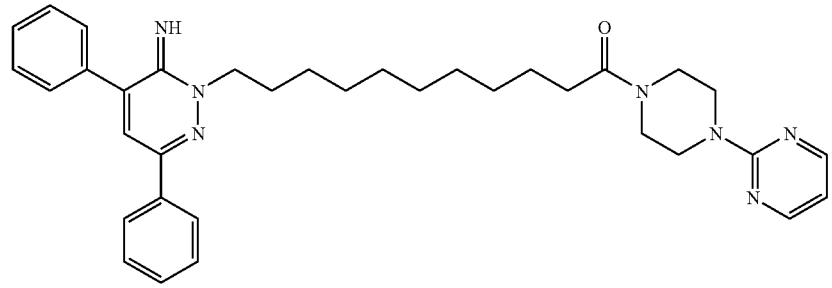 |
| MW01-176AZ | 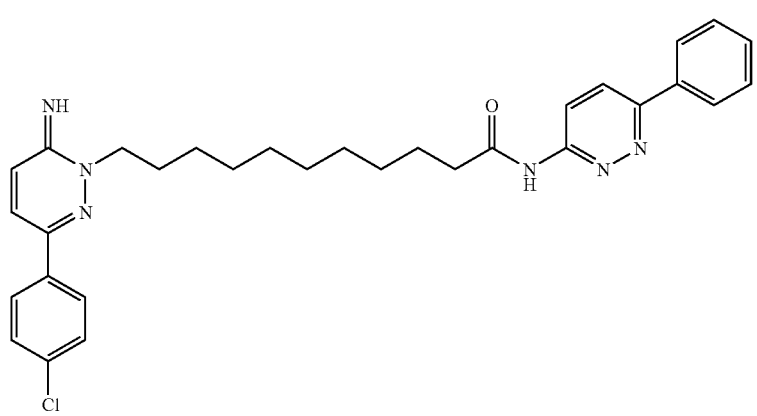 |
| MW01-180AZ | 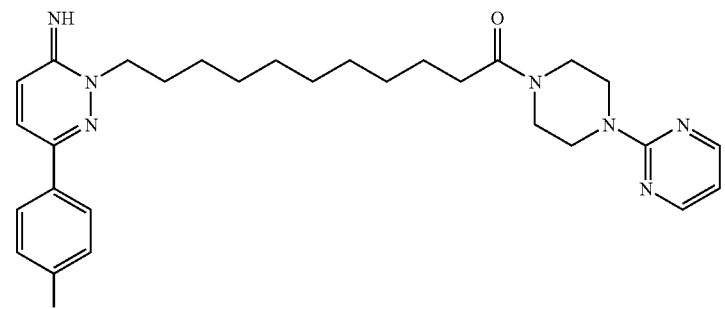 |

TABLE 3-continued

| SYN. ID | COMPOUNDS |
|---|---|
| MW01-031Z | |
| MW01-022AZ | |
| MW01-133Z | |
| MW01-096EZ | |
| MW01-145B1Z | |
| MW01-145B2Z | |
| MW01-024Z | |

TABLE 3-continued

| SYN. ID | COMPOUNDS |
|---|---|
| MW01-196-AS | *(structure: 4-methyl-2-imino-pyridinyl connected via N to a decyl chain ending in C(=O)-piperazinyl-pyrimidin-2-yl)* |
| MW01-070AV | *(structure: 2-imino-5,6-dihydrobenzo[h]cinnolin-1(2H)-yl connected via a decyl chain to N of 3-imino-6-phenyl-pyridazin-2(3H)-yl)* |

As shown above in several tables and examples, numerous compositions of this invention can have a pyridazinyl A component as provided in the structure for compound MW1-070C (2-amino-9,10-dihydro-3-4-diaza-phenanthryl) or compound MW01-031Z (3-amino-pyridazinyl). Variation in structural components/moieties in other compositions having such A components include the following (where component $R_2$ is $(CF_2)_n$ and n=1–~14 and component G is methylene, acyl or amido).

| Component B | B-Substituents |
|---|---|
| 4H-pyrazol-3-yl (G, amido) | 4-Me, Pr, Ph or Cl and/or 5-Me, Ph, Bz, (4-chlorophenyl) or (pyrimidin-2-yl) |
| Pyrimidin-2-yl (G, amido) | 4-Me, Et, Ph, (4-methylphenyl), Cl or (4-chlorophenyl) and/or 5-Me, Et, Bz, Ph, (4-methylphenyl) or (4-chlorophenyl) |
| Piperazin-1-yl (G, acyl or amido) | 3-Me, Et, Pr, Ph or 3-(4-chlorophenyl) and/or 4-Me, Et, Ph, (4-methylphenyl), (3-methylphenyl), (4-chlorophenyl) or (pryimidin-2-yl) |
| Amino (G, methylene or acyl) | Alkyl, substituted alkyl, cycloalkyl, cyclohexyl, substituted cyclohexyl, phenyl, substituted (halo, alkyl, amino alkoxy, or heterocyclic) phenyl, benzyl, substituted benzyl, pyrazolyl, and/or pyrimidinyl |

The same and similar substituents can be employed where the B component is, for instance cyclohex-1-yl(G, amido or acyl) or 3-aminopyridazin-2-yl (G, methylene, acyl or amido). Likewise, any such B components and substituents can be included in those compositions where component A is 3-aminopyridazinyl and $R_6$ is hydrogen, alkyl, substituted alkyl, alkoxy, amine, substituted (alkyl, halo, alkoxy, etc.) phenyl or any one of the number of heterocyclic or substituted heterocyclic moieties shown or referenced elsewhere herein.

Alternatively, given a particular $R_2$ and/or G component, a B component of such compositions can include a hydroxy moiety. Likewise, various other compositions can be prepared wherein the B component is amino, as indicated above. With such compositions, whether part of an amine or amido functionality, the nitrogen thereof can be either mono- or di-substituted. Several such representative substituents are as provided above.

As is evident from the preceding, limited only by starting material, reagent and/or synthetic technique, compositions of this invention can have, depending upon a particular $R_2$ and/or G component, an attenuated moiety coupling components A and B. For example, considering compound reference number MW01-010Z, components $R_2$ and/or G can be varied so as to provide a variety of acid chain links. Similar considerations apply with equal effect to the full range of compositions disclosed herein, regardless of A or B component identities.

Accordingly, the range of compositions encompassed by this invention can be extended to those 3-aminopyridazine structures without ring nitrogen substitution. By way of illustration, consider amino-substituted reference compounds MW01-145BIZ and MW01-145B2Z, both of which are provided above. Without limitation, each composition provides for a coupling component comprising $R_3$, as can be further coupled to a component analogous with the aforementioned G component (e.g., including but not limited to alkyl, acyl, amido, alkylamido, ureido and sulfonamido or as can terminate with a component structurally analogous to an aforementioned B component (e.g., including but not limited to pyridazinyl, aminopyridazinyl and substituted aminopyridazinyl components/moieties). Such compositions are readily obtainable through straight-forward extensions of the synthetic methodologies described herein, as would be understood by those skilled in the art made aware of this invention. Likewise, such individuals would further comprehend that the pyridazine (A) components of such compositions can be substituted as otherwise described herein, and that the corresponding $R_3$ and/or B components can be varied to incorporate a full range of structural and/or functional moieties, in accordance with this invention.

As discussed elsewhere herein, various compositions of this invention can be used to target one or more protein kinases, the high resolution crystal structures of which can be used to further the design, development and/or modification of the present compositions. Without limitation to any one theory or mode of operation, it is believed that component A of the present compositions can occupy the ATP binding site of such enzymes. Modification of and/or adding molecular structure to component A can enhance ATP site binding, as well as extend occupation to the tri-phosphate tunnel of such enzyme structures—presumably to increase selectivity with retention of affinity. As such several other structural variations can be employed, including but not limited to, those piperazine and aminopyridine compositions referenced herein as MW01-024Z and MW01-196AS, respectively.

The compositions of this invention demonstrate utility in a number of pharmaceutical contexts by way of related methodologies. Representative in vitro results can be reasonably correlated with a range of in vivo activities, as would be understood by those skilled in the art. Likewise, various methodologies of this invention are demonstrated in vivo, the results of which are reasonably indicative of corresponding therapeutic use. For example, as explained more thoroughly below, in vivo protein kinase inhibition was demonstrated at dosage/concentration levels clinically relevant to and comparable with levels used with prior art kinase inhibitor therapeutics in other disease areas. Accordingly, the compositions of this invention can be used to modulate glial cell activation response, reduce nitric oxide production, inhibit cellular apoptosis and/or death associated protein kinase activity and, without limitation, to reduce injury from hypoxia-ischemia, acute lung injury and/or endothelial cell dysfunction in lung or vascular tissue.

As such, the present invention also provides a variety of pharmaceutical preparations comprising a pyridazinyl composition of this invention in conjunction with a physiologically or otherwise suitable formulation. In a preferred embodiment, one or more of the present compositions is formulated together with one or more non-toxic physiologically tolerable or acceptable diluents, carriers, adjuvants or vehicles otherwise known to those skilled in the art for parenteral injection, oraficial administration in solid and liquid form, topical administration, or the like. The resulting formulations can be, in conjunction with the various methods described herein, administered as would be understood by those skilled in the art, including but not limited to a variety of parenteral or intraperitoneal techniques.

As provided more fully in the descriptions and examples, to follow, the compositions of this invention find utility in the treatment of various related disease states, as illustrated elsewhere herein with numerous representative embodiments. A non-exhaustive list is provided in Table 4, below.

TABLE 4

| | Representative Compositions |
|---|---|
| Dementing/Neurodegenerative Disorders | |
| Alzheimer's disease and related disorders | MW01-070C |
| Pick's disease | MW01-026Z |
| Progressive supranuclear palsy | |
| Multiple system atrophies | |
| Tauopathies | |
| Vascular dementia | |
| AIDS-related dementia | |
| Down syndrome | |
| Stroke and related cerebrovascular disorders | |
| Hypoxia, ischemia, infarction, intracerebral hemorrhage | |
| Parkinson's disease | |
| Meningitic syndromes: bacterial, fungal, parasitic and viral meningitis | |
| Traumatic brain injury/head trauma | |
| Epilepsy syndromes, such as Status epilepticus | |

TABLE 4-continued

| | Representative Compositions |
|---|---|
| CNS Demyelinating/Autoimmune disorders | |
| Multiple sclerosis | MW01-070C |
| Optic neuritis | MW01-026Z |
| Guillain-Barre syndrome | |
| Chronic inflammatory demyelinating polyneuropathy | |
| Acute disseminated encephalomyelitis (ADEM) | |
| Autoimmune inner ear disease (AIED) | |
| Peripheral inflammatory diseases | |
| Diabetes (diabetic neuropathy) | MW01-070C |
| Myocardial ischemia and other cardiovascular disorders | MW01-026Z |
| Pancreatitis | MW01-022AZ |
| Gout | |
| Inflammatory bowel disease: ulcerative colitis, Crohn's disease | |
| Rheumatoid arthritis | |
| Osteoarthritis | |
| Spondyloarthropathies: ankylosing spondylitis, psoriatic arthritis | |
| Systemic lupus erythematosus | |
| Progressive systemic sclerosis or scleroderma | |
| Inflammatory myopathies: dermatomyositis, idiopathic polymyositis | |
| Bacterially induced lung injury | |
| Septic shock, Toxic shock syndrome | |
| Asthma | |

IIA. Antineuroinflammatory Effects.

Several figures relate more specifically to the following descriptions and examples.

FIG. 1. Cell-based screen for inhibition of LPS-stimulated NO release. BV-2 microglial cells were incubated with LPS in the presence of increasing concentrations of compounds 1-9, and accumulation of NO in conditioned media was determined. Inhibition is expressed as percent control, where the control is the NO accumulation from cells stimulated with LPS alone.

FIG. 2. Selective effects of compound 1 (MW01-070C) on glial activation responses and gene-regulating protein kinase pathways. BV-2 cells and rat astrocytes were treated with control buffer (C) or stimulated with LPS or Aβ1-42 peptide in the presence or absence of compound 1, and cell lysates were analyzed by Western blots. (A) Astrocytes treated with LPS and compound 1 show concentration-dependent inhibition of iNOS and IL-1β production but not GFAP. (B) Astrocytes treated with A β1-42 and compound 1 (10 μM) show inhibition of iNOS and IL-1β but not apoE and COX-2. (C) BV-2 cells treated with LPS and compound 1 (10 μM) show inhibition of phosphorylated (p-) CREB but not p-p38 and p-ATF2, as assayed with antibodies that are specific for the phosphorylated forms of the proteins. Data are expressed as percent control (mean±SD; n=3 determinations). The right panel shows a representative blot.

In accordance with the compositional aspects of this invention, a number of alkylated 3-amino pyridazine derivatives (compound 1 in chart 1, and reference no. MW01-070C, in Table 3, above) were shown to selectively block the production of IL-1β, iNOS, and NO by activated glia. Remarkably, the inhibitor exerts its desired effects without diminishing the production of endogenous antiinflammatory glial proteins, such as apolipoprotein E (apoE), or functionally related response pathways, such as cyclooxygenase (COX)-2 induction. The mechanism of action of the inhibitor is believed clearly distinct from that of currently available inhibitors, which target p38 MAP kinase (MAPK), an enzyme that is important in peripheral inflammation. Although the mechanism of action of compound 1 (MW01-070C) remains to be established, the results suggest CaMK-dependent pathways as potential targets.

The compounds shown below were made by standard procedures from commercially available starting materials and precursors described in the literature or were obtained commercially. The reaction scheme for the parallel synthesis of selected pyridazine derivatives (compounds 1-4, below) is shown in conjunction with example 1 (Scheme 2). Briefly, the 3-amino-6-phenylpyridazine was prepared from the corresponding chloropyridazine derivative, which was converted to the hydrazine derivative by refluxing with aqueous hydrazine. The hydrazine derivative was reduced to the 3-amino-6-phenylpyridazine by reduction with hydrogen over a nickel-aluminum alloy catalyst. The intermediate 3-amino-6-phenylpyridazines alkylated at ring nitrogen 2 and the deprotection of the carboxylic acid were prepared by standard procedures, with typical conditions given in the footnote to Scheme 2. For comparison purposes, the commercially available inhibitors, compounds 5-9, below, were chosen on the basis of their selectivity for inhibiting various signal transduction pathways that converge on the regulation of IL-1β and iNOS expression.

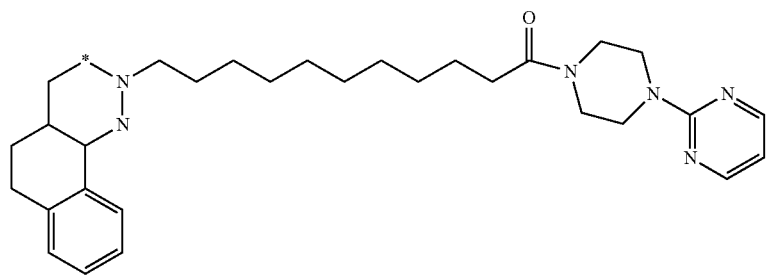

1

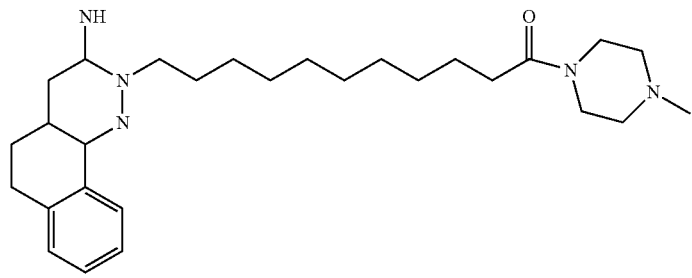

2

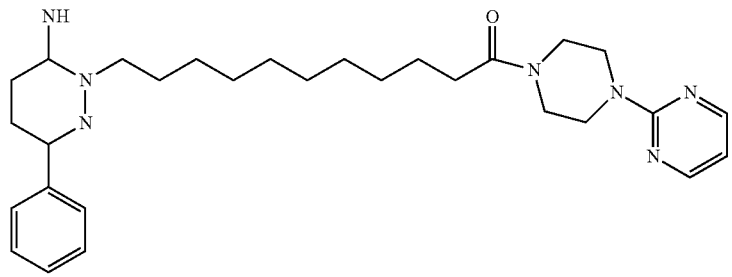

3

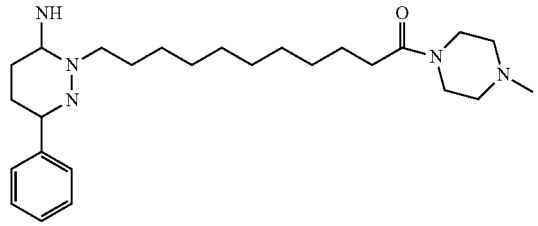

4

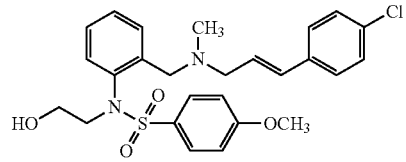

5

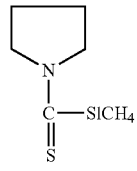

6

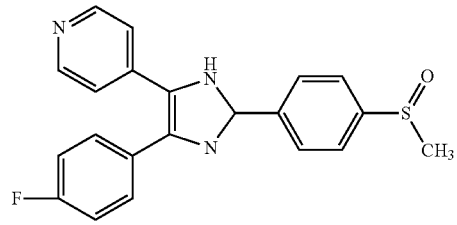

7

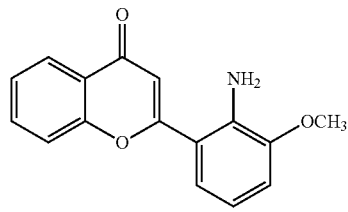

8

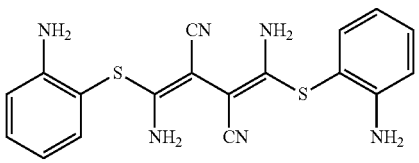

9

Glial cells were maintained and treated as with one of two activating stimuli: bacterial endotoxin (lipopolysaccharide LPS)) or Aβ1-42 peptide. Compounds were tested for their concentration-dependent effects on NO accumulation in conditioned media, and proteins were detected by Western blots. Reconstituted enzyme assays were done as described in the accompanying examples.

The quantitative ability of the compounds to inhibit NO accumulation, a disease-linked surrogate end point, by activated glia is shown in FIG. 1. The cell-based activity screen showed that compound 1 (MW01-070C), was the most active compound. The amine, 1-(2-pyrimidyl)piperazine, used in the production of compound 1 was one of several found in a structure-based search of the available chemicals database for aromatic heterocylic compounds, with prioritization of choices for inclusion in parallel syntheses based on use in the synthesis of other drug-like compounds. The 1-(2-pyrimidyl) piperazine is present in various CNS active compounds and is thought to be an important contributor to the pharmacology of the clinically effective drugs of which it is a component. Although the 1-(2-pyrimidyl)piperazine was chosen for its prior use in CNS-active drugs, the comparative results obtained with compounds 2 (MW01-161AZ) and 4 (MW01-161BZ) show that the characteristic aromatic ring associated with its pharmacological activity with other CNS targets is not required for inhibition of glial activation in the cell-based assay. The presence of an aromatic ring, however, resulted in the best cellular activity. Synthetic precursors shown in Scheme 2 were inactive. Overall, the results indicate that the contribution of the pyridazine and piperazine to activity is context-dependent.

The cell-based assay results for compounds 5-9 (FIG. 1) allow a tentative ranking of the quantitative importance of various gene-regulating protein kinase pathways that converge on a common biological end point. For example, compounds 5 (KN93), 6 (PDTC), 7 (SB203580), 8 (PD98059), and 9 (U0126) are inhibitors of CaMKII, NF$_K$B, p38 MAPK, and MEK1/2 signaling pathways, respectively, and each of these distinct intracellular signal transduction pathways converges at the level of transcription regulation in glial activation. However, the NF$_K$B, p38 MAPK, and MEK1/2 inhibitors are less effective (FIG. 1) than compound 1 or 5 (KN93), a widely used CaMKII-selective inhibitor. Overall, the results are consistent with all of these pathways contributing to NO production. However, the relative importance of p38 MAPK mediated pathways to the end point in glia might be less than previously thought from studies of peripheral tissues.

To confirm that compound 1 does not target p38 MAPK and to examine its potential selectivity for CaMKII, the ability compound I was examined in reconstituted enzyme assays to inhibit several relevant protein kinases key to the intracellular pathways that converge on iNOS and IL-1β gene expression. As shown in Table 1, compound 1 does not inhibit p38 MAPK activity up to the highest concentration of compound tested (100 μM). In contrast, compound 1 inhibits CaMKII activity at concentrations similar to that of compound 5, the current standard in the field. Compound 1 also does not inhibit the closely related CaM regulated protein kinase, myosin light chain kinase (MLCK), or other second messenger signal transducing kinases, such as protein kinase A (PKA) and protein kinase C (PKC). Clearly, derivatives of compound 1 have the potential to provide more selective small-molecule inhibitors of CaMKs as well as new antineuroinflammatory compounds.

TABLE 5

Selective Inhibition of Protein Kinase Activity[a]

| | IC$_{50}$ (μM) | | | | |
|---|---|---|---|---|---|
| Compd | CaMKII | p38 MAPK | MLCK | PKC | PKA |
| 1 | 9.7 ± 1.9 | >100 | >100 | >100 | >100 |
| 5 | 8.4 ± 1.0 | >100 | 9.8 ± 0.7 | >100 | >100 |

[a]Enzyme assays were done using y-[$^{32}$P]-ATP and synthetic peptide substrates. IC$_{50}$ values were calculated from the linear part of inhibition curves and represent the mean ± SEM obtained from at least two different experiments.

The comparatively robust effect of compound 1 prompted an examination of its selectivity on various glial activation responses. FIG. 2A shows that compound 1 inhibits both IL-1β and iNOS production. The levels of the astrocyte marker protein, glial fibrillary acidic protein (GFAP), are not changed. The GFAP results provide a biological response control to demonstrate that compound 1 is not a general protein synthesis inhibitor and not cytotoxic under the assay conditions. Compound 1 also inhibits (FIG. 2B) iNOS and IL-1β production in glia stimulated by Aβ1-42, a peptide that is involved as an initiating event in models of AD pathogenesis. In terms of selectivity for activation responses, there was no effect of compound 1 on the levels of COX-2, an inflammatory response enzyme that is also increased in activated glia, and no effect on the production of apoE, an endogenous antiinflammatory protein (FIG. 2B).

The concentration-dependent effect (FIG. 2A) of compound 1 on iNOS and IL-1β levels, its ability to suppress the production of selected disease-linked end points in response to multiple activating stimuli (FIG. 2B), and its robust activity with a quantifiable end point (FIG. 1) raise the possibility that compound 1 works at a late step in intracellular signal transduction pathways, where multiple, interacting pathways are known to converge on common biological end points such as iNOS and IL-1β gene regulation. In addition, previous results have shown that antiinflammatory drugs that block NO production can inhibit the phosphorylation of transcription factors such as CREB, a substrate of CaMKII isoforms that are capable of nuclear localization. As shown in FIG. 2C, compound 1 inhibits the increased phosphorylation of CREB, but does not inhibit the increase in phosphorylated ATF2 (an endogenous p38 MAPK substrate) or the upstream increase in phosphorylated p38 MAPK itself (FIG. 2C). These results demonstrate that the p38 MAPK pathway is activated in these cells, as expected, but there is no detectable down modulation of the pathway by compound 1. The inhibition of CREB phosphorylation is consistent with the inhibition of one of its upstream kinases, such as CaMKII. Regardless of the details of mechanism, the effects of compound 1 fit the redundant paradigm of inhibition of transcription factor phosphorylation as a mechanism for antiinflammatory action. In the case of joint inflammation, the p38 MAPK pathway is quantitatively important and a viable target for drug discovery, whereas our results raise the possibility that other kinase-mediated pathways might be more viable targets for the CNS.

Compound 1 has key features that are attractive in early-generation compounds. These include its selective targeting of steps in the glial activation loop that are disease-linked without perturbation of related pathways. In addition, compound 1 does not target the same regulatory pathways that can be critical in peripheral inflammatory responses. This raises the possibility that future refinements of compound 1 structure and activity might allow avoidance of undesired side effects such as suppression of peripheral inflammatory responses. Finally, pyridazines are attractive starting points for future refinement because they have the potential for generating chemically diverse compounds as part of in-parallel syntheses, and slight modifications result in a range of pharmacological activities.

EXAMPLE 1

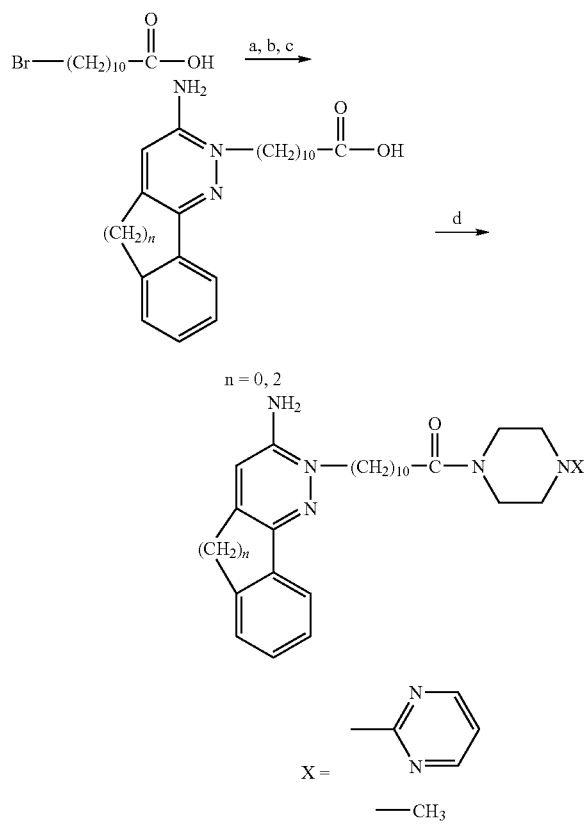

a Reagents and conditions: (a) EtOH, 1 equiv of 4 N HCl, 48 h, 95%;
(b) 0.75 equiv of 3-aminopyridazine compound, DMF, 80° C., 94%;
(c) 20% concentrated HCl in AcOH, 90° C., 10 h, 90%;
(d) 1 equiv of 1-(2-pyrimidyl) piperazine or 1-methylpiperazine, HOW EDC, DMF, 0-22° C., 21 h, 60-98%.

Compounds 1-4 (MW01-070C, MW0-161AZ, MW0-127Z and MW0-161BZ, respectively, in Table 3) were synthesized following the protocol shown in Scheme 2, above, from commercially available materials and precursors prepared as described elsewhere herein. Commercially available 11-bromoundecanoic acid (Aldrich) was dissolved in ethanol and one equivalent of 4N HCl in dioxane (Aldrich), and the mixture allowed to react for upwards of 45 hrs at ambient temperature (20-22° C.). The solvent was removed under reduced pressure and the crude residue was washed twice with hexane, and dried under vacuum. The resulting bromoethyl esters were dissolved in dimethylformamide (DMF; Allied Signal) and processed as above, in Scheme 2, steps a,b. Additional DMF was added as needed, in the first 2 hrs to re-suspend any precipitants formed during the reaction. The extent of reactions was monitored by analytical HPLC (Rainin Instruments, Woburn, Mass.) on a commercially available (Phenomenex, Torrance, Calif.) reverse phase column (C5, 5μ). Eluents (A): 0.1% (v/v) TFA in water and (B): 80% (v/v): acetonitrile/water containing 0.09% TFA were used with a⁻ linear gradient of 100/0 to 0/100 A/B over 22 min at 1 mL/min. The reaction mixtures were precipitated with ethyl ether and collected by filtration, washed with ethyl ether and dried under vacuum. The products were obtained as granular powders. The resulting esters containing the 3-amino-6-phenylpyridazine module were added to glacial acetic acid and 12 N HCl, and were refluxed at 90° C. for 10 hrs. The reactions were monitored by analytical HPLC as described above. The products were precipitated in ethyl ether, filtered, washed with ethyl ether and dried under vacuum. After the alkylated 3-amino-6-phenylpyridazine derivatives were dissolved in a minimal amount of DMF, activation of the carboxylic acids took place by addition of 1 equivalent of 1-hydroxybenzotriazole (HOBt: Pierce Chemicals) and 1.1 equivalents of 1-ethyl-3(3-dimethyl-aminopropyl)carbodiimide (EDC; Aldrich) at 0° C. for 1 h. Then, 1 equivalent of 1-(2-pyrimidyl) piperazine dihydrochloride or 1-methyl-piperazine (Aldrich) was added to the reaction mixture (step d). When necessary, the pH was adjusted to 5-6 with DIEA. The extent of reactions was monitored by analytical HPLC as described above. The reaction mixtures were precipitated with ethyl ether and filtered on a medium pore glass filter under vacuum. The precipitates containing compounds 1-4 were dried in vacuo. Compounds 1-4 were further purified by HPLC (Rainin Instruments, Woburn, Mass.) on a preparative (Microsorb, Woburn, Mass.) reverse phase column (CIS). Eluents (A): 0.1% (v/v) TFA in water and (B): 80% (v/v) acetonitrile/water containing 0.08% TFA were used with a linear gradient of 50/50 to 0/100 A/B over 28 min at 8 mL/min for Compounds 1 and 3, and a linear gradient of 70/30 to 20/80 A/B for Compounds 2 and 4.

Purity of all synthetic compounds was checked by analytical HPLC using a Rainin Instruments System (Woburn, Mass.). Two different commercially available reverse phase columns were used for analysis of compounds 1-4: C5 (5μ) Phenomenex (Torrance, Calif.) and C18 (5μ) Microsorb (Woburn, Mass.). Eluents were (A): 0.1% (v/v) TFA in water and (B) 80% (v/y) acetonitrile/water containing 0.08% TFA. A linear gradient of 100/0 to 0/100 A/B over 22 min. at 1 mL/min was used.

The HPLC traces for all compounds for each condition are shown below. Masses were determined by matrix-assisted laser-desorption mass spectrometry (MALDI-TOF MS) using a PerSeptives (Foster City, Calif.) Voyager DE-Pro system and are presented in tabular form below. Elemental analysis of compound 1 was performed by Oneida Research Services, Inc. (Whitesboro, N.Y.), and NMR analysis was done by Acorn NMR (Livermore, Calif.) and the data are presented in the text.

Elemental analysis of compound 1 (MW01-070C) gave the following: C, 54.87; H, 5.84; N, 12.43. Expected for $C_{31}H_{41}N_7O.2TFA$ was the following: C, 55.62; H, 5.73; N, 12.97. The mass was 528.6 (expected, 528.3). NMR analysis of compound 1 was consistent with the structure. $^1H$ NMR (CD$_3$OD); δ 1.4 (s, 16H), 1.98 (t, 2H), 2.41-2.44 (t, 2H), 3.03-3.06 (d d, 4H), 3.67-3.74 (t, 4H), 3.82-3.92 (d d 4H), 6.82 (t, 1H), 7.34 (t, 1H), 7.35-7.60 (m, 3H), 8.2 (d, 1H), 8.47-8.49 (d, 2H). MALDI-TOF MS Data for Compounds 2-4

|  | Compound 2 | Compound 3 | Compound 4 |
| --- | --- | --- | --- |
| Expected Mass | 464.3 | 502.3 | 438.3 |
| Observed Mass | 464.6 | 502.8 | 438.5 |

EXAMPLE 2

The murine microglial BV-2 cell line and primary rat cortical glia were maintained and treated with the activating stimuli LPS (100-500 ng/ml) or Aβ 1-42 peptide (10 µM) for 24 hrs in the presence or absence of compounds 1-9 as described previously. The rationale for using BV-2 cells in high throughput screening was the paucity of well-characterized human microglial cell lines, and the relevant activation responses and signaling pathways reflect those seen in human and rodent primary microglial cultures. Compounds were tested for their effects on NO accumulation in conditioned media of LPS-stimulated BV-2 cells by measurement of nitrite production by the Griess assay as a read-out for iNOS activity, as described previously. Stock solutions of compounds were prepared in dimethylsulfoxide (DMSO) or in water. When stock solutions were prepared in DMSO, control wells contained the same final concentration of DMSO as the compound-containing wells. In all cases, the final DMSO concentration did not exceed 0.1%. Solutions of compounds for cell treatments were diluted to a 10× final concentration by dilution of stock solutions in αMEM media. The commercially available drugs tested were: compound 5 (KN93 from Alexis); compound 6 (pyrrolidinedithiocarbamate or PDTC from Sigma), compound 7 (SB203580 from Alexis Corporation), compound 8 (PD98059 from Alexis Corporation), and compound 9 (U0126 from Cell Signaling). SB203580, U0126 and PD98059, PDTC, and KN93 are used as pathway-selective inhibitors of p38 MAPK, MEK1/2, NFκB, and CaMKII signaling pathways. Respectively, Western blots of cell lysates were done with the following antibodies: monoclonal anti-iNOS (1:1000 dilution, Transduction Labs); polyclonal anti-rat IL-1β (1:1000 dilution, R&D Systems, Inc.); monoclonal anti-glial fibrillary acidic protein (GFAP) (1:10$^8$ dilution, Sigma); polyclonal anti-rat alioE (1:15,000 dilution) prepared as described; polyclonal anti-COX-2 (1:500 dilution) and monoclonal anti-phosphoATF2 (1:1000 dilution) from Santa Cruz Biotechnology; polyclonal anti-phospho-CREB (1:1000 dilution), and polyclonal anti-phosphop38 MAPK (1:1000 dilution). Reconstituted enzyme assays were done as described s. The sources of protein kinases were: bovine heart PKA from Promega, rat brain PKC from Calbiochem, rat CaMKII from New England Biolabs, chicken gizzard MLCK prepared as described, and a p38 MAP kinase kit containing recombinant Xenopus p38-MAPK and its human substrate from Upstate Biotechnology. The catalytic domains of these protein kinases retain a high level of amino acid sequence identity across mammalian species, consistent with the lack of documented major differences across species for the in vitro catalytic activity of a given kinase.

IIB. Inhibited Production of iNOS and IL-1β by Activated Glia.

Several figures relate more specifically to the following description and examples, and are provided as follows:

FIG. 3. Another representative synthetic scheme and resulting structures of the corresponding compositions. The reaction scheme for the synthesis of the compounds is shown in (A), where reactants and products at each step are indicated. The structures and names of the final products examined are shown in (B). Established chemistry techniques were used in the synthesis and characterization of the products, and can be extended in a straight-forward manner to provide other compositions of this invention.

FIG. 4. Cell-based screen for functional effects of synthetic compounds on LPS-stimulated NO release from BV-2 cells. BV-2 cells were incubated for 24 hr with LPS (500 ng/ml) in the presence of increasing concentrations of: A) MW01-070C; B) MW01-026Z; C) MW01-118Z; D) MW01-119Z; E) MW01-051Z; F) MW01-160Z; G) MW01-196A; H) MW01-024Z; I) SB203580 J) PDTC; K) U0126; L) PD98059. The nitrite levels in conditioned media were determined. Inhibition is expressed as percentage of control values, where the control is the nitrite level in cells stimulated with LPS alone.

FIG. 5. Effects of two compounds on LPS-stimulated iNOS and IL-1β production in rat astrocyte cultures. Astrocyte cultures were incubated for 24 hr with control buffer (C), LPS (100 ng/ml) alone, or LPS in the presence of increasing concentrations (0.1, 0.3, 1, 3, 10 µM) of MW01-070C (panel A) or MW01-196A (panel B). The levels of iNOS, proIL-1β, and GFAP were determined by Western blot of cell lysates.

FIG. 6. Effects of MW01-070C on astrocytes treated with various activating stimuli, and analysis of multiple activation responses. Astrocyte cultures were stimulated for 12 hr with Aβ (10 µM), S100B (0.5 µM), or LPS (100 ng/ml) in the absence (−) or presence (+) of MW01-070C (10 µM). The levels of A) iNOS, proIL-1β and GFAP; and B) apoE and COX-2 were determined by Western blot of cell lysates.

FIG. 7. Effects of MW01-070C on phosphorylation of transcription factors and an upstream activating kinase. BV-2 cells were incubated for 4 hr with control buffer (lane 1), 500 ng/ml LPS (lane 2), or 100 ng/ml LPS+10 µM MW01-070C (lane 3). The levels of phosphorylated (p-) ATF2, p38, and CREB were determined by Western blot of cell lysates, using antibodies that are specific for the phosphorylated forms of these proteins.

With reference to the aforementioned figures, associated examples, data and results, various compositions of this invention can also be utilized and compared as described, below, further illustrating a new chemical class of compounds with enhanced activity and selectivity for modulation of glial activation in response to a diversity of disease relevant stimuli. The results obtained provide insight into the quantitative importance of convergent protein kinase mediated signal transduction pathways in glial activation as well as the structure-activity relationships needed for future medicinal chemistry refinement. As mentioned above, MW01-070C (compound 1, chart 1 and as referenced in Table 3) appears to inhibit iNOS and 1β production in activated glia through modulation of transcription factor phosphorylations via mechanisms that are distinct from the extensively studied and targeted p38 MAPK pathway. Because so little is known about the signal transduction mechanisms linked to iNOS and IL-1β regulation in brain glial activation, the results and the reagents reported here provide important insight into relevant pathways and the tools needed to dissect their relative quantitative contribution to the biological endpoint. The demonstration that MW01-070C has desirable pharmacological properties, has enhanced and selective activity, targets different pathways compared to currently available experimental drugs, and is amenable to rapid chemical diversification with facile chemistries, make it an attractive starting point for future refinement.

The congruence among the dose related effects of MW01-070C on quantifiable levels of NO accumulation, production of iNOS, and selected transcription factor phosphorylations allows a mechanistic linkage among these cellular events that had not been provided in previous investigations of glial activation and its modulation. MW01-070C's ability to block production of iNOS and IL-1β in response to multiple activating stimuli and its superior activity compared to PD98059 and U0126 in suppression of NO accumulation is consistent with MW01-070C functioning at later steps in intracellular signal transduction pathways, where diverse mechanisms converge on common biological end points. The net effect of a protein kinase inhibitor on animal function is determined by the series of upstream events and downstream pathways, as well as the protein kinase isoforms present. This integrated response is the basis for the desired phamacological effects of compounds that target widely distributed enzymes, such as inhibitors of COX-2 and p38 MAPK. This body of knowledge is currently not available for glial activation responses and their modulation for several reasons, including the lack of appropriate ligands for the dissection of pathways and their quantitative contribution to the biological response. However, the data presented here suggest that targeting of late steps in protein phosphorylation pathways linked to regulation of gene transcription might be an effective approach in drug discovery for neuroinflammation, as it is for other inflammatory disorders [Bhagwat, S. S., Manning, A. M., Hoekstra, M. F., and Lewis, A. (1999) *Drug Discovery Today* 4, 472-479], especially considering the combinatorial possibilities among kinases, transcription factors, and gene promoters.

There are a variety of potential pathways that could be targeted in early stage drug discovery research in neuroinflammation, and the high failure rate for evolution into safe and effective drugs documents the need to pursue these various alternative pathways in parallel. Regardless of the pathway being targeted, however, there are key features that are attractive in early generation compounds. These include the ability of the ligand to modulate a disease surrogate biological end point in a dose dependent manner without perturbation of related pathways. MW01-070C and related compounds possess these attractive properties of an early generation compound. It can down modulate IL-1β and iNOS production in a dose dependent manner, while not altering apoE or COX-2 levels, and the doses required for this effect are in the same range as those that bring NO production to basal levels. The effects of reactive NO derivatives, such as peroxynitrate, have been directly linked to neurodegenerative disease pathology, making excessive NO production a potential drug discovery target [Akiyama, H., Barger, S., Barnum, S., Bradt, B., Bauer, J., Cole, G. M., Cooper, N. R., Eikelenboom, P., Emmerling, M., Fiebich, B. L., Finch, C. E., Frautschy, S., Griffin, W. S., Hampel, H., Hull, M., Landreth, G., Lue, L., Mrak, R., Mackenzie, I. R., McGeer, P. L., O'anion, M. K., Pachter, J., Pasinetti, G., Plata-Salaman, C., Rogers, J., Rydel, R., Shen, Y., Streit, W., Strohmeyer, R., Tooyoma, I., Van Muiswinkel, F. L., Veerhuis, R., Walker, D., Webster, S., Wegrzyniak, B., Wenk, G., and Wyss-Coray, T. (2000) *Neurobiol. Aging* 21, 383-421]. The induction of the proinflammatory cytokine IL-1β is thought to be an early step in the neuroinflammatory activation cycle linked to disease progression, making IL-1β production a potential drug discovery target in neuroinflammation research [Akiyama, H., Barger, S., Barnum, S., Bradt, B., Bauer, J., Cole, G. M., Cooper, N. R., Eikelenboom, P., Emmerling, M., Fiebich, B. L., Finch, C. E., Frautschy, S., Griffin, W. S., Hampel, H., Hull, M., Landreth, G., Lue, L., Mrak, R., Mackenzie, I. R., McGeer, P. L., O'Banion, M. K., Pachter, J., Pasinetti, G., Plata-Salaman, C., Rogers, J., Rydel, R., Shen, Y., Streit, W., Strohmeyer, R., Tooyoma, I., Van Muiswinkel, F. L., Veerhuis, R., Walker, D., Webster, S., Wegrzyniak, B., Wenk, G., and Wyss-Coray, T. (2000) *Neurobiol. Aging* 21, 383-421]. ApoE is an endogenous anti-inflammatory protein that can down regulate glial responses to activating stimuli, raising the possibility that it should remain undisturbed by a lead compound [Hu, J., LaDu, M. J. and Van Eldik, L. J. (1998) *J. Neurochem.* 71, 1626-1634; LaDu, M., Shah, J. A., Reardon, C. A., Getz, G. S., Bu, G., Hu, J., Guo, L., and Van Eldik, L. J. (2001) *Neurochem. Intl.*, in press; Laskowitz, D. T., Thekdi, A. D., Thekdi, S. D., Han, S. K., Myers, J. K., Pizzo, S. V., and Bennett, E. R. (2001) *Exp. Neurol.* 167, 74-85]. COX-2 is an enzyme, like iNOS, that is induced in response to a variety of activating stimuli and is involved in distinct biological processes, some of which complement those of iNOS. MW01-070C represents, therefore, a first generation compound that has a variety of attractive properties from a pharmacological perspective as it selectively targets steps in the glial activation loop that are disease linked and proximal to the initiating stimulus. In addition to these basic attractive features, MW01-070C does not target the same regulatory pathways that can be critical in peripheral inflammatory responses, such as the p38MAPK/ATF2 pathway [Badger, A. M., Bradbeer, J. N., Votta, B., Lee, J. C., Adams, J. L., and Griswold, D. E. (1996) *J. Pharmacol. Exp. Ther.* 279, 1453-1461].

The results do not allow for determination whether the primary desired effect of MW01-070C is due to a robust effect on IL-1β production, with a subsequent reduction in the ability of IL-1β to induce iNOS in a paracrine or autocrine mechanism, or if MW01-070C alters both IL-1β and iNOS production directly through its targeting of common signaling pathways. Current research that addresses the mechanism of action of MW01-70C and related compounds will allow discrimination among these and other possibilities. Regardless, MW01-070C's robust and selective effects on discrete pathways that mediate neuroinflammatory responses, but lack of an effect on signaling pathways important for inflammation responses in peripheral tissues or endogenous anti-inflammation responses in brain, are biological features that could be leveraged in future medicinal chemistry enhancements of MW01-070C or related compounds of the type described herein.

EXAMPLE 3

Cell Culture and Glial Activation Assays

Primary rat cortical glial cultures consisting of ~95% astrocytes, ~5% microglia were prepared and maintained as described previously [Hu, J., Castets, F., Guevara, J. L., and Van Eldik, L. J. (1996) *J. Biol. Chem.* 271, 2543-2547]. The murine microglial BV-2 cell line [Blasi, E., Barluzzi, R., Bocchini, V., Mazzolla, R., and Bistoni, F. (1990) *J. Neuroimmunol.* 27, 229-237] was provided by Dr. Michael McKinney (Mayo Clinic, Jacksonville, Fla.).

Brain mixed glia cultures (astrocytes and microglia) were treated with activating stimuli as previously described [Hu, J., Akama, K. T., Krafft, G. A., Chromy, B. A., and Van Eldik, L. J. (1998) *Brain Res.* 785, 195-206]. Briefly, cells were plated at $1 \times 10^5$ cells/well in a 12-well tissue culture plate, and grown overnight in αMEM (Life Technologies) containing 10% fetal bovine serum (FBS). Media was then removed, cells were rinsed with phosphate buffered saline (PBS), and the media was changed to serum-free αMEM containing N2 supplements (Life Technologies) for at least a 24 hr incubation prior to treatment (to allow the cells to return to a non-activated state). Cells were then treated for 12-24 hrs with an activating stimulus or control buffer in the presence or absence of the compound to be tested, and cell lysates harvested for Western blot analysis. When compounds or drugs were used, they were added to the cells immediately before the activating stimulus.

The activating stimuli used were Aβ 1-42 peptide, S100B, or LPS. Aβ 1-42 peptide was obtained and prepared as previously described [Watterson, D. M., Mirzoeva, S., Guo, L., Whyte, A., Bourguignon, J.-J., Hibert, M., Haiech, J., and Van Eldik, L. J. (2001) *Neurochem. Intl.*, in press]. Aβ aged by this procedure is primarily oligomeric, with no Aβ fibrils detected by atomic force microscopy [Hu, J., Akama, K. T., Krafft, G. A., Chromy, B. A., and Van Eldik, L. J. (1998) *Brain Res.* 785, 195-206]. Control buffer contained the same concentration of DMSO as the Aβ stock. Bovine brain S100B was expressed from recombinant S100B [Van Eldik, L. J., Staecker, J. L., and Winningham-Major, F. (1988) *J. Biol. Chem.* 263, 7830-78373], purified as previously described [Lam, A. G. M., Koppal, T., Akama, Guo, L., Craft, J. M., Samy, B., Schavocky, Watterson, D. M., and Van Eldik, L. J. (2001) *Neurobiol, Aging*, in press], and used at a final concentration of 10 μg/ml (0.5 μM). Bacterial lipopolysaccharide (LPS) from *Salmonella typhimurium* (Sigma L2622) was resuspended in sterile PBS at 10 mg/ml, and was used at a final concentration of 100 ng/ml.

For analysis of transcription factor phosphorylation, BV-2 cells were plated at $2 \times 10^5$ cells/well in a 12-well tissue culture plate, and grown for 48 hrs in αMEM containing 10% FBS. Immediately before treatment, media was removed, cells were rinsed with PBS, and media changed to serum-free αMEM. Cells were then treated for 4 hrs with control buffer or LPS (500 ng/ml) in the presence or absence of MW01-070C (10 μM), and cell lysates harvested for Western blot analysis.

EXAMPLE 4

Western Blot Analysis

Cell lysates were prepared and Western blots were done as previously described [Petrova, T. V., Akama, K. T., and Van Eldik, L. J. (1999) *Proc Natl Acad Sci USA* 96, 4668-4673] using equal volumes of cell extracts per gel lane. The following antibodies were used: monoclonal anti-iNOS (1:1000 dilution, Transduction Labs); polyclonal anti-rat IL-1β (1:1000 dilution, R&D Systems, Inc.); monoclonal anti-glial fibrillary acidic protein (GFAP) (1:$10^8$ dilution, Sigma); polyclonal anti-rat apoE (1:15,000 dilution) prepared as described [LaDu, M. J., Shah, J. A., Reardon, K., Getz, G. S., Bu, G., Hu, J., Guo, L., and Van Eldik, L. J. (2000) *J. Biol. Chem.* 275, 33974-33980]; polyclonal anti-COX-2 (1:500 dilution) and monoclonal anti-phosphoATF2 (1:1000 dilution) from Santa Cruz Biotechnology; polyclonal anti-phosphoCREB (1:1000 dilution), polyclonal anti-phosphop38 MAPK (1:1000 dilution), polyclonal anti-phosphop90RSK (1:1000 dilution), and monoclonal anti-phosphoERK1/2 (1:1000 dilution) from Cell Signaling.

EXAMPLE 5

Cell-based Assay for Inhibition of NO Production

Compounds were tested for their effects on NO production by LPS-stimulated BV-2 cells as previously described [Mirzoeva, S., Koppal, T., Petrova, T. V., Lukas, T. J., Watterson, D. M., and Van Eldik, L. J. (1999) *Brain Res.* 844, 126-134]. The levels of nitrite, a stable NO metabolite, in conditioned media were determined by the Griess assay as previously described [Hu, J., Castets, F., Guevara, J. L., and Van Eldik, L. J. (1996) *J. Biol. Chem.* 271, 2543-2547]. Stock solutions of compounds were prepared in DMSO or in water. When stock solutions were prepared in DMSO, control wells contained the same final concentration of DMSO as the compound-containing wells. Solutions of compounds for cell treatments were diluted to a 10× final concentration by dilution of stock solutions of drugs in αMEM media. The commercially available drugs tested were: SB203580 (Alexis Corporation), U0126 (Cell Signaling), PDTC (Sigma), and PD98059 (Alexis Corporation).

EXAMPLE 6

Synthesis of Compounds.

Referring to FIG. 3, to embellish the procedures of example 1, above, and as a general synthetic scheme, commercially available bromocarboxylic acids (Sigma-Aldrich) were dissolved in ethanol and one equivalent of 4N HCl/dioxane (Sigma-Aldrich) and the mixture allowed to react for at least 45 hours at ambient temperature (20 to 22° C.). The reaction mixture was rotary evaporated in a round bottom flask to a yellow oil, triturated twice with hexane, and rotary evaporated again to give a yellow oil which was further dried under vacuum. The carboxylic acid esters of the respective bromocarboxylic acids were dissolved in a minimum amount (2 mL for 1 mmol bromoester) of dimethylformamide (DMF; Allied Signal) and heated to 80° C. The module A components of 2-amino-4-picoline (Sigma-Aldrich), 1-(2-pyrimidyl)piperazine (Sigma-Aldrich), or 3-aminopyridazine [Wermuth, C. G., Bourguignon, J. J., Schlewer, G., Gies, J. P., Schoenfelder, A., Melikian, A., Bouchet, M. J., Chantreux, D., Molimard, J. C., and Heaulme, M. (1987) *J. Med. Chem.*, 30, 239-249], were added at an approximate 0.75 mole ratio. The reactions were allowed to proceed for upwards of 6 hours, with additional DMF added in the first 2 hrs to re-suspend any solids formed during the reaction. The extent of reaction was monitored by analytical HPLC in terms of disappearance of reactants and appearance of a major new UV absorbance peak that had an experimentally determined mass corresponding to the expected mass of the product. The reaction mix was precipitated with ethyl ether and filtered on a medium pore glass funnel (Pyrex) under vacuum. The precipitate was dried in vacuo and the product obtained as a light yellow granular powder.

The resultant esters containing their respective A components/modules were added to glacial acetic acid and 12 N HCl, and heated to 90° C. for 5-10 hrs in a reaction flask equipped with a reflux condensor. The extent of reaction was monitored by analytical HPLC in terms of disappearance of reactants and appearance of a major new UV absorbance peak that had an experimentally determined mass corresponding to the expected mass of the product. The product was precipitated in ethyl ether and, after drying in vacuo, yielded the respective compounds as a yellow solid. These products were dissolved in a minimal amount of DMF, to which one equivalent of 1-hydroxybenzotriazole (HOBt; Pierce Chemicals) and one equivalent of 1-ethyl-3(3-dimethyl-amiopropyl)carboimide (EDC; Sigma-Aldrich) were added, and the mixture stirred for one hour at 0° C. The respective B module compounds were suspended in a minimal amount of DMF and added to the activated solution. When obtained as the hydrochloric salts, the commercially available B module compounds were neutralized with an equivalent of diisopropylethylamine (DMA) before addition to the activated solution. The reaction mixture was allowed to warm to ambient temperature of 20-22° C. and allowed to stir for at least 12 h. The pH of the reaction was adjusted, when necessary, to pH 6 with DIEA. The extent of reaction was monitored by analytical HPLC in terms of disappearance of reactants and appearance of a major new UV absorbance peak that was later shown to correspond to the expected mass of the product. The reaction mix was precipitated with ethyl ether and filtered on a medium pore glass filter (Pyrex) under vacuum. The precipitate was dried in vacuo and the product obtained as a light yellow granular powder.

EXAMPLE 7

Analytical Chemistry.

HPLC was on a commercially available (Microsorb) reverse phase column (C18, 5 μm, 100 A particle) using 0.08% (v/v) TFA and 80% (v/v) acetonitrile/water as limit buffers. Routine mass spectrometry monitoring of reactions and products was done on a PerSeptives Voyager DE-Pro matrix-assisted laser-desorption time of flight mass spectrometry (MALDI-TOF MS). Ultraviolet (UV) and visible spectroscopy was done on a Beckman DU7400 system (Beckman Coulter). Aliquots of compounds for storage were made by dissolving final dry products in HPLC grade methanol (Sigma-Aldrich), UV spectra taken for determination of concentration, and aliquots made, dried in vacuo, and stored as dry solid at 4° C. Prior to assay, 5-10 mM assay stock solutions were prepared by addition of the appropriate volume of sterile, pyrogen-free DMSO (Sigma-Aldrich) to a tube containing a known amount of dried compound. NMR spectroscopy of the lead compound MW01-070C (FIG. 1) was done by Acorn NMR Inc. The proton NMR for MW01-070C was indicative of the proposed structure. Resonances corresponding to a tricyclic nitrogenous ring, a $CH_2$ alkyl chain, and a piperazine group with an aromatic moiety were observed.

EXAMPLE 8

As discussed, above, compound MW01-070C was discovered by the use of a modular parallel synthesis approach based on an aromatic pyridazine scaffold as the starting point, and the testing of products for quantitative function in a cell based assay using a disease linked surrogate end point. The modular approach and synthetic scheme for the compounds presented in this report are shown in FIG. 3A. The rationale for selection of synthetic modules was their drug like properties based on prior reports in the literature, the facility with which the module could be incorporated using the common synthetic schema, and the availability of precursors from commercial or other sources. The details of syntheses are provided, above, and the structures of the compounds reported here are shown in FIG. 3B. The quantitative ability of these compounds to regulate a relevant surrogate endpoint, NO accumulation in response to an activating stimulus, in the cell based screen is shown in FIG. 4. Also shown in FIG. 4 for comparative purposes are the effects of selected compounds that are experimental drugs and protein kinase inhibitors currently used as standards in the field.

EXAMPLE 9

The results demonstrate that MW01-070C is more effective at downmodulating NO production than the widely used experimental therapeutics that target the MAPK pathways. This enhanced functional activity is found in compounds that have an aromatic 3-aminopyridazine moiety in the A module, linked by an alkyl chain of optimal length to a aromatic piperazine derivative in the B module (see MW01-070C in FIG. 3B). The A module of MW01-070C is the aromatic pyridazine scaffold found in the FITS of the focused chemical library. The B component/module in MW01-070C was discovered in a structure based search of the available chemicals database for aromatic heterocylic compounds, with prioritization of choices for inclusion in parallel syntheses based on prior use in the synthesis of other drug like compounds. For example, the 1-(2-pyrimidyl)piperazine is commercially available and is present as a chemical module in various CNS active compounds that are widely used clinically, and is thought to be an important contributor to the pharmacodynamics and pharmacokinetics of the clinically effective drugs of which it is a component [Garattini, S., Caccia, S., and Mennini, T. (1982) *J. Clin. Psych.* 43, 19-24; Apter, J. T. and Allen, L. A., (1999) *J. Clin. Psychopharmacol.* 19, 86-93]. Therefore, 1-(2-pyrimidyl)piperazine was obtained from a commercial source and was used in the modular parallel synthetic scheme (see FIG. 3A and Experimental Procedures) to make MW01-070C, which was found to have enhanced activity to downmodulate NO production by activated glia in a dose dependent manner (FIG. 4). In a similar manner, a variety of other aromatic heterocyclic modules, including other pyridazine derivatives found as components in previous CNS drug development [Melikian, G. Schlewer, J. P. Chambon, and C. G. Wermuth. (1992) *J. Med. Chem.* 35, 4092-4097; Satuminio, C., Abarghaz, M., Schmitt, M., Wermuth, C.-G., and Bourguignon, J.-J. (1995) *Heterocycles* 41, 1491-1501; Wermuth, C. G., Bourguignon, J. J., Schlewer, G., Gies, J. P., Schoenfelder, A., Melikian, A., Bouchet, M. J., Chantreux, D., Molimard, J. C., and Heaulme, M. (1987) *J. Med. Chem.* 30, 239-249], were used in the B module (see MW01-026Z, MW01-118Z and MW01-119Z in FIG. 3B), with varying levels of activity in the cell based assay (FIG. 4).

EXAMPLE 10

The quantitative cell based assay results demonstrated that slight variations of the characteristics of component B alone can have a profound effect on function. For example, compounds MW01-026Z, MW01-118Z and MW01-119Z all contain similar aromatic heteroatom derivatives in the B module (FIG. 3B), but they vary in their quantitative ability to inhibit NO accumulation by the activated BV2 cells (FIG. 4). Further, the results demonstrate that the presence of similar chemical groups in modules A and B does not yield optimal activity, arguing against the basis of enhanced activity being due to a simple bi-cationic effect of aromatic pyridazines. For example, MW01-119Z contains aromatic pyridazine derivatives in both modules. Although MW01-119Z has better efficacy than established anti-inflammatory compounds like SB203580, which targets predominantly the p38 MAPK mediated pathway, MW01-119Z is still not as active as MW01-070C, which has a combination of an aromatic pyridazine (A) and a piperazine derivative (B). The results demonstrate the strict requirement for specific sets of heterocycle structures in an asymmetric molecule for optimal activity, and indicate that systematic variations of module B can have a profound effect on function, making it a fruitful next step in future inhibitor refinement and development.

EXAMPLE 11

The functional importance of the aromatic 3-aminopyridazine analog in the A module and the 1-(2-pyrimidyl)

piperazine in the B module of MW01-070C is context dependent. For example, a symmetrical compound containing 1-(2-pyrimidyl)piperazine in both the A and B modules (MW01-024Z in FIG. 3B) does not have any greater cellular activity than commercially available drugs and inhibitors (FIG. 4). In addition, the use of a simpler aromatic heterocycle in the A module in combination with the 1-(2-pyrimidyl)piperazine in the B module, such as in MW01-196S (FIG. 3B), results in a compound with little activity in the cell based assay (FIG. 4). The functional importance of the 1-(2-pyrimidyl)piperazine in the B module and the aromatic 3-aminopyridazine in the A module is also dependent on the context of the R2 or G components, as evidenced by compounds MW01-051Z and MW01-160Z. These compounds are identical to MW01-070C except for the presence of fewer carbon atoms in the alkyl chain (see FIG. 3B). As illustrated in FIG. 4, these compounds show reduced activity in the cell based assay as the carbon chain length of the middle module is shortened. MW01-051Z has significant NO inhibition activity compared to commercially available compounds, but is less active than MW01-070C, and MW01-160Z is no more active than inhibitors of the NFκB pathway (PDTC). Taken together, the proof of principle results presented here demonstrate that a variety of aromatic pyridazine derivatives can give improved activity, but that optimal activity requires a discrete set of structural features for each of the A and B modules that is also dependent on the context of the overall final structure.

EXAMPLE 12

The quantitative cell based assay results (FIG. 4) not only demonstrate the development of a new chemical class of compounds with improved quantitative function compared to those currently available, they also allow a tentative ranking of the quantitative importance of various gene-regulating protein kinase pathways to a biological end point. For example, SB203580, U0126 and PD98059, and PDTC are inhibitors of p38 MAPK, MEK1/2, and NFκB signaling pathways, respectively, and each of these distinct intracellular signal transduction pathways converge at the level of transcription regulation in glial activation [Bhat, N. R., Zhang, P., Lee, J. C., and Hogan, E. L. (1998) *J. Neurosci.* 18, 1633-1641; Da Silva, J., Pierrat, B., Mary, J.-L., and Lesslauer, W. (1997) *J. Biol. Chem.*, 272, 28373-28380; Akama, K T, Albanese, C, Pestell, R G and Van Eldik, L J (1998). *Proc. Natl. Acad. Sci. USA* 95, 5795-5800]. The dose dependent comparison of these compounds to each other and to MW01-070C using a quantifiable biological assay (FIG. 4) indicates the relative quantitative contribution of each of these distinct pathways to the production of NO by LPS activated BV-2 cells. Combinations of SB203580 and PD98059 result in enhanced activity compared to the use of either compound alone (FIG. 4 and data not shown), but this activity is still less than that seen with MW01-070C (FIG. 4), and combinations of these drugs with MW01-070C provided only a minimal enhancement of MW01-070C's activity that was not readily distinguishable from that of MW01-070C alone (data not shown). The inability to see significant enhancement of MW01-070C activity with the addition of maximal doses of SB203580 might be based on the limits of the assay being approached, reflecting a basal NO production as the synthesis of the iNOS enzyme has been reduced to background levels.

EXAMPLE 13

The use of a cloned cell line facilitates consistency in results between screening experiments compared to use of primary glial cell cultures, and results from HTS of drugs with BV-2 cells have been correlated with responses by astrocyte and microglial cultures from rat brain [Watterson, D. M., Mirzoeva, S., Guo, L., Whyte, A., Bourguignon, J.-J., Hibert, M., Haiech, J., and Van Eldik, L. J. (2001) *Neurochem. Intl.*, in press]. Therefore, the quantitative analyses of BV-2 cells were extended to the examination of MW01-070C effects on iNOS and IL-1β protein production in mixed cultures of rat cortical glia in order to gain insight into how these compounds might be altering the cytokine cycle of neuroinflammation. FIG. 5A shows that MW01-070C gives a dose dependent inhibition of LPS-stimulated iNOS and IL-1β production. The levels of the astrocyte marker protein GFAP are shown in FIG. 5 as a control. The GFAP results provide a gel loading control for the western blot analysis step, and they also provide a biological response control to demonstrate that the decreased production of iNOS and IL-1β by MW01-070C is selective and not a result of general protein inhibition or cytotoxicity. In order to correlate this dose dependent effect with the pharmacophore properties of MW01-070C that were linked to inhibition of NO accumulation, we did control experiments with structural analogs of MW01-070C that have less activity in the quantitative BV-2 cell assay. As shown in FIG. 5B, the structural analog MW01-196S does not show dose dependent inhibition of iNOS and IL-1β production over this same dose range.

These results in FIG. 5 are congruent with the quantitative NO production results shown in FIG. 4. The major source of increased NO production in response to glial activating stimuli is the induction of iNOS, a form of NOS that is at least an order of magnitude more active in NO production than the various constitutive forms of NOS. The results to this point are consistent with MW01-070C being the most effective inhibitor known for blocking LPS-induced NO accumulation through its ability to block increased iNOS production, and demonstrate that MW01-070C is also an effective dose dependent inhibitor of IL-1β production by glia.

EXAMPLE 14

The inhibition of iNOS and IL-1β production by MW01-070C, however, is not limited to LPS stimulation. As shown in FIG. 6A, MW01-070C also inhibits the increase in iNOS and IL-1β brought about by Aβ 1-42 and S100. The rationale for examination of Aβ stimulation is its involvement as an initiating event in models of AD initiation and progression. The stimulation by Aβ is seen (FIG. 6) with preparations of the Aβ peptide (see Experimental Procedures) that are known to have neurotoxic activity [Hu, J., Akama, K. T., Krafft, G. A., Chromy, B. A., and Van Eldik, L. J. (1998) *Brain Res.* 785, 195-206; Lambert, M. P. Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) *Proc. Natl. Acad. Sci. USA* 95, 6448-6453]. The rationale for examination of 5100 stimulation is its presence as an astrocyte protein that can function as an autocrine and paracrine cytokine, and its increased production in AD and other neuroinflammatory related disorders [Griffin, W. S. T., Stanley, L. C., Ling, C., White, L., MacLeod, V., Perrot, L. J., White, C. L., III, and Araoz, C. (1989) *Proc. Natl. Acad. Sci. USA* 86, 7611-7615; Flu, J., Castets, F., Guevara, J. L., and Van Eldik, L. J. (1996) *J. Biol. Chem.* 271, 2543-2547; Donato, R. (1999) *Biochim. Biophys. Acta* 1450, 191-231; Van Eldik, L. J., and Griffin, W. S. T. (1994) *Biochim. Biophys. Acta* 1223, 398-403]. Although MW01-070C inhibits iNOS and IL-1β production in glia activated by a variety of disease relevant stimuli, this is still a selective effect as shown by no change in GFAP levels (FIG. 6A) and no effect on COX-2 or apoE production (FIG. 6B), the latter being an endogenous anti-inflammatory protein. In addition, there was no evidence of cytotoxicity in cell culture over the entire dose range of inhibitor, and no major liver, kidney or brain damage based on histology of these organs after high dose injections into rats (data not shown).

EXAMPLE 15

The effect of MW01-070C on iNOS and IL-1β levels in response to multiple activating stimuli (FIG. 6) and its robust dose dependent activity with a quantifiable end point (FIG. 4), raise the possibility that MW01-070C works at a late step in intracellular signal transduction pathways, where multiple mechanisms and cross-talking pathways are known to converge on common biological end points, iNOS and IL-1β gene regulation. This possibility is consistent with previous reports [Bhat, N. R., Zhang, P., Lee, J. C., and Hogan, E. L. (1998) *J. Neurosci.* 18, 1633-1641; Da Silva, J., Pierrat, B., Mary, J.-L., and Lesslauer, W. (1997) *J. Biol. Chem.* 272, 28373-28380] on glial activation mechanisms using pathway selective inhibitors, such as SB203580 for the p38 MAPK or U0126 and PD98059 for the ERK pathway. The data (FIG. 4) with SB203580, U0126 and PD98059 inhibition of NO production in BV-2 cells are consistent with these previous reports. One of these previous reports [Bhat, N. R., Zhang, P., Lee, J. C., and Hogan, E. L. (1998) *J. Neurosci.* 18, 1633-1641] also demonstrated that inhibitors of other pathways were enhanced in their effectiveness when combined with inhibitors of p38 MAPK, a promising drug discovery target in anti-inflammation research. This raises the logical possibility that MW01-070C's enhanced activity might include inhibition of p38 MAPK. Although the mechanism of MW01-070C action was not a primary goal of this proof of principle report, the potential of MW01-070C being a p38 MAPK pathway inhibitor was probed by analysis of a known endogenous substrate of p38 MAPK. Cells were treated with LPS in the presence or absence of MW01-070C, and the change in phosphorylation state of p38 MAPK and one of its substrates, the transcription factor ATF2, was monitored by the use of phosphoprotein selective antibodies. The western blot results shown in FIG. 5 demonstrate that LPS stimulates an increase in phospho-ATF2, and the presence of MW01-070C does not inhibit the phospho-ATF2 stimulation. Further, phospho-p38 levels are increased in response to glial activation stimuli, and this stimulation is not blocked by MW01-070C (FIG. 7). These results demonstrate that the p38 MAPK pathway is activated in these cells, as expected, but there is no detectable down modulation of the p38 MAPK pathway by MW01-070C. As a positive control, another gene regulating signal transduction pathway was probed. As shown in FIG. 7, phospho-CREB is increased in response to cell activation, and this increase in phospho-CREB is inhibited in cells treated with MW01-070C. These results demonstrate that MW01-070C's mechanism of action does not include inhibition of the well-studied p38 MAPK pathway that is important in peripheral tissue inflammatory responses, but may include direct or indirect effects on the regulation of iNOS and IL-1β expression by the regulation of CREB and associated proteins.

III. Inhibition of Death Associated Protein Kinase (DAPK) and Reduction of Hypoxia-Ischemia Induced Brain Damage.

The following figure relates more specifically to the corresponding descriptions and examples.

FIG. 8. Comparative data analysis pertaining to the indicated animal subjects, in terms of hemispheric weight loss. Reference is made to examples 19-21.

Death and suffering resulting from brain injury, especially the effects of hypoxia-ischemia, is a major medical problem. For example, stroke and traumatic brain injury are leading causes of death and the major cause of disabilities in the United States (Read et al., 2001; Brott, et al., 2000). Stroke is estimated to have an annual health care cost of $30-50 billion and to account for half of all hospitalizations in the area of acute neurological disorders (Read et al, 2001), while traumatic brain injury is a prevalent cause of death and disability in the young (Ghajar, 2000). There are few approved therapies for these leading causes of death and suffering, with lack of knowledge about mechanisms being a contributing factor to this major umet need (Read et al; Ghajar 2000; Brott, 2000).

However, progress in understanding the cellular and molecular changes occurring as a result of these brain insults has recently brought a focus on neuronal programmed cell death (apoptosis), especially the role of certain protein kinase mediated pathways and calcium signaling (Lee et al., 2000). A recent proof of principle report (Namura et al., 2001) showed that commercially available small molecule protein kinase inhibitors of MAP kinases can assist with deconvolution of the complex interdigitated signaling pathways involved in neuronal cell death, and suggested that protein kinases might be potential drug discovery targets for this disease area. Small molecule inhibitors of mixed lineage kinase have also indicated (Maroney et al., 2001) the potential of targeting protein kinases as a drug discovery approach and have been effective reagents in the deconvolution of complex, interdigitated signal transduction pathways. The recent literature, therefore, demands that further investigation of logical intracellular death associated targets be explored for inhibitor development, with protein kinases and calcium signal transduction pathways being especially cogent. In this regard, death associated protein kinase (DAPK), a calcium/calmodulin regulated, serine-threonine protein kinase, is a potential drug discovery target (Schumacher et al., 2002) for brain injury resulting from stroke or other diseases associated with brain hypoxia-ischemia.

DAPK is involved in the early steps of apoptosis, and undergoes an increase prior to neuronal cell death following transient ischemia in animal models of stroke (Yamamoto et al., 1999). The mechanism of DAPK's action in neuronal cell death is unknown, although mutations in the kinase domain abrogate DAPK's pro-apoptotic activity. A major limitation to the study of the role of DAPK in cell function and its potential as a drug discovery target is the lack of established in vivo protein substrates and the lack of selective, small molecule, cell permeable inhibitors. The lack of knowledge about endogenous substrates or absence of useful inhibitors for various death kinases is characteristic of enzymes discovered as open reading frames (ORFs) in a genomic sequence programs or functional genetic screens. ORFs that encode protein kinase or other enzyme domains are linked to cell functions with limited knowledge of relevant substrates or cellular mechanisms. Linkage of enzyme activity to cellular responses is facilitated by the discovery of small molecule inhibitors. Although there are no selective, small molecule DAPK inhibitors, the recent characterization of DAPK's enzymic properties and the establishment of a quantitative assay for DAPK activity (Velentza et al., 2001), combined with the elucidation of high-resolution crystal structures of its catalytic domain in various conformations (Tereshko et al., 2001), provide the foundation for inhibitor discovery.

The following provides the development of the first selective small molecule inhibitors of DAPK. The DAPK inhibitor was discovered as described herein by diversification of a new class of small molecule inhibitors of protein kinases based on a 3-amino-6-aryl pyridazine template alkylated at the N-2 position.

Briefly, as described more fully above, alkylacylated 3-amino-6-phenyl-pyridazines can be diversified at the 2-position using facile in parallel syntheses to alter kinase inhibitory activity (Mirzoeva et al., 2002). Compound 1, chart 1, above and referenced as MW0-070C, Table 3, a selective glial activation and CAMKII inhibitor and compound 02-10L-D05 (Watterson et al., 2001), a 3-amino-pyridazine based, non-selective kinase inhibitor, are less than optimal inhibitors of DAPK (IC50~80-100 µM).

However, these compounds are attractive starting points for the discovery of other DAPK inhibitors with improved potency and selectivity because they are based on the pyridazine template, which has the potential for diversification, and a good pharmacological profile. An object of this work is to identify rapidly a low micromolar DAPK inhibitor and selective versus other structurally and functionally related kinases (MLCK, PKC, CAMKII, suitable for use in animal models of disease. Based on the structures of compounds MW0-070C and prior art compound 02-10L-D05, compound MW01-055V (Table 6) was synthesized as provided herein and showed DAPK inhibitory activity similar to 02-10L-D05. Previous studies have shown that variations on the 2-position of 3-amino-6-phenyl-pyridazines can alter the selectivity for protein kinase inhibition, therefore, the first variation step involved the incorporation of $R_2$ in 3-amino-pyridazines (component A) that carry different substituents (Table 6) following the efficient synthetic approach that was previously used for the discovery of selective glial activation and CAMKII inhibitors (see, Section IIB., above).

Variations of component B (Table 6) suggest that the 3-amino-pyridazine at this position provides a phenyl ring on the 6-position to enhance DAPK inhibitory activity. Compound MW01-026Z, which was the most potent DAPK inhibitor among compounds tested also gave the best selectivity profile among the kinases that were tested. Therefore, compound MW01-026Z was selected as a starting point for variations on component A (Table 6). The data suggest that a phenyl ring may be used on the 6-position of the pyridazine component A for DAPK inhibitory activity. However, none of the A variations appeared to improve the activity and selectivity profile of CompoundMW01-026Z. (For purposes of illustration, only, component G was maintained throughout as an acyl moiety, while component $R_2$ was varied as shown. All such compositions are available using the synthetic techniques described herein. Enzyme assays were conducted per procedures described elsewhere herein.) A more comprehensive structure activity relationship is summarized in Table 7, below.

EXAMPLE 16

Animal Care. Experiments were performed in accordance with the relevant National Institutes of Health guidelines, and experimental procedures were approved by the Institutional Animal Care and Use Committee of Northwestern University, Chicago. Pups were housed with their dam in cages in the animal facility with a 12-hour light/dark cycle.

EXAMPLE 17

Induction of hypoxia-ischemia in postnatal day seven (P7) rats. Hypoxic-ischemic injury in P7 rats was induced using the well-characterized method of unilateral carotid ligation followed by hypoxia. This age is approximately equivalent to the 34 week gestation human infant. Male and female Wistar rats at P7 were removed from the mother and anesthetized with halothane (3.5% for induction and 1.5% for maintenance) 50% oxygen-balance nitrogen delivered via facemask. The right common carotid artery was identified and gently separated from the vagus nerve. The vessel was ligated with double 6-0 silk sutures to ensure cessation of blood flow. The entire procedure including time for the induction of anesthesia was completed in less than 6 minutes. Following carotid ligation, the animals were allowed to recover in a warm environment for 15 minutes, then returned to the dam for a further ninety minutes at an ambient temperature of 21° C. Induction of hypoxia was performed in custom-built plexiglass chambers based on published methods. The device comprises six interconnected plexiglass chambers (440 ml$^3$) submerged in water warmed to 37.5° C. Each chamber received pre-warmed, humidified hypoxia gas (8% oxygen/balance nitrogen) in a commercially calibrated preparation at a rate of 100 mm$^3$/minute regulated by flowmeter. Following 70 minutes of hypoxia, the pups were allowed to recover in room air for 15 minutes before return to the dam. Sham-operated animals underwent neck incision and vessel manipulation without ligation or hypoxia, This procedure produces selective brain injury in P7 rat pups in the hemisphere ipsilateral to the carotid occlusion. Hypoxia alone (control, contralateral hemisphere) does not result in any brain damage.

EXAMPLE 18

Drug Administration. Drug (MW01-026Z) was suspended in a 3% DMSO-balance saline solution, and administered via intraperitoneal (IP) injection into P7 rats at a dose of 5 mg/kg. Control animals received an equivalent volume of solvent vehicle. Drug or vehicle injections were performed 1 hour after the completion of carotid ligation.

EXAMPLE 19

Measurement of hemispheric weight. The comparison of disparities in hemispheric weight as a valid outcome measure of neurologic injury in the newborn rat has been demonstrated in studies correlating changes in hemispheric weight following hypoxia-ischemia with other measures of brain injury. The contralateral (non-ischemic) cerebral hemisphere is used as an internal control, the size of which is comparable to that of an age-matched brain not subjected to unilateral hypoxia-ischemia. This method allows time for the reduction in the initial cerebral edema and the evolution of clearly detectable infarcts.

Animals were sacrificed by halothane overdose at 7 days after hypoxia. The cerebellum, olfactory lobes and hindbrain were removed and the hemispheres sectioned at the midline. Left and right hemispheric weights were obtained to the nearest 0.1 mg using a high precision balance (Mettler Instruments). Differences in weight between the hypoxic-ischemic and control contralateral hemisphere were calculated for each animal using the formula: 100*(C−I)/C=% damage where I represents the weight of the ipsilateral and C the weight of the contralateral hemisphere.

EXAMPLE 20

Data Analysis. All data are expressed as mean±SEM. The degree of hypoxic-ischemic brain injury after treatment with drug or saline is expressed as the percentage of reduction in the tissue weight of the hemisphere ipsilateral to carotid ligation. This was calculated as a ratio of the right (ipsilateral, ischemic) to the left (contralateral, non-ischemic) hemispheric weights as described previously in the literature. The percent reduction in hemispheric weights were compared by unpaired t-test (StatView 5.0, SAS, Cary, N.C.). Statistical significance was assumed when P<0.05. (See, FIG. 8.)

EXAMPLE 21

Results

After 7 day recovery to P14, animals treated with vehicle showed a 28.2±6.5% (n=10) weight loss in the ischemic hemisphere compared to the contralateral hemisphere, or sham control. In contrast, the percent weight loss in the drug-treated group was 8.2±5.5% (n=7). There were no differences in mortality between groups.

TABLE 6

Composition A—$R_2$—C(=O)—B and Protein Kinase Inhibition

| Compound | A | $R_2$ | B | DAPK | MLCK | CAMKII | KC |
|---|---|---|---|---|---|---|---|
| | | | | | Inhibition* | | |
| MW01-055V | [structure] | $(CH_2)_{10}$ | [structure] | + | +++ | ? | + |
| MW01-008B | [structure] | $(CH_2)_{10}$ | [structure] | + | +++ | + | ? |
| MW01-026Z | [structure] | $(CH_2)_{10}$ | [structure] | +++ | ++ | − | − |
| MW01-020B | [structure] | $(CH_2)_{10}$ | [structure] | − | − | − | ? |
| MW01-125AZ | [structure] | $(CH_2)_{10}$ | [structure] | ++ | − | − | ++ |
| MW01-103B | [structure] | $(CH_2)_{10}$ | [structure] | + | ++ | − | ? |
| MW01-031Z | [structure] | $(CH_2)_{10}$ | [structure] | − | +++ | − | ? |

TABLE 6-continued

Composition A—R$_2$—C(=O)—B and Protein Kinase Inhibition

| Compound | A | R$_2$ | B | DAPK | MLCK | CAMKII | KC |
|---|---|---|---|---|---|---|---|
| | | | | | Inhibition* | | |
| MW01-038B | HN-pyridazine-phenyl | (CH$_2$)$_{10}$ | HN-pyridazine-phenyl | − | − | ? | ? |
| MW01-086B | HN-cinnoline-dihydronaphthalene | (CH$_2$)$_7$ | HN-pyridazine-phenyl | − | ++ | − | ? |
| MW01-097B | HN-pyridazine-phenyl | (CH$_2$)$_7$ | HN-pyridazine-phenyl | − | − | ? | ? |

*+++ = IC50 < 20 μM;
++ = 20 μM > IC50 > 50 μM;
+ = 50 μM > IC50 > 100 μM;
− = IC50 > 100 μM
? = not determined With reference to the compositions of Table 3 and the enzyme assay techniques described elsewhere herein, Table 7 provides structural activity relationships observed, in accordance with this invention.

TABLE 7

| Cpd ID | DAPK | CaMPK II | MLCK | PKC | PKA | BV-2 |
|---|---|---|---|---|---|---|
| MW01-055V | − | | + | + | − | − |
| MW01-044Z | | + | ± | | | − |
| MW01-118Z | + | + | − | − | − | ± |
| MW01-119Z | + | + | − | − | − | ± |
| MW01-053HZ | + | | + | | | + |
| MW01-008B | − | | + | | | + |
| MW01-026Z | + | − | + | − | − | ± |
| MW01-059A8Z | + | | | | | |
| MW01-023BHZ | + | + | + | + | − | − |
| MW01-023CHZ | − | + | + | + | − | |
| MW01-055HZ | ± | + | + | + | − | |
| MW01-020B | − | − | − | − | | + |
| MW01-022AHZ | + | + | + | − | − | ± |
| MW01-097B | − | | − | | | |
| MW01-070C | + | + | − | − | − | + |
| MW01-039D | − | + | − | − | − | + |
| MW01-009D | − | + | + | − | − | ± |
| MW01-023D | + | + | + | − | − | ± |
| MW01-038D | − | + | − | + | − | + |
| MW01-050AD | − | + | + | − | − | ± |
| MW01-050BD | − | + | + | + | − | + |
| MW01-050CD | − | + | + | + | − | ± |
| MW01-161AZ | − | + | − | − | − | + |
| MW01-102Z | | | | | | |
| MW01-010Z | + | + | − | + | − | − |
| MW01-051Z | − | + | − | − | − | − |
| MW01-160Z | − | − | | | | − |
| MW01-164BZ | | | | | | |
| MW01-164DZ | | | | | | |
| MW01-056-1AV | − | + | + | − | − | − |
| MW01-056-2V | − | + | + | + | − | ± |
| MW01-051V | − | + | + | − | − | − |
| MW01-070AS | + | + | | + | | |
| MW01-049HZ | + | | + | | | − |
| MW01-057D | | | | | | |
| MW01-008V | | + | + | − | − | + |
| MW01-089D | | | | | | |
| MW01-003B5 | + | + | + | + | − | − |
| MW01-003DS | + | + | + | + | − | ± |
| MW01-003AS | + | + | + | + | − | − |
| MW01-003CS | + | + | + | + | − | + |
| MW01-035CZ | − | + | ± | − | − | − |
| MW01-096CZ | | | | | | − |
| MW01-035AZ | − | + | ± | − | − | − |
| MW01-035BZ | − | + | + | − | − | − |
| MW01-125AZ | + | − | − | + | − | ± |
| MW01-086B | − | | + | | | |
| MW01-127Z | − | + | − | + | − | + |
| MW01-161BZ | − | + | − | − | − | − |
| MW01-012AZ | − | + | − | − | − | − |
| MW01-103B | ± | − | + | | | + |
| MW01-110B | | + | | | | + |
| MW01-129B | | | | | | |
| MW01-128B | | | | | | |
| MW01-021Z | + | + | + | | | + |
| MW01-013Z | − | + | + | | | + |
| MW01-176AZ | + | + | − | − | − | − |
| MW01-180AZ | | | | | | |
| MW01-031Z | − | − | + | | | + |
| MW01-022AZ | ± | + | + | − | − | − |

TABLE 7-continued

| Cpd ID | DAPK | CaMPK II | MLCK | PKC | PKA | BV-2 |
|---|---|---|---|---|---|---|
| MW01-133Z | − | − | ± | − | − | ± |
| MW01-096EZ |  |  | − |  |  | ± |
| MW01-145B1Z | − |  |  |  |  |  |
| MW01-145B2Z |  |  |  |  |  | − |
| MW01-024Z | + | − | − | − | − | − |
| MW01-196-AS | + | − | − | − | − | − |

IV. Myosin Light Chain Kinase (MLCK) Inhibition and Effect on Acute Lung Injury.

Lung injury following severe infection or trauma, and the associated complications of mechanical ventilation, are significant problems in critical care medicine. Acute lung injury due to sepsis or mechanical ventilation is associated with high mortality and morbidity. Lung infections are the primary cause of death in 27% of patients hospitalized annually with lung disease in the US. Mechanical ventilation may also result in secondary inflammatory lung injury which is itself a significant cause of morbidity. Therapies which reduce acute inflammatory lung injury would therefore be of direct clinical benefit in the treatment of critically ill patients. Both sepsis and mechanical lung injury cause dysregulation of normal pulmonary endothelial cell function. Endothelium integrity is critical to pulmonary function and is associated with resistance to lung damage. Although cellular and molecular studies indicate the importance of endothelial cell myosin light chain kinase (EC MLCK) to endothelial cell function, there has, heretofore, been no direct link between MLCK and susceptibility to acute lung damage. This lack of a linkage together with the emergence of protein kinases as viable drug discovery targets emphasizes the need to establish the relationship between EC MLCK and lung injury.

Demonstrating, further, the utility of this invention an EC MLCK knockout mouse was compared in its response to that of wild-type (WT) mice after intraperitoneal injection of lipopolysaccharide (LPS). The EC MLCK knockout mice exhibit a dramatically decreased susceptibility to lung injury compared to WT mice, and show enhanced survival when subjected subsequently to mechanical ventilation. A representative composition of this invention, an inhibitor of MLCK, also ameliorates the effects of LPS-induced lung injury in WT mice. These convergent results indicate the in vivo importance of EC MLCK in susceptibility to lung injury, and suggest that MLCK and related protein kinases are targets for the compositions of this invention, in the treatment of pulmonary disease.

Disruption of normal endothelial cell (EC) function is a cardinal event in the pathogenesis of acute lung injury in response to severe infection, trauma or mechanical ventilation (Garcia, 1995; Fan, 2001; Fishman 1998). In addition to the barrier function of normal endothelium, recent evidence demonstrates an active role for EC in the regulation of inflammation, hemostasis and angiogenesis (Stevens, NHBLI 2001). Phosphorylation of myosin light chain by the calcium calmodulin-dependent protein kinase, myosin light chain kinase (MLCK) is a critical step in EC barrier dysfunction in vitro (Tinsley, 2000; Garcia 1995-J Cell Physiol paper). Inhibition of MLCK also reduces ventilator-induced lung injury in explanted lung (Parker). Recent appreciation of the contribution of EC function to multiple disease states (Stevens NHBLI and any other appropriate NIH statement) underscores the need for further understanding of the role of EC and MLCK in disease states. The lack of a specific animal model has precluded the study of the contribution of MLCK to acute inflammatory lung injury in vivo. As part of this investigation, a targeted knockout (KO) mouse model of EC MLCK was developed as described below and using literature techniques, to determine (1) the specific role this kinase may play in acute lung injury, and (2) demonstrate proof of principle for further use of the compositions of this invention in the inhibition of protein kinases.

The MLCK gene locus encodes the larger EC MLCK (MLCK210) and the shorter smooth muscle MLCK (MLCK108), as well as a small non-kinase protein (kinase related protein, KRP) that stabilizes myosin II filaments. Each protein has a variety of splice variants. The two MLCKs appear to be produced by an alternative promotion and splicing mechanism, whereas the KRP is an independently regulated gene embedded within the larger MLCK gene and has its promoter within an MLCK intron. By targeting an upstream, EC MLCK specific intron and by the introduction of a stop codon, EC MLCK was selectively knocked out but smooth muscle MLCK and KRP production were preserved. The presence of the mutant allele was confirmed by Southern blotting.

The 6.9-Kb band corresponds to the wild-type allele and the 7.7 Kb band corresponds to the mutant allele. The selective KO of EC MLCK using was confirmed Western blotting. Homogenates of lung tissue from WT (C57B1/6) and KO mice were analyzed using an anti-MLCK antibody that recognizes all three proteins produced by the MLCK gene locus (EC MLCK, SM MLCK, and KRP). Two major splice variants of lung EC MLCK were detected in WT mouse lung, but not in the KO mouse strain. The levels of SM MLCK and KRP were unchanged between WT and KO. No differences were observed in litter size, fertility and viability in the KO mice compared to WT. No dysmorphic features were found in the KO mice in any organ including lung on gross pathologic examination (data not shown).

To determine the role of EC MLCK in lung injury during sepsis, the Gram-negative endotoxin, lipopolysaccharide (LPS) was used. LPS administration is associated with the release of pro-inflammatory cytokines as well as inflammatory infiltrates and pulmonary edema (Yoshinari, 2001). Accordingly, the effect of LPS administration on lung injury was compared in WT and KO mice. After 24 hour exposure to LPS, WT mice showed evidence of diffuse lung injury with intravascular and interstitial hemorrhage. In contrast, KO mice exhibited no evidence of injury. In WT mice, there were numerous thrombi occluding vessels or adherent to the endothelium, whereas in the KO mice the red blood cells (RBCs) remained within the vessel lumen. WT mouse lung showed multiple foci of inflammatory cells adjacent to the endothelium of large and small vessels. In contrast, in the KO mouse lung, the integrity of the endothelium was preserved with rare inflammatory infiltrate or RBC extravasation. Electron microscopy (EM) confirmed differences in EC properties between WT and KO mice following LPS exposure. WT mice showed extravasation of numerous RBCs across the EC barrier into the alveolar space, which was not observed in the KO mice. The endothelium of the WT animals appeared thin and attenuated compared to the normal appearance of the endothelium in the KO animals. These data together suggested that the impairment in lung EC barrier function associated with endotoxin exposure in WT mice was prevented by the selective KO of EC MLCK.

To confirm the specific role of EC MLCK in the reduced susceptibility of KO mice to endotoxin-mediated lung injury, a representative composition of this invention was used to determine whether pharmacologic inhibition of MLCK would also reduce LPS-induced lung injury. (See, examples 25-26, below.) WT mice were treated with 2.5 mg/kg of a representative MLCK inhibitor (e.g., cpd MW01-022AZ) 1 hour prior to administration of LPS. After a 24 hour recovery period, mice treated with this compound showed no evidence of lung injury associated with LPS exposure. The protection against endotoxin-mediated injury afforded by this compound in vivo shows (1) that EC MLCK (together with other such protein kinases) is a valid treatment target in septic (and, below, mechanical) injury in the lung, and (2) that this invention can be used to inhibit protein kinase activity and reduce acute lung injury.

As mentioned above, the adverse effects of mechanical ventilation also represent a significant cause of morbidity in the care of the critically ill patient. The signaling pathways mediating this injury are not well understood but numerous studies have implicated inflammatory mediators in the pathophysiology of ventilator-induced lung injury (VILI) (Dos Santos, 2000; Whitehead, 2002). In order to further assess the role of EC MLCK in the inflammatory response to VILI, WT and KO mice were subjected to mechanical ventilation after exposure to LPS. Both KO and WT mice tolerated mechanical ventilation alone and completed a 60 minute period of ventilation without difficulty. In contrast, WT mice treated with LPS died within 15 minutes of ventilation (n=7). However, the majority (67%; n=6) of KO mice treated with LPS survived 60 minutes of ventilation.

A principal finding of this study is the robust protection against endotoxin-mediated inflammatory lung (mechanical or infectious) injury observed in mice lacking EC MLCK. The pivotal role for this kinase in EC function extends findings from previous in vitro studies and is further supported herein by demonstration of similar protection afforded by the pharmacologic inhibition of MLCK. The efficacious use of this invention, by way of a small molecule composition, in preventing endotoxin-mediated lung injury lends credence to the identification of MLCK and associated protein kinases as treatment targets in human disease. The availability of a KO mouse with selective deletion of EC MLCK will facilitate further study of the organ-specific contribution of MLCK to other vasculopathic diseases, and can be utilized to confirm the compositions of this invention as a novel class of protein kinase inhibitors.

EXAMPLE 22

Animal care. As mentioned above and in accordance therewith, all procedures relating to this aspect of the invention were performed in accordance with relevant National Institutes of Health guidelines. All experimental procedures were approved by the Institutional Animal Care and Use Committee of Northwestern University, Chicago.

EXAMPLE 23

Molecular phenotyping of KO mice and confirmation of EC MLCK gene KO. Genomic DNA was extracted from tails of homozygous KO, wild type (WT), and heterozygous mice. Each DNA sample was digested with EcoRI and hybridized in Southern blots with a 1.9 Kb 5' probe. Homogenates of lung tissue were prepared from KO and WT mice and analyzed by western blot using an anti-MLCK antibody that recognizes all three proteins produced by the MLCK gene locus (EC MLCK, SM MLCK, and KRP).

EXAMPLE 24

Endotoxin-mediated lung injury. LPS (Sigma, St. Louis, Mo.) (10 mg/kg) was administered via intraperitoneal (ip) injection. Animals were allowed to recover for 24 hours prior to determination of lung injury. Control animals received an equivalent volume of sterile saline.

EXAMPLE 25

Synthesis of MLCK inhibitor. The selective MLCK small molecule inhibitor of this example (reference structure MW01-022AZ, shown below) was made according to procedures described herein. Briefly, alkylation of commercially available 3-amino-6-chloropyridazine (Alfa Aesar) at the 2-position resulted in the 11-(3-Chloro-6-imino-6H-pyridazin-1-yl)-undecanoic acid ethyl ester, which was then hydrolyzed to the corresponding carboxylic acid. The carboxylic acid derivative was then coupled to the 3-amino-6-phenyl-pyridazine to yield the final compound.

EXAMPLE 26

Compounds of the type (MW01-022AZ):

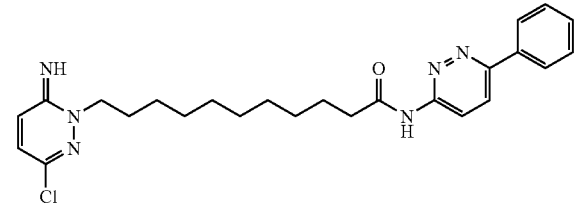

are shown to be comparatively selective (using assay procedures and data analyses previously described) for inhibition of MLCK and related enzymes such as Rho kinase, and are bioavailable in various other animal models of disease. As mentioned above, administration by intraperitoneal injection (IP) of MW01-022AZ resulted in protection from acute injury (ALI). Specifically, lungs from treated animals appeared close to normal on histological exam 24 hours after intraperitoneal injection of 2.5 mg/kg body weight of MW01-022AZ. The stimulus in this example was IP injection of 10 mg/kg body weight of the bacterial endotoxin, lipopolysaccharide (LPS). The treatment with MW01-022AZ represents a clinically relevant dose of a kinase inhibitor therapeutic based on prior art with other kinases. Other compositions of this invention, having the structural relationships described and/or illustrated above, can also be employed. For instance, such compositions can without limitation include those having the same or a similar A component (6-chloropyridazinyl) and/or comparable $R_2$ (alkyl), G (acyl) and/or B (pyrimidine-substituted piperazinyl) components.

The composition of this invention is also utilized in the context of cardiac hypoxia/ischemia. With reference to the previous section and the experimental detail provided therein, such compounds can be administered in vivo by interperitoneal injection. Removal of heart tissue, perfused in a standard assay for cardiac ischemia shows protection and enhancement of cardiac blood flow. Accordingly, such compositions can be utilized as described herein and as would be well known to those skilled in the art for the moderation of cardiovascular tissue damage or loss under such conditions.

As a further embodiment of this invention, compositions of the sort described above are demonstrated directly as MLCK inhibitors. Test results to date show similar trends and comparable protection by a single administration of such a compound to wild type (WT) mice as that seen with MLCK knock out (KO) mice. See, for instance, the results and data of FIG. 9.

EXAMPLE 27

Histologic analysis of lung injury after LPS exposure. Following 24 hour exposure to LPS, WT and KO mice were perfused with 4% paraformaldehyde. Paraffin-embedded H&E stained sections were prepared by standard techniques. Qualitative assessment of injury in WT and KO mice after LPS exposure was performed in blinded fashion by grading the histological features (hemorrhage, inflammation, atelectasis) as mild (focal); moderate (multifocal); or severe (diffuse).

EXAMPLE 28

Electron microscopy of lung sections. Lung samples from KO and WT mice were fixed using published methods (Fan, 1996) with 2% paraformaldehyde and 2.5% glutaraldehyde in 0.05M cacodylate buffer (PH 7.2, 4c) for 4 hours, washed overnight in 0.05M cacodylate buffer, postfixed in 1% osmium tetroxide in cacodylate buffer (PH 7.4) for 1 hour at 4° C., and embedded in Epon812. Ultrasections for EM were contrasted with uranyl acetate and lead citrate.
V. Protein Kinase Inhibition and Cancer Treatment Strategies.

Cancer is a manifestation of deregulated signaling pathways that mediate cell growth and programmed cell death. In addition to abnormal cell proliferation contributing to increased cell number, programmed cell death (apoptosis) of abnormal cells is also suppressed in tumor cells. Deregulated cell growth and apoptosis, the defining features of all cancers, occur as the result of defective signaling pathways. Protein kinases, as discussed above, are essential elements in such signaling pathways. As a result, it is believed selective and potent protein kinase inhibitors have the potential to become useful pharmacological agents in the treatment of such disease states. Several recently launched anti-cancer drugs are in development of target receptors for growth factors and the signaling pathways activated by them. A number of protein kinase inhibitors have entered clinical trials. (See, e.g., Gibbs, J: Mechanism-based target identification and drug discovery in cancer research. *Science*(2000) 287:1969-1973; Sridhar, R., Hanson-Painton, O., Cooper Dr., et al.: Protein kinases as therapeutic targets. *Pharm. Res*. (2000) 17:1345-1353.) Further, in May 2001, imantinib (Gleevec™, STI-571, Novartis) an inhibitor of bcr-abl tyrosine kinase, was approved for treatment of chronic myelogenous leukemia. Accordingly, the compositions of this invention—in light of demonstrated inhibitory effects in a variety of protein kinase systems—can be utilized in further study and/or cancer treatment.

While the principles of this invention have been described in connection with specific embodiments, it should be understood clearly that these descriptions are added only by way of example and are not intended to limit, in any way, the scope of this invention. For instance, the present invention can include various other compositions of the sort described herein, the range of which is limited only by way of available starting materials and synthetic technique. Likewise, such compositions can be used in conjunction with other methodologies, as would be understood by those skilled in the art and made aware of this invention. Lastly, it will be understood that the examples and descriptions provided herein are non-limiting, but presented only by way of illustrating various aspects and features relating to the structural components, compositions and/or methods of this invention. Other advantages, features and benefits thereof will become apparent from the claims hereinafter, with the scope of such claims determined by their reasonable equivalents, as would be understood by those skilled in the art.

Figure 1:
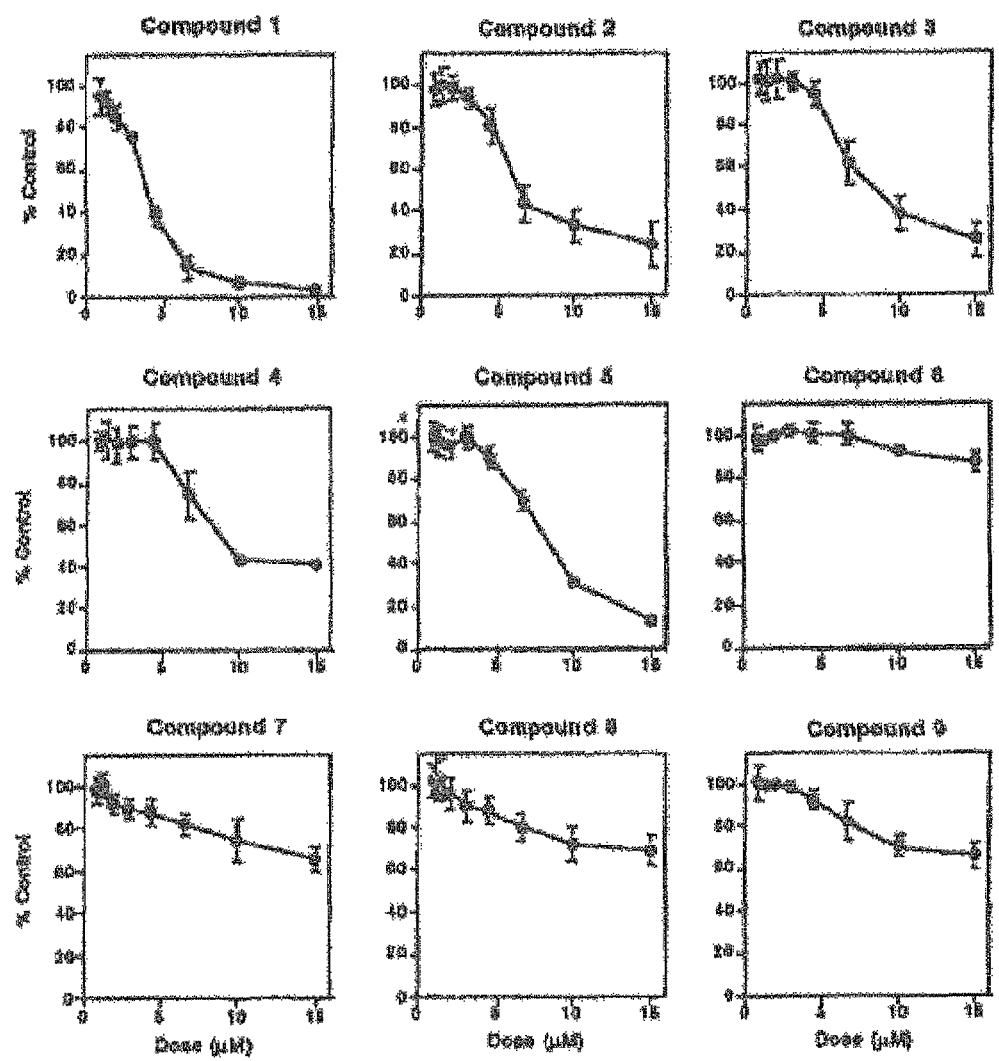
FIG. 1. illustrates cell-based screen for inhibition of LPS-stimulated NO release. BV-2 microglial cells incubated with LPS in the presence of increasing concentrations of compounds 1-9, and accumulation of NO in conditioned media.
Figure 2:
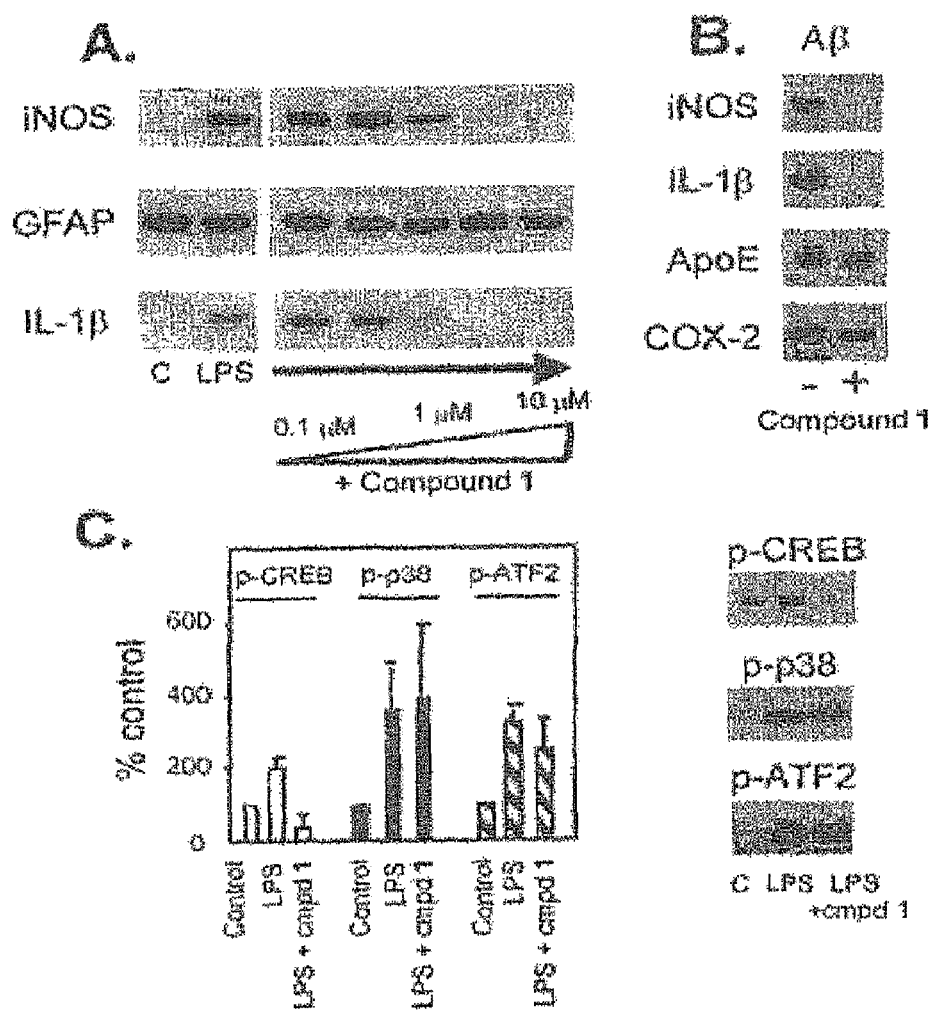
FIG. 2 illustrates selective effects of compound 1 (MW01-070C) on glial activation responses and gene-regulating protein kinase pathways. BV-2 cells and rat astrocytes treated with control buffer (C) or stimulated with LPS or Aβ1-42 peptide in the presence or absence of compound 1, and cell lysates were analyzed by Western blots.
Figure 3A:
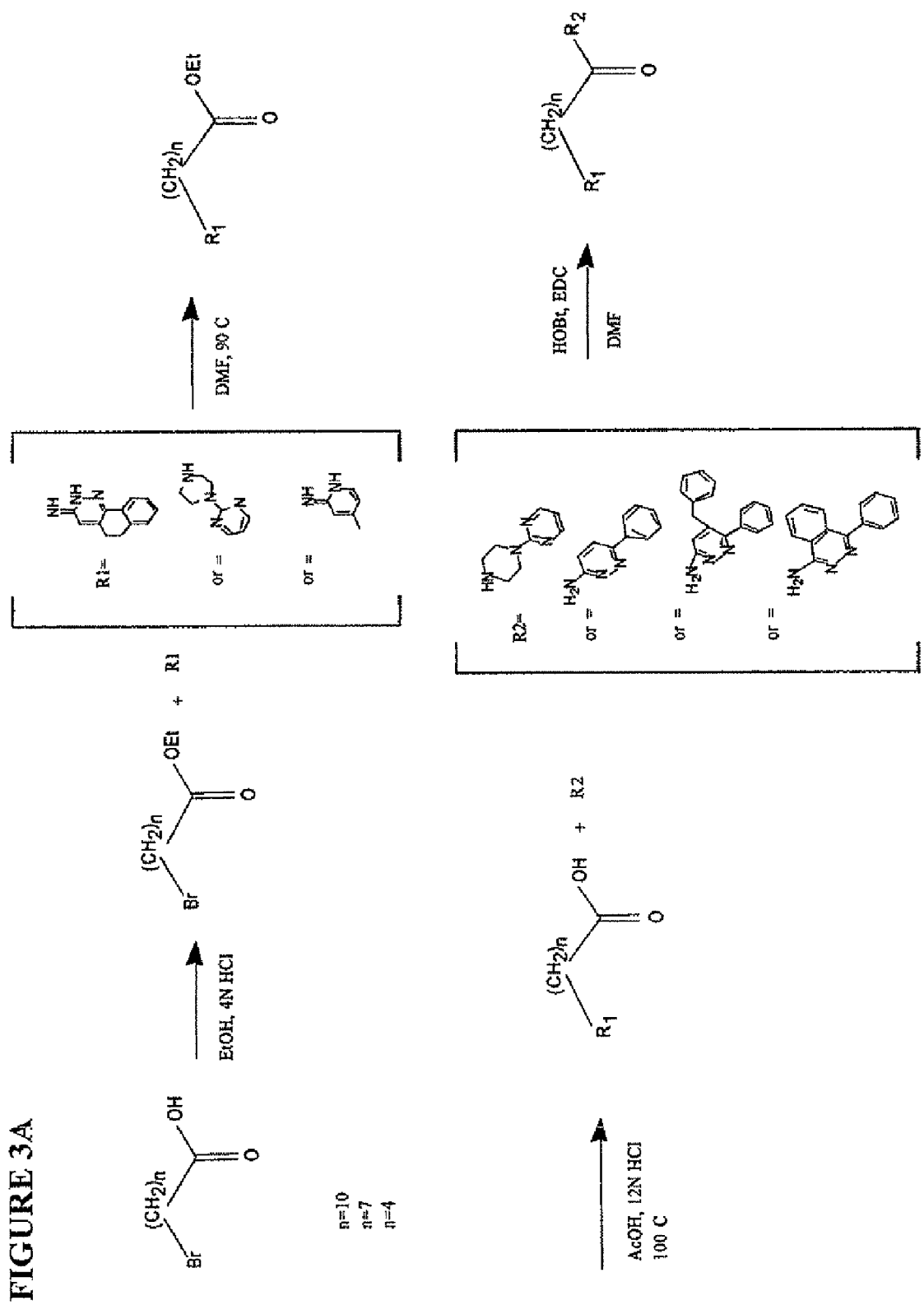
FIG. 3. illustrates another representative synthetic scheme and resulting structures of the corresponding compositions.
Figure 3B:
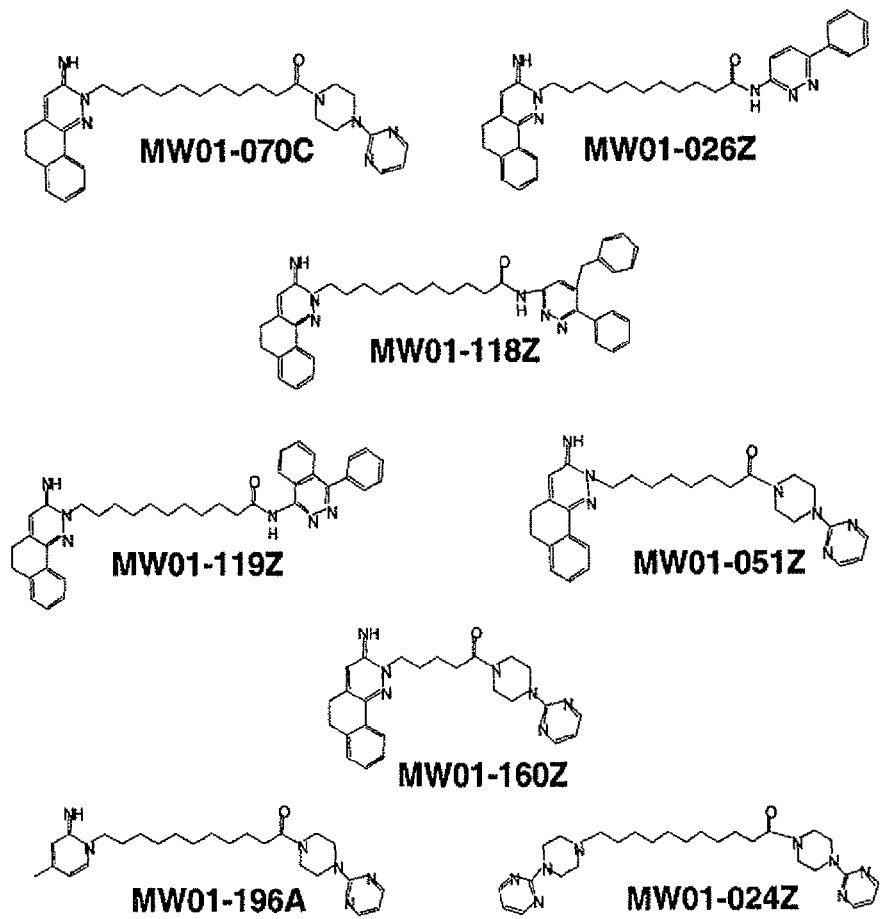
Figure 4:
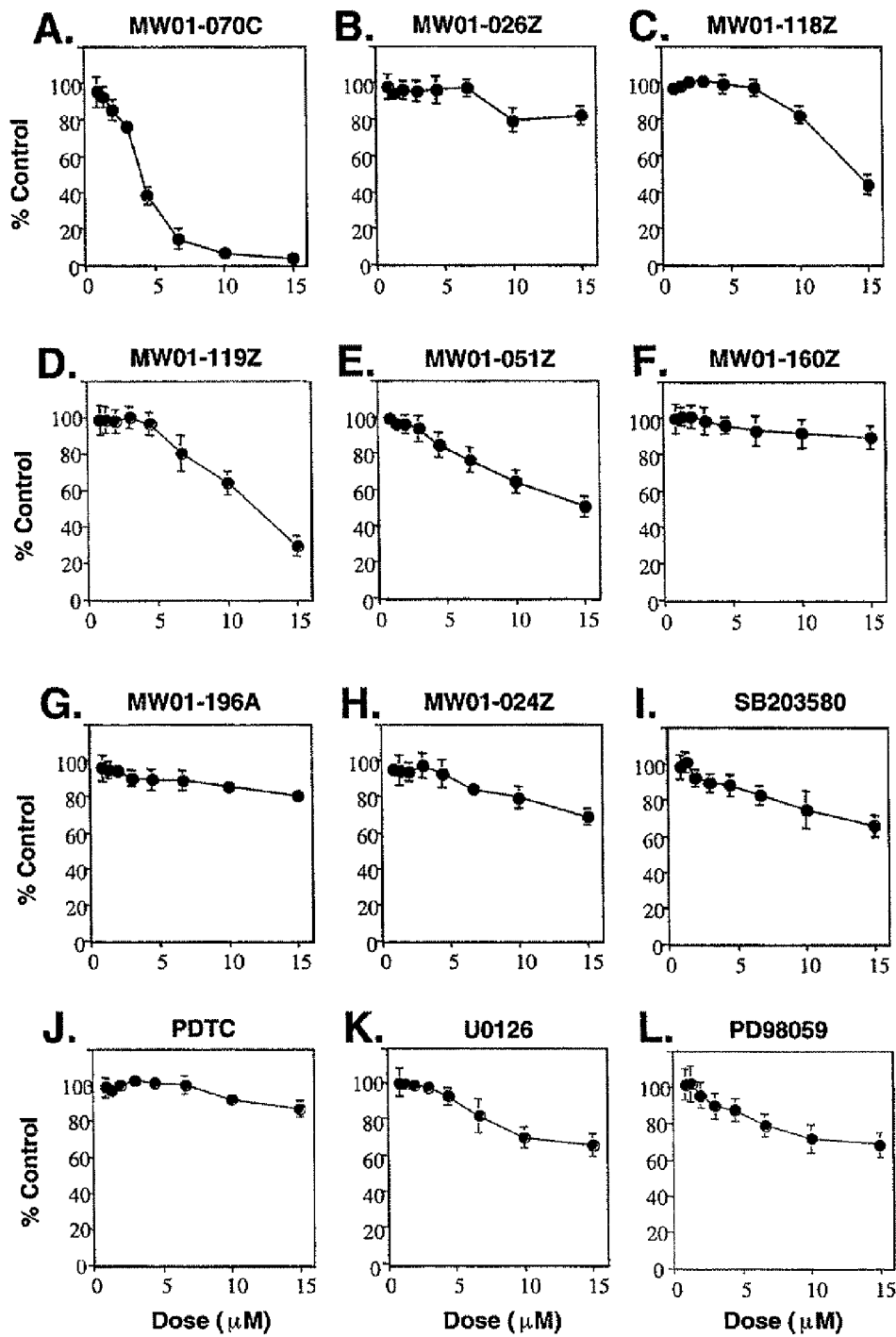
FIG. 4. illustrates cell-based screen for functional effects of synthetic compounds on LPS-stimulated NO release from BV-2 cells.
Figure 5:
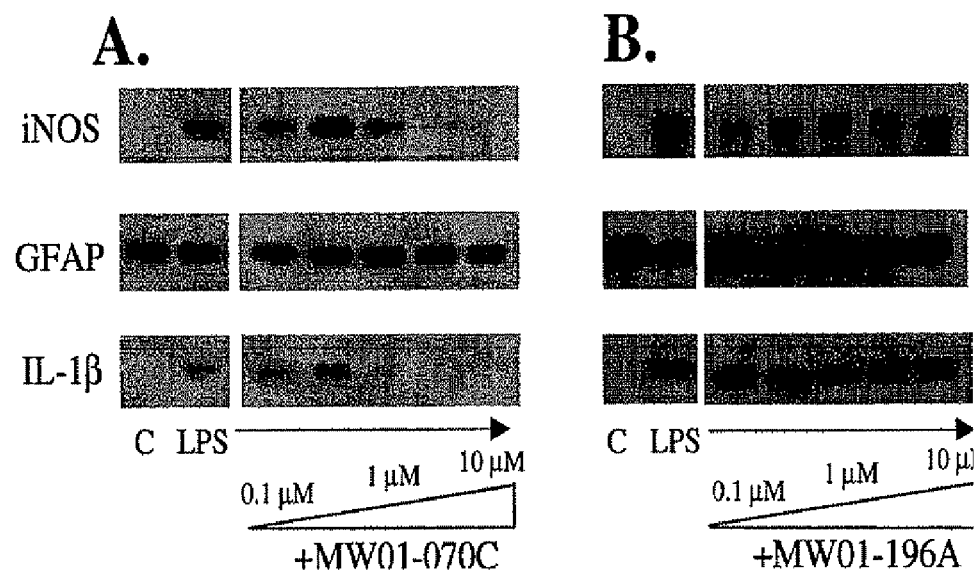
FIG. 5. illustrates effects of two compounds on LPS-stimulated INOS and IL-1β production in rat astrocyte cultures.
Figure 6:
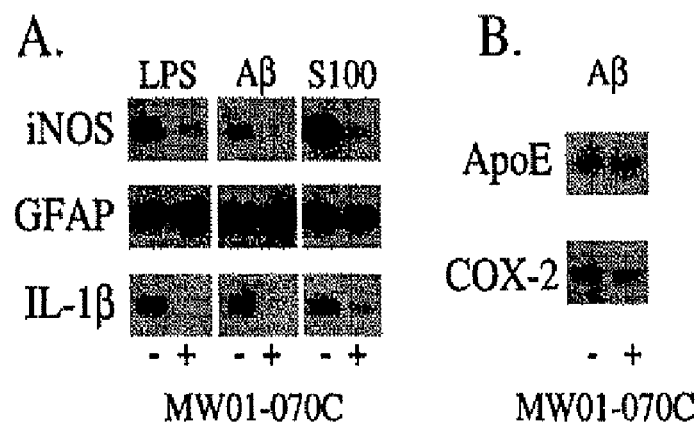
FIG. 6. illustrates effects of MW01-070C on astrocytes treated with various activating stimuli, and analysis of multiple activation responses.
Figure 7:
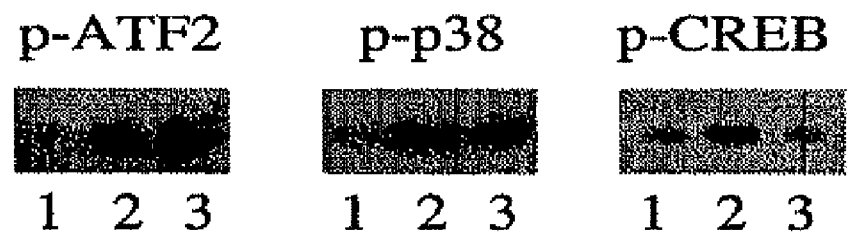
FIG. 7. illustrates effects of MW01-070C on phosphorylation of transcription factors and an upstream activating kinase.
Figure 8:
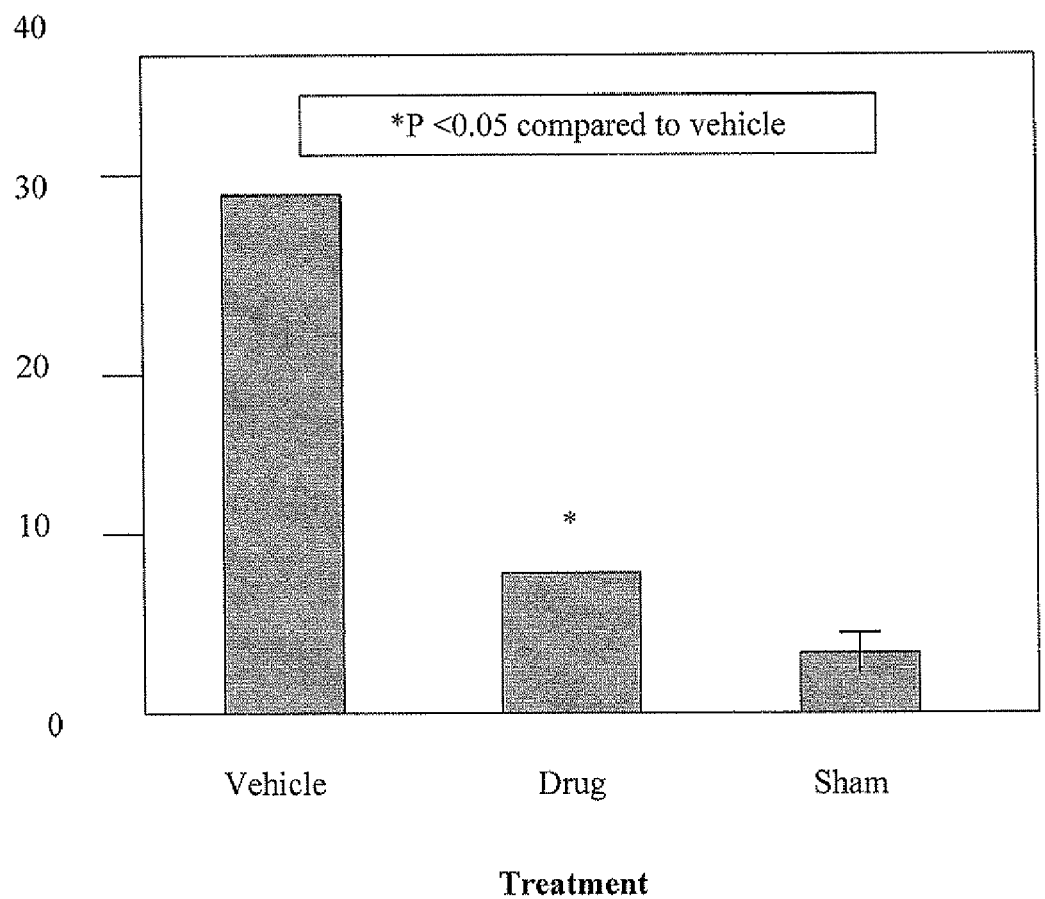
FIG. 8. illustrates comparative data analysis pertaining to the indicated animal subjects, in terms of hemispheric weight loss.
Figure 9:
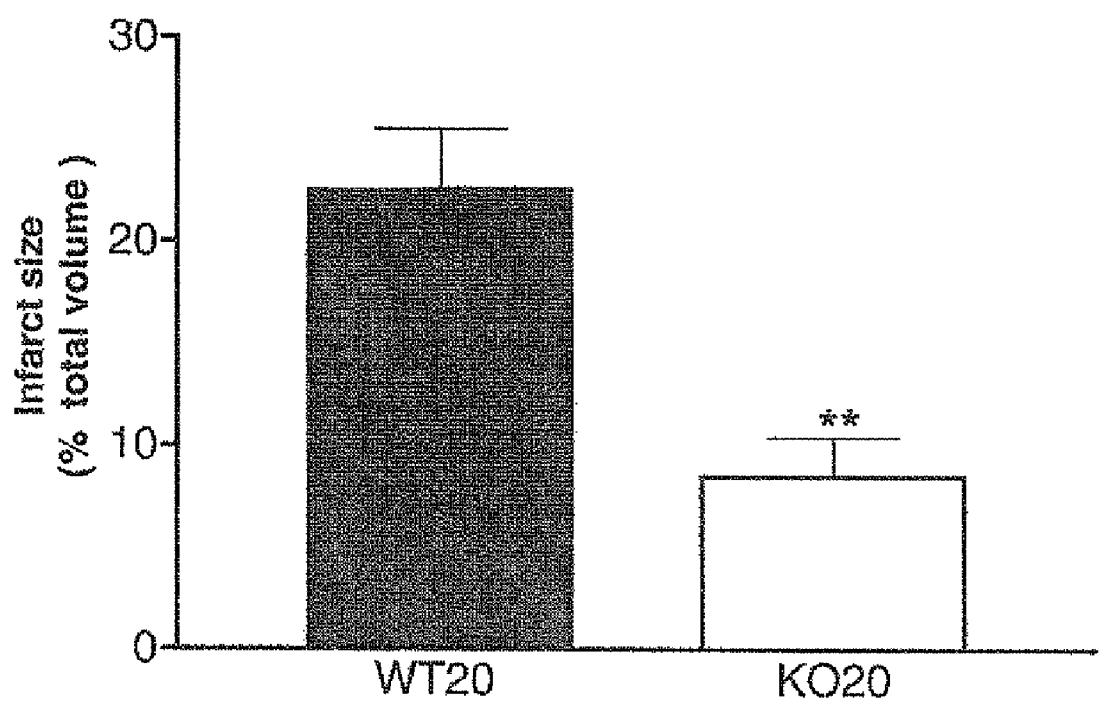
FIG. 9. illustrates results and data for showing similar trends and comparable protection by a single administration of a compound to wild type (WT) mice as that seen with MLCK knock out (KO) mice.

The invention claimed is:
1. An N-heterocyclic compound of the structural formula

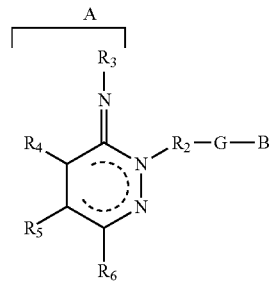

wherein
A is a first pyridazinyl component; and $R_3$ is a component selected from the group consisting of hydrogen, alkyl and substituted alkyl moieties, arylalkyl and substituted arylalkyl moieties; phenyl and substituted phenyl moieties;
$R_4$ is a component selected from the group consisting of hydrogen, halogen, alkyl, substituted alkyl, amino, arylalkyl and substituted arylalkyl moieties, phenyl and substituted phenyl moieties, or alkyl and substituted alkyl moieties as can provide a carbocyclic or a heterocyclic moiety with $R_5$;

R5 is a component selected from the group consisting of hydrogen, halogen, alkyl, substituted alkyl; phenyl, substituted phenyl, heterocyclic and substituted heterocyclic moieties, arylalkyl and substituted arylalkyl moieties, or alkyl and substituted alkyl moieties as can provide a carbocyclic or a heterocyclic moiety with R4 or R6;

R6 is a component selected from the group consisting of hydrogen, halogen, alkyl, substituted alkyl, phenyl, substituted phenyl, heterocyclic and substituted heterocyclic moieties, arylalkyl and substituted arylalkyl moieties, or a substituted phenyl moiety providing a carbocyclic or a heterocyclic moiety with R5;

R2 is a divalent component coupling A and G, said component selected from the group consisting of alkyl, cycloalkyl, acyl, alkylacyl, amido, alkylamido moieties, and further including said moieties having at least one unsaturated carbon-carbon bond sequence;

G is a divalent component coupling R2 and B, said component selected from the group consisting of alkyl, cycloalkyl, acyl, alkylacyl, amido, alkylamido, ureido, sulfonamido, thio, and primary, secondary and tertiary amine moieties; and B is a second pyridazinyl component of the structural formula

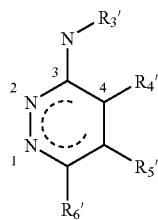

wherein R3' is a component selected from the group consisting of hydrogen, alkyl and substituted alkyl; phenyl and substituted phenyl, and arylalkyl and substituted arylalkyl moieties;

R4' is a component selected from the group consisting of hydrogen, halogen, alkyl, substituted alkyl, amino, arylalkyl and substituted arylalkyl moieties, phenyl and substituted phenyl moieties, or alkyl and substituted alkyl moieties as can provide a carbocyclic or a heterocyclic moiety with R5';

R5' is a component selected from the group consisting of hydrogen, halogen, alkyl, substituted alkyl; phenyl, substituted phenyl, heterocyclic and substituted heterocyclic moieties, arylalkyl and substituted arylalkyl moieties, or alkyl and substituted alkyl moieties as can provide a carbocyclic or a heterocyclic moiety with R4' or R6';

R6' is a component selected from the group consisting of hydrogen, halogen, alkyl, substituted alkyl, phenyl, substituted phenyl, heterocyclic and substituted heterocyclic moieties, arylalkyl and substituted arylalkyl moieties, or a substituted phenyl moiety providing a carbocyclic or a heterocyclic moiety with R5';

wherein B is coupled with the G component at one of the 1-, 2-, 3-nitrogen- and 4-positions thereof.

2. An N-heterocyclic compound of claim 1, wherein B is coupled with the G component at the 3-nitrogen thereof.

3. A compound of claim 2, wherein R6 is a halogen moiety.

4. A compound of claim 3, wherein R6 is a chlorine moiety.

5. A compound of claim 2, wherein G is an acyl or amido moiety.

6. A compound of claim 3, wherein G is an acyl or amido moiety.

7. A compound of claim 4, wherein G is an acyl or amido moiety.

8. A compound of claim 3, wherein R2 is a $(CH_2)_n$ alkyl moiety and n is 10.

9. A compound of claim 5, wherein R2 is a $(CH_2)_n$ alkyl moiety and n is 10.

10. A compound of claim 6, wherein R2 is a $(CH_2)_n$ alkyl moiety and n is 10.

11. An N-heterocyclic compound of claim 6, wherein R2 is a $(CH_2)_n$ alkyl moiety and n is 4-12; R3, R4, R5, R3' and R5' are hydrogen, and R4' is hydrogen or alkyl.

12. An N-heterocyclic compound of claim 10, wherein R3, R4, R5, R3', R4', and R5' are hydrogen.

13. An N-heterocyclic compound of claim 12, wherein R6' is phenyl or substituted phenyl.

14. A compound of the following structural formula:

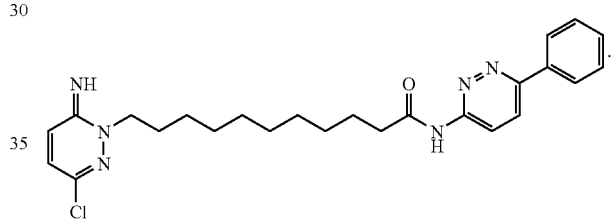

15. A pharmaceutical composition comprising a compound of claim 1 and a pharmaceutically acceptable diluent, carrier, adjuvant or vehicle.

16. A pharmaceutical composition comprising a compound of claim 14 and a pharmaceutically acceptable diluent, carrier, adjuvant or vehicle.

17. A method for treating or reducing acute lung injury in a subject comprising administering to the subject a compound of claim 1.

18. A method for treating complications from mechanical ventilation in a subject comprising administering to the subject a compound of claim 1.

19. A method for treating or reducing acute lung injury in a subject comprising administering to the subject a compound of claim 14.

20. A method for treating complications from mechanical ventilation in a subject comprising administering to the subject a compound of claim 14.

* * * * *

UNITED STATES PATENT AND TRADEMARK OFFICE
CERTIFICATE OF CORRECTION

PATENT NO. : 8,088,774 B2  Page 1 of 1
APPLICATION NO. : 12/831787
DATED : January 3, 2012
INVENTOR(S) : Daniel Martin Watterson et al.

It is certified that error appears in the above-identified patent and that said Letters Patent is hereby corrected as shown below:

Title Page, Item (73) Assignees, Line 5 reads: "Scientific Research Centre, Paris Cedix" should read --Scientific Research Centre, Paris Cedex--.

Column 83, line 30, delete the formula and add the following

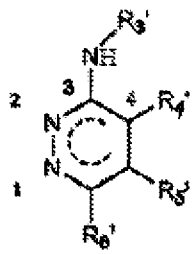

-- --.

Signed and Sealed this
Third Day of July, 2012

David J. Kappos
*Director of the United States Patent and Trademark Office*